US012741952B2

(12) United States Patent
Bouche et al.

(10) Patent No.: US 12,741,952 B2
(45) Date of Patent: Sep. 22, 2026

(54) COMPOUNDS

(71) Applicant: Hoffmann-La Roche Inc., Little Falls, NJ (US)

(72) Inventors: Lea Aurelie Bouche, Basel (CH); Wolfgang Guba, Müllheim (DE); Georg Jaeschke, Basel (CH); Stefanie Katharina Mesch, Basel (CH); Andreas Michael Tosstorff, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 389 days.

(21) Appl. No.: 18/506,492

(22) Filed: Nov. 10, 2023

(65) Prior Publication Data

US 2024/0208928 A1 Jun. 27, 2024

Related U.S. Application Data

(63) Continuation of application No. PCT/EP2022/062525, filed on May 10, 2022.

(30) Foreign Application Priority Data

May 12, 2021 (EP) .................................... 21173452
Nov. 22, 2021 (EP) .................................... 21209447
Dec. 20, 2021 (EP) .................................... 21215859

(51) Int. Cl.
*C07D 401/12* (2006.01)
*A61K 31/53* (2006.01)
(Continued)

(52) U.S. Cl.
CPC ........... *C07D 401/12* (2013.01); *A61K 31/53* (2013.01)

(58) Field of Classification Search
CPC .. C07D 401/12; C07D 403/12; C07D 405/14; C07D 471/08; C07D 253/07;
(Continued)

(56) References Cited

U.S. PATENT DOCUMENTS 6,653,316 B1 * 11/2003 South .................. C07D 401/04 544/320
2011/0190495 A1 8/2011 Tian et al.
(Continued)

FOREIGN PATENT DOCUMENTS

CL 201401103 4/2014
CL 202002851 11/2020
(Continued)

OTHER PUBLICATIONS

Baldwin, A.G., et al., "Inhibiting the Inflammasome: A Chemical Perspective" J Med Chem 59(5):1691-1710 (Mar. 10, 2016).
(Continued)

*Primary Examiner* — Jeffrey S Lundgren
*Assistant Examiner* — Alexander K. Showalter
(74) *Attorney, Agent, or Firm* — Jelena Libby

(57) ABSTRACT

The invention relates to novel compounds having the general formula Ib

Ib (Continued)

wherein $R^1$, $R^2$, $R^3$, $R^4$, $R^5$, and Z are as described herein, composition including the compounds and methods of using the compounds.

25 Claims, 1 Drawing Sheet

(51) Int. Cl.

| | |
|---|---|
| ***A61P 11/06*** | (2006.01) |
| ***C07D 253/07*** | (2006.01) |
| ***C07D 403/12*** | (2006.01) |
| ***C07D 405/04*** | (2006.01) |
| ***C07D 405/14*** | (2006.01) |
| ***C07D 471/04*** | (2006.01) |
| ***C07D 471/08*** | (2006.01) |

(58) Field of Classification Search
CPC .... C07D 405/04; C07D 471/04; A61K 31/53; A61P 11/06
See application file for complete search history.

(56) References Cited

U.S. PATENT DOCUMENTS

| | | | |
|---|---|---|---|
| 2020/0361898 | A1 | 11/2020 | Farady et al. |
| 2024/0239758 | A1 | 7/2024 | Inagaki et al. |

FOREIGN PATENT DOCUMENTS

| | | | |
|---|---|---|---|
| CL | 202100191 | | 1/2021 |
| CL | 202103012 | | 11/2021 |
| CL | 202302821 | | 9/2023 |
| CL | 202303491 | | 11/2023 |
| CL | 202401832 | | 6/2024 |
| EA | 032005 | | 3/2019 |
| EP | 3272739 | A1 | 1/2018 |
| RU | 2252217 | C2 | 5/2005 |
| WO | 00/66568 | | 11/2000 |
| WO | 2013/067274 | A1 | 5/2013 |
| WO | 2014/028459 | A1 | 2/2014 |
| WO | 2017/100726 | A1 | 6/2017 |
| WO | 2017/184604 | A1 | 10/2017 |
| WO | 2017/184746 | A1 | 10/2017 |
| WO | 2019/034690 | A1 | 2/2019 |
| WO | 2019/092170 | A1 | 5/2019 |
| WO | 2019/191229 | A1 | 10/2019 |
| WO | 2019/211463 | A1 | 11/2019 |
| WO | 2020/021447 | | 1/2020 |
| WO | 2020/163248 | A1 | 8/2020 |
| WO | 2020/190793 | A1 | 9/2020 |
| WO | 2020/234715 | A1 | 11/2020 |
| WO | 2021/209539 | A1 | 10/2021 |
| WO | 2021/209552 | A1 | 10/2021 |
| WO | 2021/219784 | A1 | 11/2021 |
| WO | 2022/200580 | | 9/2022 |
| WO | 20228253936 | | 12/2022 |
| WO | 2023/122588 | | 6/2023 |

OTHER PUBLICATIONS

Cocco, M., et al., "Electrophilic Warhead-Based Design of Compounds Preventing NLRP3 Inflammasome-Dependent Pyroptosis" J. Med. Chem. 57(24):10366-10382 (Nov. 24, 2014).
International Preliminary Report on Patentability—PCT/EP2022/062525 issued Nov. 28, 2022, pp. 1-6.
International Search Report with Written Opinion—PCT/EP2022/062525 mailed Aug. 10, 2022, pp. 1-12.
Liu, Y., et al., "NLRP3 inflammasome activation mediates radiation-induced pyroptosis in bone marrow-derived macrophages" Cell Death Dis. 8(e2579):1-9 (2017).
Ozaki, E., et al., "Targeting the NLRP3 inflammasome in chronic inflammatory diseases: current perspectives" J. Inflamm. Res. 8:15-27 (2015).
Satoh, T., et al., "NLRP3 activation induces ASC-dependent programmed necrotic cell death, which leads to neutrophilic inflammation" Cell Death Dis. 4(e644):1-10 (2013).
Wree, A., et al., "NLRP3 inflammasome activation results in hepatocyte pyroptosis, liver inflammation and fibrosis" HEPATOLOGY 59(3):898-910 (Mar. 2014).
Xie and Zhao et al., "Pyroptosis and neurological diseases" Neuroimmunol Neuroinflammation 1(2):60-65 (Sep. 2014).
"Short Course in Molecular Pharmacology" edited by Sergeev P.V., M., 1975, p. 10.
Belikov V.G. Pharmaceutical Chemistry. Textbook, M.: "MEDpress-inform", 2007, pp. 27-29.
Belikov V.G. Pharmaceutical Chemistry. Textbook, M.: "MEDpress-inform", 2007, p. 11.
Dyson G., May P. Chemistry of Synthetic Drugs, translated from English. M.: Mir, 1964, pp. 12-19.
Fundamentals of Medical Prevention. Teaching aid for students and cadets of advanced training cycles at state professional educational institutions. Novosibirsk, 2016, pp. 13-21.
Gavrilov A.S. Pharmaceutical Technology. Manufacture of Medicaments. Textbook. M.: "GEOTAR-Media", 2010, pp. 20.
Kholodov L.E. et al. "Clinical Pharmacokinetics", M., "Medicine", 1985, pp. 83-98, 134-138, 160, 378-380.
Kummerer, K., "Pharmaceuticals in the Environment" Ann Rev Environ Res 35:57-75 (Nov. 1, 2010).
Smit W., Bochkov A., Caple R. Organic Synthesis. Science and Art: Translated from English. M.: Mir, 2001, pp. 64.
Wood et al., "Developmental Pharmacology—Drug Disposition, Action, and Therapy in Infants and Children" New England Journal of Medicine 349(12):1157-1167 ( 2003).

* cited by examiner

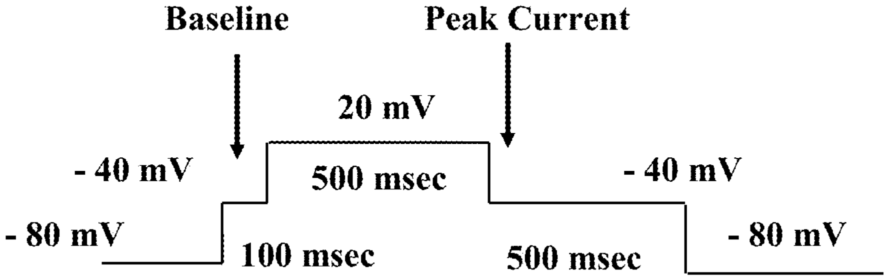
Baseline
Peak Current
20 mV
- 40 mV
500 msec
- 40 mV
- 80 mV
100 msec
500 msec
- 80 mV

COMPOUNDS

CROSS-REFERENCE TO RELATED APPLICATIONS

This application is a Continuation of International Application No PCT/EP2022/062525, filed May 10, 2022, which claims benefit of priority to European Application Nos. 21173452.0 filed May 12, 2021; 21209447.8, filed on Nov. 22, 2021; 21215859.6 filed Dec. 20, 2021, each of which is incorporated herein by reference in its entirety.

FIELD OF THE INVENTION

The present invention relates to organic compounds useful for therapy and/or prophylaxis in a mammal, and in particular to compounds that modulate NLRP3 inhibition.

The present invention provides novel compounds of formula Ib

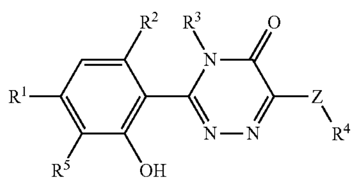

Ib wherein $R^1$ is H, acetyl, $SF_5$, halo, alkyl, haloalkyl, haloalkoxy or nitrile;

$R^5$ is H;

or $R^1$ and $R^5$, and the atoms to which they are bonded, form either an 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with 1 to 2 substituents independently selected from halo or alkyl;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 3 substituents independently selected from halo, alkyl, haloalkyl, hydroxyalkyl, —OH, oxo, —$CO_2$H, cycloalkylalkyl or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl has 1 to 3 substituents independently selected from alkyl, halo, haloalkyl and —OH;

and pharmaceutically acceptable salts.

Furthermore, the invention includes all racemic mixtures, all their corresponding enantiomers and/or optical isomers.

BACKGROUND OF THE INVENTION

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signaling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, for diseases such as Parkinson's disease, Alzheimer's disease and Amyotrophic lateral sclerosis (ALS). Lung diseases have also been shown to be influenced by NLRP3. Furthermore, NLRP3 has a role in the development of liver disease, kidney disease and aging. Many of these associations were defined using $Nlrp3^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signalling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

There is a need to provide compounds with improved pharmacological and/or physiological and/or physicochemical properties and/or those that provide a useful alternative to known compounds.

SUMMARY OF THE INVENTION

The present invention provides novel compounds of formula Ib:

Ib

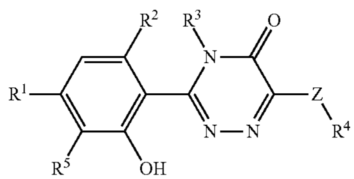

wherein $R^1$ is H, acetyl, $SF_5$, halo, alkyl, haloalkyl, haloalkoxy or nitrile;

$R^5$ is H;

or $R^1$ and $R^5$, and the atoms to which they are bonded, form either an 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with 1 to 2 substituents independently selected from halo or alkyl;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 3 substituents independently selected from halo, alkyl, haloalkyl, hydroxyalkyl, —OH, oxo, —$CO_2$H, cycloalkylalkyl or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl has 1 to 3 substituents independently selected from alkyl, halo, haloalkyl and —OH;

and pharmaceutically acceptable salts.

BRIEF DESCRIPTION OF DRAWINGS

FIG. 1 shows a voltage pattern used to stimulate cells to activate hERG channels and conduct outward IKhERG current, at a stimulation frequency of 0.1 Hz (6 bpm).

DETAILED DESCRIPTION

The term "alkyl" denotes a monovalent linear or branched saturated hydrocarbon group of 1 to 6 carbon atoms. In some embodiments, if not otherwise described, alkyl comprises 1 to 6 carbon atoms ($C_{1-6}$-alkyl), or 1 to 4 carbon atoms ($C_{1-4}$-alkyl). Examples of $C_{1-6}$-alkyl include methyl, ethyl, propyl, isopropyl, n-butyl, iso-butyl, sec-butyl, tert-butyl and pentyl. Particular alkyl groups include methyl, ethyl, propyl and butyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "alkoxy" denotes a group of the formula —O—R', wherein R' is a $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are methoxy and ethoxy.

The term "acetyl" denotes a group of the formula —C(═O)—R', wherein R' is an alkyl group. Examples of acetyl include —C(═O)$CH_3$.

The term "aryl", alone or in combination with other groups, denotes a monovalent cyclic aromatic hydrocarbon moiety consisting of a mono- or bicyclic aromatic ring. Preferred aryl is phenyl. Aryl may be unsubstituted or substituted as described herein.

The term "arylalkyl" denotes an alkyl group wherein one of the hydrogen atoms of the alkyl group has been replaced by an aryl group. Example of an arylalkyl group is phenylalkyl, specifically phenylmethyl.

The term "cycloalkyl" denotes monocyclic or polycyclic saturated or partially unsaturated, non-aromatic hydrocarbon. In some embodiments, unless otherwise described, cycloalkyl comprises 3 to 8 carbon atoms, 3 to 6 carbon atoms, or 3 to 5 carbon atoms. In some embodiments, cycloalkyl is a saturated monocyclic or polycyclic hydrocarbon. In other embodiments, cycloalkyl comprises one or more double bonds (e.g., cycloalkyl fused to an aryl or heteroaryl ring, or a non-aromatic monocyclic hydrocarbon comprising one or two double bonds). Examples of cycloalkyl groups include cyclopropyl, cyclobutyl, cyclopentyl, cyclohexyl, octahydropentalenyl, spiro[3.3]heptanyl, and the like. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular examples are cyclopropyl and cyclobutyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, and hydroxycylopropylmethyl. Particular example is cycloproylmethyl.

The term "halogen", "halide" and "halo" are used interchangeably herein and denote fluoro, chloro, bromo or iodo. Particular halogens are fluoro and chloro.

The term "haloalkyl" denotes a $C_{1-6}$-alkyl group wherein at least one of the hydrogen atoms of the $C_{1-6}$-alkyl group has been replaced by the same or different halogen atoms. Particular examples are fluoromethyl, difluoromethyl and trifluoromethyl.

The term "haloalkoxy" denotes a $C_{1-6}$-alkoxy group wherein at least one of the hydrogen atoms of the $C_{1-6}$-alkoxy group has been replaced by the same or different halogen atoms. Examples of haloalkoxy are difluoromethoxy, trifluoromethoxy, difluoroethoxy and trifluoroethoxy. Particular examples are difluoromethoxy and trifluoromethoxy. Preferred example is trifluoromethoxy.

The terms "heteroaryl", alone or in combination with other groups, refers to a monovalent aromatic containing from one to four ring heteroatoms selected from N, O, or S, the remaining ring atoms being C. Preferably, the monocyclic heteroaryl bears one or two heteroatoms. 5- or 6-membered heteroaryl are preferred. Examples for heteroaryl moieties include but are not limited to pyridyl, pyrazinyl, and thienyl. Heteroaryl may be unsubstituted or substituted as described herein.

The term "heteroarylalkyl", denotes an alkyl group wherein one of the hydrogen atoms of the alkyl group has been replaced by a heteroaryl group. Example of a heteroarylalkyl group includes pyridinylalkyl.

The term "heterocycle" denotes a monovalent saturated or partly unsaturated mono- or bicyclic ring system of 3 to 10 ring atoms, or 3 to 8 ring atoms, comprising 1, 2, or 3 ring heteroatoms selected from N, O and S, the remaining ring atoms being carbon. Examples for monocyclic saturated heterocycle rings are oxetanyl, azetidinyl, pyrrolidinyl, tetrahydrofuranyl, pyrazolidinyl, imidazolidinyl, oxazolidinyl, isoxazolidinyl, thiazolidinyl, piperidinyl, tetrahydropyranyl, tetrahydrothiopyranyl, or piperazinyl. Examples for partly unsaturated heterocycle rings are dihydrofuryl, imidazolinyl, dihydro-oxazolyl, tetrahydro-pyridinyl, or dihydropyranyl. Particular examples of a heterocycle ring are octahydroindolizinyl, Azabicyclo[2.2.1]heptan-6-yl, azabicyclo[3.2.1]octan-2-yl, piperidinyl or furanyl. Preferred examples are furanyl and piperidinyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "nitrile" or "cyano" denotes a —C≡N group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine. In addition these salts may be prepared from addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula Ib can also be present in the form of zwitterions. Particularly preferred pharmaceutically acceptable salts of compounds of formula Ib are the salts formed with formic acid, acetic acid, trifluoroacetic acid, and the salts formed with hydrochloric acid yielding a hydrochloride, dihydrochloride or trihydrochloride salt.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula Ib can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula Ib as described herein and pharmaceutically acceptable salts or esters thereof, in particular compounds according to formula Ib as described herein and pharmaceutically acceptable salts thereof, more particularly compounds according to formula Ib as described herein.

An embodiment of the present invention provides compounds according to formula Ib as described herein, wherein $R^1$ is acetyl, $SF_5$, halo, haloalkyl, haloalkoxy or nitrile.

An embodiment of the present invention provides compounds according to formula Ib as described herein, wherein $R^1$ is halo, haloalkyl or haloalkoxy.

An embodiment of the present invention provides compounds according to formula Ib as described herein, wherein $R^1$ is haloalkoxy.

An embodiment of the present invention provides compounds according to formula Ib as described herein, wherein $R^1$ is H, halo, alkyl, haloalkyl, or haloalkoxy.

An embodiment of the present invention provides compounds according to formula Ib as described herein, wherein $R^1$ is Cl, $OCF_3$, $CF_3$, or $CH_3$.

An embodiment of the present invention provides compounds according to formula Ib as described herein, wherein $R^1$ is Cl or $CF_3$.

An embodiment of the present invention provides compounds according to formula Ib as described herein, wherein $R^1$ is $CF_3$.

An embodiment of the present invention provides compounds according to formula Ib as described herein, wherein $R^2$ is H, halo, alkyl, haloalkyl, or cycloalkyl wherein cycloalkyl is optionally substituted with halo;

An embodiment of the present invention provides compounds according to formula Ib as described herein, wherein $R^2$ is H, halo, alkyl or haloalkyl.

An embodiment of the present invention provides compounds according to formula Ib as described herein, wherein $R^2$ is H or alkyl.

An embodiment of the present invention provides compounds according to formula Ib as described herein, wherein $R^2$ is H.

An embodiment of the present invention provides compounds according to formula Ib as described herein, wherein $R^3$ is H, alkyl, haloalkyl, or cycloalkyl wherein cycloalkyl is optionally substituted with halo;

An embodiment of the present invention provides compounds according to formula Ib as described herein, wherein $R^3$ is H, alkyl or haloalkyl.

An embodiment of the present invention provides compounds according to formula Ib as described herein, wherein $R^3$ is alkyl.

An embodiment of the present invention provides compounds according to formula Ib as described herein, wherein $R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with OH:

An embodiment of the present invention provides compounds according to formula Ib as described herein, wherein $R^4$ is a heterocycle ring optionally substituted with alkyl.

An embodiment of the present invention provides compounds according to formula Ib as described herein, wherein $R^4$ is a pyrrolidine, furan, piperidine, or pyran ring substituted with alkyl.

An embodiment of the present invention provides compounds according to formula Ib as described herein, wherein $R^4$ is a pyrolidine or piperidine ring substituted with alkyl.

An embodiment of the present invention provides compounds according to formula Ib as described herein, wherein $R^4$ is a piperidine ring substituted with alkyl.

An embodiment of the present invention provides compound according to formula Ib as described herein, wherein $R^4$ is tert-butylpiperidine.

An embodiment of the present invention provides compounds according to formula Ib as described herein, wherein $R^4$ is ethylpiperidine.

An embodiment of the present invention provides compounds according to formula Ib as described herein, wherein Z is —NH—.

An embodiment of the present invention provides compounds according to formula Ib as described herein, wherein $R^5$ is H or $R^1$ and $R^5$, and the atoms to which they are bonded, form either an 4-6 membered heterocycle ring comprising a single O heteroatom or $R^1$ and $R^5$, and the atoms to which they are bonded, form a 3-6 membered cycloalkyl ring.

An embodiment of the present invention provides compounds according to formula Ib as described herein, wherein $R^5$ is H or $R^1$ and $R^5$, and the atoms to which they are bonded, form a 5 membered heterocycle ring comprising a single O atom.

An embodiment of the present invention provides compounds according to formula Ib as described herein, wherein $R^5$ is H.

An embodiment of the present invention provides compounds according to formula Ib as described herein, wherein $R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with one or two substituents independently selected from halo or alkyl.

An embodiment of the present invention provides compounds according to formula Ib as described herein, wherein $R^1$ and $R^5$, and the atoms to which they are bonded, form either a 4-6 membered heterocycle ring comprising a single O heteroatom, or $R^1$ and $R^5$, and the atoms to which they are bonded, form a 3-6 membered cycloalkyl ring.

An embodiment of the present invention provides compounds according to formula Ib as described herein, wherein $R^1$ and $R^5$, and the atoms to which they are bonded, form a 5 membered heterocycle ring comprising a single O heteroatom.

An embodiment of the present invention provides compounds according to formula Ib as described herein, wherein $R^1$ is acetyl, $SF_5$, halo, haloalkyl, haloalkoxy or nitrile;

$R^5$ is H;

or $R^1$ and $R^5$, and the atoms to which they are bonded, form either an 4-6 membered heterocycle ring comprising a single O heteroatom or $R^1$ and $R^5$, and the atoms to which they are bonded, form a 3-6 membered cycloalkyl ring $R^2$ is H or alkyl;

$R^3$ is H, alkyl or cycloalkyl;

Z is —NH—;

$R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with OH;

and pharmaceutically acceptable salts.

An embodiment of the present invention provides compounds according to formula Ib as described herein, wherein $R^1$ is acetyl, $SF_5$, halo, haloalkyl, haloalkoxy or nitrile;

$R^5$ is H;

or $R^1$ and $R^5$, and the atoms to which they are bonded, form a 5 membered heterocycle ring comprising a single O $R^2$ is H or alkyl;

$R^3$ is H, alkyl or cycloalkyl;

Z is —NH—;

$R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with OH;

and pharmaceutically acceptable salts.

An embodiment of the present invention provides compounds according to formula Ib as described herein, wherein $R^1$ is halo, haloalkyl, or haloalkoxy;

$R^5$ is H;

or $R^1$ and $R^5$, and the atoms to which they are bonded, form a 5 membered heterocycle ring comprising a single O $R^2$ is H;

$R^3$ is alkyl;

Z is —NH—;

$R^4$ is a piperidyl ring optionally substituted with alkyl;

and pharmaceutically acceptable salts.

An embodiment of the present invention provides compounds according to formula Ib as described herein, wherein $R^1$ is haloalkoxy;

$R^5$ is H;

$R^2$ is H;

$R^3$ is alkyl;

Z is —NH—;

$R^4$ is a piperidyl ring optionally substituted with alkyl;

and pharmaceutically acceptable salts.

An embodiment of the present invention provides compounds according to formula Ib as described herein, wherein $R^1$ is H, halo, alkyl, haloalkyl, haloalkoxy or nitrile;

$R^5$ is H;

or $R^1$ and $R^5$, and the atoms to which they are bonded, form either an 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring with one or two substituents independently selected from halo or alkyl;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 2 substituents independently selected from halo, alkyl, haloalkyl, hydroxyalkyl, —OH, oxo, —$CO_2$H, or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl may have up to three substituents independently selected from alkyl, halo, haloalkyl and —OH;

and pharmaceutically acceptable salts thereof.

An embodiment of the present invention provides compounds according to formula Ib as described herein, wherein $R^1$ and $R^5$, and the atoms to which they are bonded, form either a 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl optionally substituted with one or two substituents independently selected from halo or alkyl;

$R^2$ is H;

$R^3$ is methyl;

Z is —NH—;

$R^4$ is a piperidine ring substituted with alkyl;

and pharmaceutically acceptable salts thereof.

An embodiment of the present invention provides compounds according to formula Ib as described herein, wherein $R^1$ and $R^5$, and the atoms to which they are bonded, form either a 4-6 membered heterocycle ring comprising a single O heteroatom, or $R^1$ and $R^5$, and the atoms to which they are bonded, form a 4-6 membered cycloalkyl ring:

$R^2$ is H;

$R^3$ is methyl;

Z is —NH—;

$R^4$ is a piperidine ring substituted with alkyl;

and pharmaceutically acceptable salts thereof.

Particular examples of compounds of formula Ib as described herein are selected from 6-((1-Ethylpiperidin-3-yl)amino)-3-(2-hydroxy-4-(trifluoromethyl)phenyl)-4-methyl-1,2,4-triazin-5(4H)-one;

6-[[(3R)-1-Ethyl-3-piperidyl]amino]-3-(4-hydroxy-2,3-dihydrobenzofuran-5-yl)-4-methyl-1,2,4-triazin-5-one;

3-[2-Hydroxy-4-(trifluoromethyl)phenyl]-4-methyl-6-[[(3R)-3-piperidyl]amino]-1,2,4-triazin-5-one;

3-[2-Hydroxy-4-(trifluoromethyl)phenyl]-4-methyl-6-[(8-methyl-8-azabicyclo[3.2.1]octan-2-yl)amino]-1,2,4-triazin-5-one;

(R)-6-((1-(Cyclopropylmethyl)piperidin-3-yl)amino)-3-(2-hydroxy-4-(trifluoromethyl)phenyl)-4-methyl-1,2,4-triazin-5(4H)-one;

(R)-3-(2-Hydroxy-4-(trifluoromethyl)phenyl)-4-methyl-6-((1-methylpiperidin-3-yl)amino)-1,2,4-triazin-5(4H)-one;

6-(1,2,3,5,6,7,8,8a-Octahydroindolizin-8-ylamino)-3-[2-hydroxy-4-(trifluoromethyl)phenyl]-4-methyl-1,2,4-triazin-5-one;

3-[2-Hydroxy-4-(trifluoromethyl)phenyl]-4-methyl-6-[[(3R)-1-propyl-3-piperidyl]amino]-1,2,4-triazin-5-one;

3-[2-Hydroxy-4-(trifluoromethyl)phenyl]-4-methyl-6-[(1,5,5-trimethyl-3-piperidyl)amino]-1,2,4-triazin-5-one;

(R)-6-((1-Cyclopropylpiperidin-3-yl)amino)-3-(2-hydroxy-4-(trifluoromethyl)phenyl)-4-methyl-1,2,4-triazin-5(4H)-one;

6-(((1S,3S)-3-Hydroxy-3-methylcyclobutyl)amino)-3-(2-hydroxy-4-(trifluoromethyl)phenyl)-4-methyl-1,2,4-triazin-5(4H)-one;

6-[(1-tert-Butyl-3-piperidyl)amino]-3-[2-hydroxy-4-(trifluoromethyl)phenyl]-4-methyl-1,2,4-triazin-5-one;

6-(2-Azabicyclo[2.2.1]heptan-6-ylamino)-3-[2-hydroxy-4-(trifluoromethyl)phenyl]-4-methyl-1,2,4-triazin-5-one;

6-[[(3R,5S)-1-Ethyl-5-methyl-3-piperidyl]amino]-3-[2-hydroxy-4-(trifluoromethyl)phenyl]-4-methyl-1,2,4-triazin-5-one;

6-[[(3R,5R)-1-Ethyl-5-methyl-3-piperidyl]amino]-3-[2-hydroxy-4-(trifluoromethyl)phenyl]-4-methyl-1,2,4-triazin-5-one;

6-[[(5S)-5-fluoro-1-methyl-3-piperidyl]amino]-3-[2-hydroxy-4-(trifluoromethyl)phenyl]-4-methyl-1,2,4-triazin-5-one;

6-[[(3R)-6,6-Dimethyl-3-piperidyl]amino]-3-[2-hydroxy-4-(trifluoromethyl)phenyl]-4-methyl-1,2,4-triazin-5-one;

6-[(3-Hydroxyphenyl)methylamino]-3-[2-hydroxy-4-(trifluoromethyl)phenyl]-4-methyl-1,2,4-triazin-5-one;

6-[[(3R)-1-Ethyl-3-piperidyl]amino]-3-[2-hydroxy-4-(trifluoromethyl)phenyl]-4-methyl-1,2,4-triazin-5-one;

4-Cyclopropyl-6-[[(3R)-1-ethyl-3-piperidyl]amino]-3-[2-hydroxy-4-(trifluoromethyl)phenyl]-1,2,4-triazin-5-one;

6-[[(3R)-1-Ethyl-3-piperidyl]amino]-3-(4-fluoro-2-hydroxy-phenyl)-4-methyl-1,2,4-triazin-5-one;

4-Ethyl-6-[[(3R)-1-ethyl-3-piperidyl]amino]-3-[2-hydroxy-4-(trifluoromethyl)phenyl]-1,2,4-triazin-5-one;

3-[4-(Difluoromethoxy)-2-hydroxy-phenyl]-6-[[(3R)-1-ethyl-3-piperidyl]amino]-4-methyl-1,2,4-triazin-5-one;

3-[4-(1,1-Difluoroethyl)-2-hydroxy-phenyl]-6-[[(3R)-1-ethyl-3-piperidyl]amino]-4-methyl-1,2,4-triazin-5-one;

3-(4-Acetyl-2-hydroxy-phenyl)-6-[[(3R)-1-ethyl-3-piperidyl]amino]-4-methyl-1,2,4-triazin-5-one;

3-[2-hydroxy-4-(trifluoromethyl)phenyl]-4-methyl-6-[[(3R)-1-methyl-3-piperidyl]amino]-1,2,4-triazin-5-one;

6-[[(3R)-1-Ethyl-3-piperidyl]amino]-3-[2-hydroxy-4-(trifluoromethoxy)phenyl]-4-methyl-1,2,4-triazin-5-one;

6-[[(3R)-1-Ethyl-3-piperidyl]amino]-3-[2-hydroxy-6-methyl-4-(trifluoromethyl)phenyl]-4-methyl-1,2,4-triazin-5-one;

(M or P)-6-[[(3R)-1-ethyl-3-piperidyl]amino]-3-[2-hydroxy-6-methyl-4-(trifluoromethyl)phenyl]-4-methyl-1,2,4-triazin-5-one;

(P or M)-6-[[(3R)-1-ethyl-3-piperidyl]amino]-3-[2-hydroxy-6-methyl-4-(trifluoromethyl)phenyl]-4-methyl-1,2,4-triazin-5-one;

6-[[(3R)-1-Ethyl-3-piperidyl]amino]-3-[2-hydroxy-4-(pentafluoro-λ6-sulfanyl)phenyl]-4-methyl-1,2,4-triazin-5-one;

4-[6-[[(3R)-1-Ethyl-3-piperidyl]amino]-4-methyl-5-oxo-1,2,4-triazin-3-yl]-3-hydroxy-benzonitrile;

3-(4-Chloro-2-hydroxy-phenyl)-6-[[(3R)-1-ethyl-3-piperidyl]amino]-4-methyl-1,2,4-triazin-5-one;

3-[2-Hydroxy-4-(trifluoromethoxy)phenyl]-4-methyl-6-[[(3R)-1-methyl-3-piperidyl]amino]-1,2,4-triazin-5-one;

6-[[(3R)-1-Ethyl-3-piperidyl]amino]-3-[2-hydroxy-4-(trifluoromethyl)phenyl]-4H-1,2,4-triazin-5-one;

6-[[(3R,5S)-1-ethyl-5-fluoro-3-piperidyl]amino]-3-[2-hydroxy-4-(trifluoromethyl)phenyl]-4H-1,2,4-triazin-5-one;

and pharmaceutically acceptable salts thereof.

Preferred examples of compounds of formula Ib as described herein are selected from 6-[[(3R)-1-Ethyl-3-piperidyl]amino]-3-(4-hydroxy-2,3-dihydrobenzofuran-5-yl)-4-methyl-1,2,4-triazin-5-one;

(R)-3-(2-Hydroxy-4-(trifluoromethyl)phenyl)-4-methyl-6-((1-methylpiperidin-3-yl)amino)-1,2,4-triazin-5(4H)-one;

6-[[(3R)-1-Ethyl-3-piperidyl]amino]-3-[2-hydroxy-4-(trifluoromethyl)phenyl]-4-methyl-1,2,4-triazin-5-one;

3-[4-(Difluoromethoxy)-2-hydroxy-phenyl]-6-[[(3R)-1-ethyl-3-piperidyl]amino]-4-methyl-1,2,4-triazin-5-one;

6-[[(3R)-1-Ethyl-3-piperidyl]amino]-3-[2-hydroxy-4-(trifluoromethoxy)phenyl]-4-methyl-1,2,4-triazin-5-one;

3-(4-Chloro-2-hydroxy-phenyl)-6-[[(3R)-1-ethyl-3-piperidyl]amino]-4-methyl-1,2,4-triazin-5-one;

3-[2-Hydroxy-4-(trifluoromethoxy)phenyl]-4-methyl-6-[[(3R)-1-methyl-3-piperidyl]amino]-1,2,4-triazin-5-one;

and pharmaceutically acceptable salts thereof.

The most preferred example of a compound of formula Ib as described herein is 6-[[(3R)-1-Ethyl-3-piperidyl]amino]-3-[2-hydroxy-4-(trifluoromethoxy)phenyl]-4-methyl-1,2,4-triazin-5-one, and pharmaceutically acceptable salts thereof.

Other examples of formula Ib as described herein include either 6-((1-ethylpiperidin-3-yl)amino)-3-(2-hydroxy-4-(trifluoromethyl)phenyl)-4-methyl-1,2,4-triazin-5(4H)-one or 6-[[(3R)-1-Ethyl-3-piperidyl]amino]-3-(4-hydroxy-2,3-dihydrobenzofuran-5-yl)-4-methyl-1,2,4-triazin-5-one, or pharmaceutical acceptable salts thereof.

An embodiment of the present invention provides compounds according to formula I, wherein the compound of formula I is a compound of formula Ib

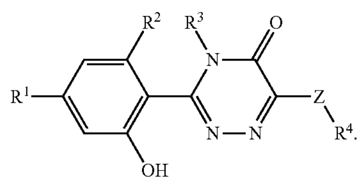

I

Also an embodiment of the present invention provides compounds of formula I wherein $R^1$ is H, halo, alkyl, haloalkyl, haloalkoxy, or nitrile;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 2 substituents independently selected from halo, alkyl, haloalkyl, hydroxyalkyl, —OH, oxo, —$CO_2$H, or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl may have up to three substituents independently selected from alkyl, halo, haloalkyl and —OH;

and pharmaceutically acceptable salts.

An embodiment of the present invention provides compounds of formula I wherein $R^1$ is H, halo, alkyl, haloalkyl, or haloalkoxy;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 2 substituents independently selected from halo, alkyl, haloalkyl, hydroxyalkyl, —OH, oxo, —$CO_2$H, or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl may have up to three substituents independently selected from alkyl, halo, haloalkyl and —OH;

and pharmaceutically acceptable salts.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Also an embodiment of the present invention provides compounds according to formula I as described herein and pharmaceutically acceptable salts or esters thereof, in particular compounds according to formula I as described herein and pharmaceutically acceptable salts thereof, more particularly compounds according to formula I as described herein.

An embodiment of the present invention provides compounds according to formula I as described herein, wherein $R^1$ is H, halo, alkyl, haloalkyl, or haloalkoxy.

An embodiment of the present invention provides compounds according to formula I as described herein, wherein $R^1$ is Cl, $OCF_3$, $CF_3$, or $CH_3$.

An embodiment of the present invention provides compounds according to formula I as described herein, wherein $R^1$ is Cl or $CF_3$.

An embodiment of the present invention provides compounds according to formula I as described herein, wherein $R^1$ is $CF_3$.

An embodiment of the present invention provides compounds according to formula I as described herein, wherein $R^2$ is H, halo, alkyl, haloalkyl, or cycloalkyl wherein cycloalkyl is optionally substituted with halo;

An embodiment of the present invention provides compounds according to formula I as described herein, wherein $R^2$ is H, halo, alkyl or haloalkyl.

An embodiment of the present invention provides compounds according to formula I as described herein, wherein $R^2$ is H.

An embodiment of the present invention provides compounds according to formula I as described herein, wherein $R^3$ is H, alkyl, haloalkyl, or cycloalkyl wherein cycloalkyl is optionally substituted with halo;

An embodiment of the present invention provides compounds according to formula I as described herein, wherein $R^3$ is H, alkyl or haloalkyl.

An embodiment of the present invention provides compounds according to formula I as described herein, wherein $R^3$ is alkyl.

An embodiment of the present invention provides compounds according to formula I as described herein, wherein $R^4$ is a heterocycle ring optionally substituted with alkyl.

An embodiment of the present invention provides compounds according to formula I as described herein, wherein $R^4$ is a pyrrolidine, furan, piperidine, or pyran ring substituted with alkyl.

An embodiment of the present invention provides compounds according to formula I as described herein, wherein $R^4$ is a pyrolidine or piperidine ring substituted with alkyl.

An embodiment of the present invention provides compounds according to formula I as described herein, wherein $R^4$ is a piperidine ring substituted with alkyl.

An embodiment of the present invention provides compound according to formula I as described herein, wherein $R^4$ is tert-butylpiperidine.

An embodiment of the present invention provides compounds according to formula I as described herein, wherein $R^4$ is ethylpiperidine.

An embodiment of the present invention provides compounds according to formula I as described herein, wherein Z is —NH—.

An embodiment of the present invention provides compounds according to formula I as described herein, wherein $R^1$ is Cl, $OCF_3$, alkyl or haloalkyl;

$R^2$ is H, halo, alkyl, haloalkyl or cycloalkyl optionally substituted with F;

$R^3$ is H, alkyl, haloalkyl, or cycloalkyl optionally substituted with F;

Z is —O—, or —NH—;

$R^4$ is a heterocycle ring optionally substituted with 1 to 2 substituents independently selected from halo, alkyl, haloalkyl, hydroxyalkyl, —OH, oxo, —$CO_2$H, or cycloalkyl optionally substituted with halo; or $R^4$ is a cycloalkyl optionally substituted with 1 to 3 substituents independently selected from alkyl, halo, haloalkyl and —OH.

An embodiment of the present invention provides compounds according to formula I as described herein, wherein $R^1$ is Cl, $CH_3$, $OCF_3$, or $CF_3$;

$R^2$ is H, halo, alkyl, or haloalkyl;

$R^3$ is H, alkyl or haloalkyl;

Z is —O—, or —NH—;

$R^4$ is a heterocycle ring comprising 1 heteroatom, optionally substituted with 1 to 2 substituents independently selected from halo, alkyl, haloalkyl, hydroxyalkyl, —OH, oxo, —$CO_2$H, or cycloalkyl optionally substituted with halo; or $R^4$ is a cycloalkyl optionally substituted with 1 to 3 substituents independently selected from alkyl, halo, haloalkyl and —OH.

An embodiment of the present invention provides compounds according to formula I as described herein, wherein $R^1$ is Cl, $CH_3$, $OCF_3$, or $CF_3$;

$R^2$ is H, halo, alkyl, or haloalkyl;

$R^3$ is H, alkyl or haloalkyl;

Z is —O—, or —NH—;

$R^4$ is a heterocycle ring comprising 1 heteroatom, optionally substituted with 1 to 2 substituents independently selected from halo, alkyl, or haloalkyl.

An embodiment of the present invention provides compounds according to formula I as described herein, wherein $R^1$ is Cl or $CF_3$;

$R^2$ is H, halo, alkyl, or haloalkyl;

$R^3$ is H, alkyl or haloalkyl;

Z is —NH—;

$R^4$ is a heterocycle ring comprising 1 heteroatom, optionally substituted with 1 to 2 substituents independently selected from halo, alkyl, or haloalkyl.

An embodiment of the present invention provides compounds according to formula I as described herein, wherein $R^1$ is Cl or $CF_3$;

$R^2$ is H;

$R^3$ is $CH_3$;

Z is —NH—;

$R^4$ is a piperidine ring substituted with alkyl.

An embodiment of the present invention provides compounds according to formula I as described herein, wherein $R^1$ is $CF_3$;

$R^2$ is H;

$R^3$ is $CH_3$;

Z is —NH—;

$R^4$ is a piperidine ring substituted with alkyl.

A particular example of compounds of formula I as described herein is 6-((1-ethylpiperidin-3-yl)amino)-3-(2-hydroxy-4-(trifluoromethyl)phenyl)-4-methyl-1,2,4-triazin-5(4H)-one, or pharmaceutically acceptable salts thereof.

Processes for the manufacture of compounds of formula I as described herein are an object of the invention. The synthesis of the compound of formula I can, for example, be accomplished according to scheme 1.

The invention also relates to a compound according to the invention when manufactured according to a process of the invention.

General Synthesis Scheme for the Triazinone Compounds:

The compounds of formula I may be prepared in accordance with the process variant described above and with the following scheme 1. The starting materials are commercially available or may be prepared in accordance with known methods.

Scheme 1

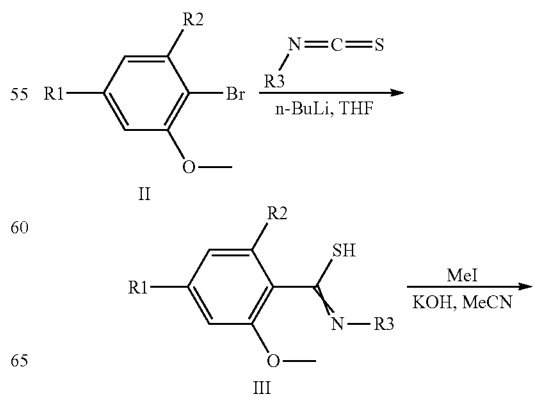

II

III

-continued

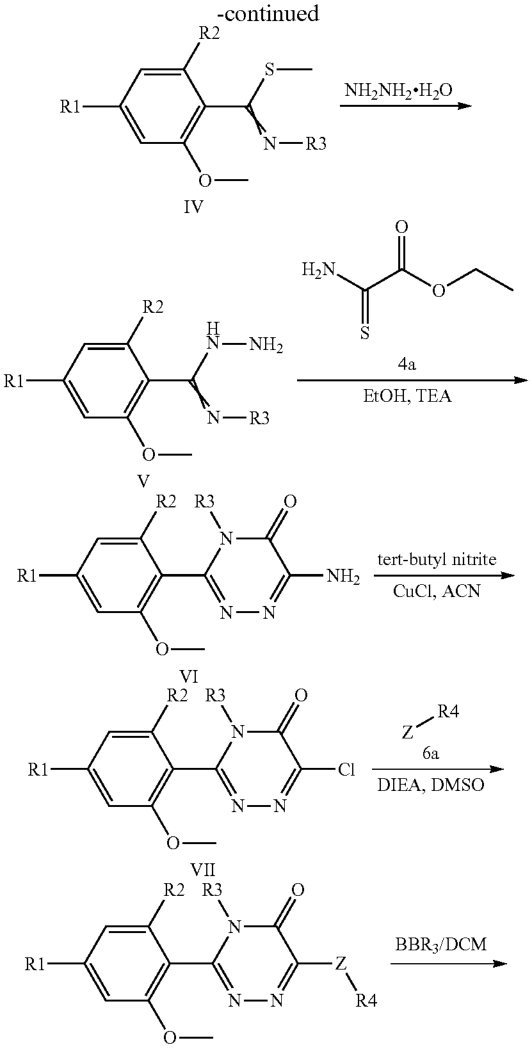

IV
V
VI
VII
VIII

-continued

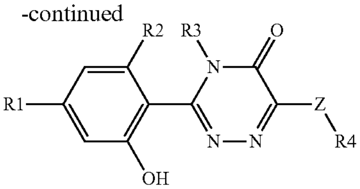

I

Compounds of general formula I e.g. Example 1 can be synthesized according to the synthesis route outlined in Scheme 1. Starting from commercially available arylbromides II such as 1-bromo-2-methoxy-4-(trifluoromethyl) benzene (CAS: 402-07-3) compounds of general formula III were obtained after reaction with methyl isothiocyanate in the presence of n-BuLi in dry THF. Afterwards, alkylation using methyl iodide, methyl bromide or other suitable alkylation reagents in the presence of a base such as potassium hydroxide yielded IV. Subsequent reaction with hydrazine hydrate gave intermediates of general formula V followed by cyclisation with ethyl thiooxamate and a base such as trietylamine to the corresponding triazinone VI. Afterwards, Sandmeyer reaction using tert-butyl nitrite and in the presence of Cu(I)Cl yielded VII. Diazotization can also be carried out using sodium nitrite or equivalent reagents forming a diazonium intermediate, followed by the addition of copper chloride. Subsequently, nucleophilic aromatic substitution using amines according to general formula 6a, and a base preferably N,N-diisopropylethylamine or triethylamine in solvents as DMSO, DMF or ether such as THE at elevated temperatures gave VIII. In a final step, the aryl methyl ether group was cleaved with the well-known boron tribromide ($BBr_3$) in dichloromethane delivering the compounds of general formula I, e.g. Example 1. Final deprotection can also by achieved using benzenethiol, potassium carbonate or related bases in solvents as NMP at elevated temperatures.

Scheme 2

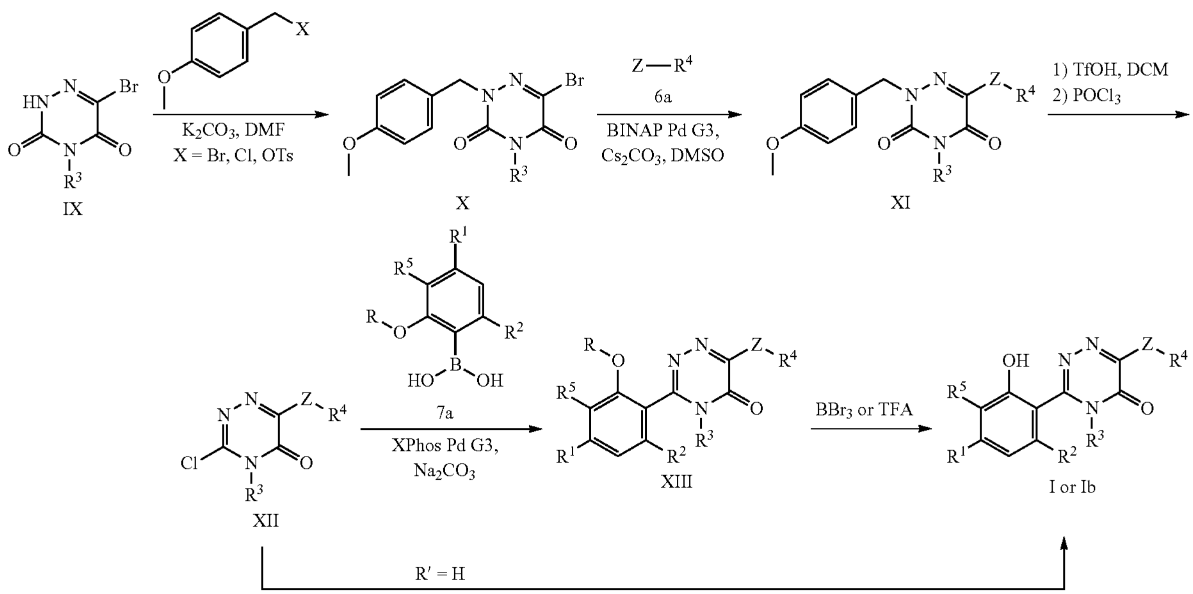

IX
X
XI
XII
XIII
I or Ib

Alternatively, compounds of formula I or Ib can also be synthesized following to an alternative synthetic route depicted in scheme 2. Starting from e.g. 6-bromo-4-methyl-2H-1,2,4-triazine-3,5-dione (IX; CAS: 15870-75-4), PMB protection was done by reaction of 4-methoxybenzyl chloride in the presence of a base e.g. an alkali carbonate or alkali phosphate, preferably such as potassium carbonate in DMF. Alternatively, other alkylation reagents such as bromides, mesylates, tosylates in the presence of other bases such as cesium carbonate, DIPEA or triethylamine in solvents such as THF or DMSO can be performed or any other standard procedures known to the skilled person of the art to afford intermediates of general formula X. Subsequently, palladium catalyzed amination reactions such as Buchwald using a hetaryl bromide with preferably (3R)-1-ethylpiperidin-3-amine, (3R)-1-methylpiperidin-3-amine or any amine according to the claims in the presence of a catalyst such as BINAP Pd G3 using e.g. cesium carbonate as a base. As solvent DMSO was used but the reaction can also be done in DMF. THF or other solvents to yield intermediates of general formula XI. Alternatively, XI can be obtained by nucleophilic aromatic substitutions reactions known to the skilled person. Afterwards, PMB deprotection was achieved by addition of trifluoromethanesulfonic acid in DCM at room temperature. PMB deprotection could also be accomplished using hydrogenation in the presence of commercial palladium-on-carbon catalysts such as Pd/C in a solvent as methanol or ethanol. Chlorination by addition of $POCl_3$ and heating the reaction yielded intermediates of general formula XII. Finally, the left hand side was introduced by Suzuki-Miyaura cross coupling, well known to the person skilled in the art, in the presence of a palladium catalyst as XPhos Pd G3 and a boronic acid or boronic pinacol ester 7a according to standard conditions well known to the skilled person. In case of aryl methyl ether, the final product was obtained by addition of boron tribromide ($BBr_3$) in dichloromethane delivering the compounds of general formula I or Ib, in case of SEM the final compounds were obtained after reaction with TFA. Generally other phenol protecting group modifications can be applied, known to the skilled person of the art. Specific examples are described in more detail for each exemplified compound below.

The invention thus relates to a compound according to the invention when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula Ib may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula Ib is formulated in an acetate buffer, at pH 5. In another embodiment, the compound of formula Ib is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The compounds of formula Ib and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

The compounds of formula I and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

An embodiment of the present invention is a compound according to formula Ib as described herein for use as a therapeutically active substance.

An embodiment of the present invention is a compound according to formula Ib as described herein for use in the treatment or prevention of a disease, disorder or condition, wherein the disease, disorder or condition is responsive to NLRP3 inhibition.

An embodiment of the present invention is a compound according to formula Ib as described herein for the treatment or prophylaxis of a disease, disorder or condition, wherein the disorder or condition is responsive to NLRP3 inhibition.

An embodiment of the present invention is a compound according to formula I as described herein for use as a therapeutically active substance.

An embodiment of the present invention is a compound according to formula I as described herein for use in the treatment or prevention of a disease, disorder or condition, wherein the disease, disorder or condition is responsive to NLRP3 inhibition.

An embodiment of the present invention is a compound according to formula I as described herein for the treatment or prophylaxis of a disease, disorder or condition, wherein the disorder or condition is responsive to NLRP3 inhibition.

As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481: 278-286, 2012).

In one embodiment, the disease, disorder or condition is selected from:

(i) inflammation;
(ii) an auto-immune disease;
(iii) cancer;
(iv) an infection;
(v) a central nervous system disease;

(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3

In another embodiment, the disease, disorder or condition is selected from:

(i) cancer;
(ii) an infection;
(iii) a central nervous system disease;
(iv) a cardiovascular disease;
(v) a liver disease;
(vi) an ocular disease; or
(vii) a skin disease.

In a further typical embodiment of the invention, the disease, disorder or condition is inflammation. Examples of inflammation that may be treated or prevented include inflammatory responses occurring in connection with, or as a result of:

(i) a skin condition such as contact hypersensitivity, bullous pemphigoid, sunburn, psoriasis, atopical dermatitis, contact dermatitis, allergic contact dermatitis, seborrhoeic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), colitis, gastric ulcer, Coeliac disease, proctitis, pancreatitis, eosinophilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including eosinophilic, bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, volcanic ash induced inflammation, adult respiratory distress syndrome, hypersensitivity pneumonitis, or idiopathic interstitial pneumonia;

(vi) a vascular condition such as atherosclerosis, Behcet's disease, vasculitides, or Wegener's granulomatosis;

(vii) an autoimmune condition such as systemic lupus erythematosus, Sjögren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis* (including *Mycobacterium tuberculosis* and HIV co-infection), *Mycobacterium avium intracellulare, Pneumocystis carinii* pneumonia, orchitis/epididymitis, *Legionella*, Lyme disease, influenza A, Epstein-Barr virus infection, viral encephalitis/aseptic meningitis, or pelvic inflammatory disease;

(xi) a renal condition such as mesangial proliferative glomerulonephritis, nephrotic syndrome, nephritis, glomerular nephritis, obesity related glomerulopathy, acute renal failure, acute kidney injury, uremia, nephritic syndrome, kidney fibrosis including chronic crystal nephropathy, or renal hypertension;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH), primary biliary cirrhosis, fulminant hepatitis, liver fibrosis, or liver failure;

(xv) a cancer, including those cancers listed above;

(xvi) a burn, wound, trauma, haemorrhage or stroke;

(xvii) radiation exposure;

(xviii) a metabolic disease such as type 2 diabetes (T2D), atherosclerosis, obesity, gout or pseudo-gout: and/or (xix) pain such as inflammatory hyperalgesia, pelvic pain, allodynia, neuropathic pain, or cancer-induced bone pain.

An embodiment of the present invention is a compound according to formula Ib as described herein for the treatment or prophylaxis of a disease, disorder or condition selected from:

(i) inflammation;

(ii) an auto-immune disease;

(iii) cancer;

(iv) an infection;

(v) a central nervous system disease;

(vi) a metabolic disease;

(vii) a cardiovascular disease;

(viii) a respiratory disease;

(ix) a liver disease;

(x) a renal disease;

(xi) an ocular disease;

(xii) a skin disease;

(xiii) a lymphatic condition;

(xiv) a psychological disorder, (xv) graft versus host disease;

(xvi) allodynia;

(xvii) a condition associated with diabetes; and (xviii) any disease where an individual has been determined to carry a germline or somatic non-silent mutation in NLRP3.

An embodiment of the present invention is the use of a compound according to formula Ib as described herein in the treatment or prophylaxis of a disease, disorder or condition selected from Alzheimer's disease and Parkinson's disease.

An embodiment of the present invention is the use a compound according to formula Ib as described herein for use in the treatment or prophylaxis of a disease, disorder or condition selected from Asthma or COPD.

An embodiment of the present invention is the use a compound according to formula Ib as described herein for use in the treatment or prophylaxis of a disease, disorder or condition selected from inflammatory bowel disease (including Crohn's disease and ulcerative colitis).

An embodiment of the present invention is a compound according to formula Ib as described herein for the treatment or prophylaxis of a disease, disorder or condition selected from Alzheimer's disease and Parkinson's disease.

An embodiment of the present invention is a compound according to formula Ib as described herein for the treatment or prophylaxis of a disease, disorder or condition selected from Asthma or COPD.

An embodiment of the present invention is a compound according to formula Ib as described herein for the treatment or prophylaxis of a disease, disorder or condition selected from inflammatory bowel disease (including Crohn's disease and ulcerative colitis).

An embodiment of the present invention is the use of a compound according to formula Ib as described herein for preparation of a medicament for the treatment or prophylaxis of a disease, disorder or condition selected from Alzheimer's disease and Parkinson's disease.

An embodiment of the present invention is the use of a compound according to formula Ib as described herein for the preparation of a medicament for the treatment or prophylaxis of a disease, disorder or condition selected from Asthma or COPD.

An embodiment of the present invention is the use of a compound according to formula Ib as described herein for the preparation of a medicament for the treatment or prophylaxis of a disease, disorder or condition selected from inflammatory bowel disease (including Crohn's disease and ulcerative colitis).

An embodiment of the present invention is a method of treatment or prophylaxis of a disease, disorder or condition selected from Alzheimer's disease and Parkinson's disease, which method comprises administering an effective amount of a compound according to formula Ib as described herein.

An embodiment of the present invention is a method of treatment or prophylaxis of a disease, disorder or condition selected from Asthma or COPD, which method comprises administering an effective amount of a compound according to formula Ib as described herein.

An embodiment of the present invention is a method of treatment or prophylaxis of a disease, disorder or condition selected from inflammatory bowel disease (including Crohn's disease and ulcerative colitis), which method comprises administering an effective amount of a compound according to formula Ib as described herein.

An embodiment of the present invention relates to a method of inhibiting NLRP3, which method comprises administering an effective amount of a compound according to formula Ib as described herein.

Also an embodiment of the present invention are compounds of formula Ib as described herein, when manufactured according to any one of the described processes.

An embodiment of the present invention is a pharmaceutical composition comprising a compound according to formula Ib as described herein and a therapeutically inert carrier.

An embodiment of the present invention is a compound according to formula I as described herein for the treatment or prophylaxis of a disease, disorder or condition selected from:

(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3.

An embodiment of the present invention is the use of a compound according to formula I as described herein in the treatment or prophylaxis of a disease, disorder or condition selected from Alzheimer's disease and Parkinson's disease.

An embodiment of the present invention is the use a compound according to formula I as described herein for use in the treatment or prophylaxis of a disease, disorder or condition selected from Asthma or COPD.

An embodiment of the present invention is a compound according to formula I as described herein for the treatment or prophylaxis of a disease, disorder or condition selected from Alzheimer's disease and Parkinson's disease.

An embodiment of the present invention is a compound according to formula I as described herein for the treatment or prophylaxis of a disease, disorder or condition selected from Asthma or COPD.

An embodiment of the present invention is the use of a compound according to formula I as described herein for preparation of a medicament for the treatment or prophylaxis of a disease, disorder or condition selected from Alzheimer's disease and Parkinson's disease.

An embodiment of the present invention is the use of a compound according to formula I as described herein for the preparation of a medicament for the treatment or prophylaxis of a disease, disorder or condition selected from Asthma or COPD.

An embodiment of the present invention is a method of treatment or prophylaxis of a disease, disorder or condition selected from Alzheimer's disease and Parkinson's disease, which method comprises administering an effective amount of a compound according to formula I as described herein.

An embodiment of the present invention is a method of treatment or prophylaxis of a disease, disorder or condition selected from Asthma or COPD, which method comprises administering an effective amount of a compound according to formula I as described herein.

An embodiment of the present invention relates to a method of inhibiting NLRP3, which method comprises administering an effective amount of a compound according to formula I as described herein.

Also an embodiment of the present invention are compounds of formula I as described herein, when manufactured according to any one of the described processes.

An embodiment of the present invention is a pharmaceutical composition comprising a compound according to formula I as described herein and a therapeutically inert carrier.

Assay Procedures

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of proinflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~$10^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C., 5% $CO_2$
4. Add 5 μl nigericin (Sigma #N7143) (FAC 5 μM) to all wells
5. Incubate for 1 hr at 37° C., 5% $CO_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

The results of the pyroptosis assay are summarised in Table 1 below as THP $IC_{50}$.

Human Whole Blood IL-1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add 10 μl nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 1 below as HWB $IC_{50}$.

hERG Screening Assay

Cells

The CHO crelox hERG cell line (ATCC reference Nr. PTA-6812, female Chinese hamster cells) was generated and validated at Roche. Ready-to-use frozen instant CHO-hERG cells were cryopreserved at Evotec (Germany) and used directly in the experiments.

Experimental Solutions

The extracellular solution contains (in mM): NaCl 150; KCl 4; CaCl2 1; MgCl2 1; HEPES 10; pH 7.2-7.4 with NaOH, osmolarity 290-330 mOsm. The internal solution contains (in mM): KCl, 10; KF, 100; NaCl, 10; HEPES, 10; EGTA, 20; pH=7.0-7.4 with KOH, osmolarity 260-300 mOsm.

Electrophysiology

The effects of a compound on hERG K+-currents parameters will be evaluated at 2 concentrations in at least 4 cells.

The hERG test is performed using automated patch clamp system SynchroPatch® 384 (Nanion Technologies GmbH, Germany). K+ currents are measured with the patch-voltage-clamp technique in the whole-cell configuration at 35-37° C.

Cells were held at a resting voltage of −80 mV and they were stimulated by a voltage pattern shown in FIG. 1 to activate hERG channels and conduct outward IKhERG current, at a stimulation frequency of 0.1 Hz (6 bpm)

Data Analysis

The amplitudes of IKhERG were recorded in each concentration of drug and they were compared to the vehicle control values (taken as 100%) to define fractional blocks. The concentration-response data were fitted with the following relationship:

$$I(C) = \frac{100}{1 + (C/IC50)^h}$$

where C is the concentration, $IC_{50}$ is the concentration producing 50% block h is the Hill coefficient.

Concentration-response curves were fitted by non-linear regression analysis using EworkBook suite (ID Business Solutions Ltd, UK). Data fit was done with the 4 Parameter Logistic Model (fit=(A+(B/(1+((x/C)^D)))), where A=0 and B=100).

TABLE 1

NLRP3 inhibitory activity

| Example No. | Structure | Name | THP-1 pyroptosis assay IC50 (nM) | Human whole blood IL-1β Assay IC50 (nM) |
|---|---|---|---|---|
| 1 | 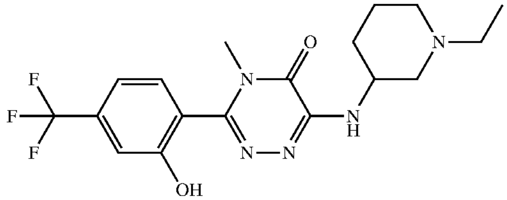 [SMILES: CCN1CCCC(Nc2nnc(-c3ccc(C(F)(F)F)cc3O)n(C)c2=O)C1] | 6-((1-Ethylpiperidin-3-yl)amino)-3-(2-hydroxy-4-(trifluoromethyl)phenyl)-4-methyl-1,2,4-triazin-5(4H)-one | 44 | 35 |
| 2 | 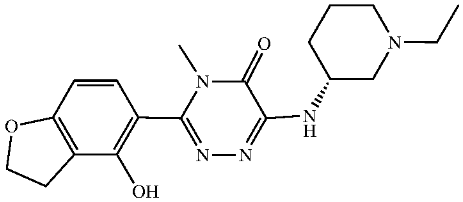 [SMILES: CCN1CCC[C@@H](Nc2nnc(-c3ccc4c(c3O)CCO4)n(C)c2=O)C1] | 6-[[(3R)-1-Ethyl-3-piperidyl]amino]-3-(4-hydroxy-2,3-dihydrobenzofuran-5-yl)-4-methyl-1,2,4-triazin-5-one | 4.3 | 16 |

TABLE 1-continued

| NLRP3 inhibitory activity | | | | |
|---|---|---|---|---|
| Example No. | Structure | Name | THP-1 pyroptosis assay IC50 (nM) | Human whole blood IL-1β Assay IC50 (nM) |
| 3 | 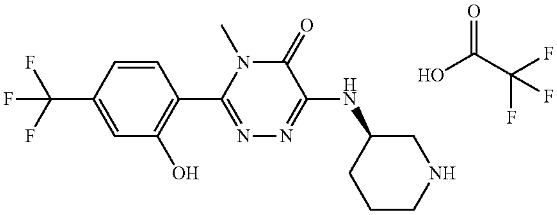 [SMILES: Cn1c(-c2ccc(C(F)(F)F)cc2O)nnc(N[C@@H]2CCCNC2)c1=O ; O=C(O)C(F)(F)F] | 3-[2-Hydroxy-4-(trifluoromethyl)-phenyl]-4-methyl-6-[[(3R)-3-piperidyl]-amino]1,2,4-triazin-5-one; 2,2,2-trifluoro-acetic acid | 170 | |
| 4 | 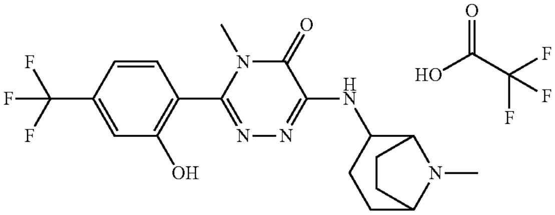 [SMILES: CN1C2CCC(Nc3nnc(-c4ccc(C(F)(F)F)cc4O)n(C)c3=O)C1CC2 ; O=C(O)C(F)(F)F] | 3-[2-Hydroxy-4-(trifluoromethyl)-phenyl]-4-methyl-6-[(8-methyl-8-azabicyclo[3.2.1]-octan-2-yl)amino]-1,2,4-triazin-5-one; 2,2,2-trifluoroacetic acid | 96 | 120 |
| 5 | 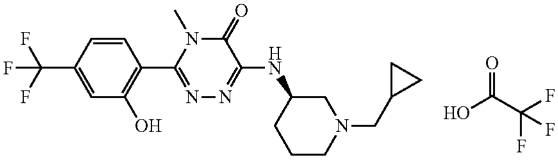 [SMILES: Cn1c(-c2ccc(C(F)(F)F)cc2O)nnc(N[C@@H]2CCCN(CC3CC3)C2)c1=O ; O=C(O)C(F)(F)F] | (R)-6-((1-(Cyclo-propylmethyl)piper-idin-3-yl)amino)-3-(2-hydroxy-4-(trifluoro-methyl)phenyl)-4-methyl-1,2,4-triazin-5(4H)-one; 2,2,2-trifluoroacetic acid | 88 | 92 |
| 6 | 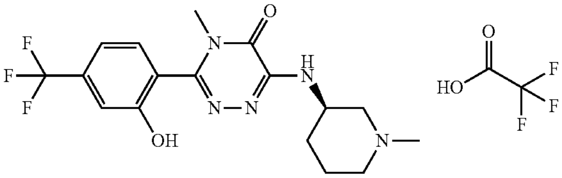 [SMILES: CN1CCC[C@@H](Nc2nnc(-c3ccc(C(F)(F)F)cc3O)n(C)c2=O)C1 ; O=C(O)C(F)(F)F] | (R)-3-(2-Hydroxy-4-(trifluoromethyl)-phenyl)-4-methyl-6-((1-methylpiperidin-3-yl)amino)-1,2,4-triazin-5(4H)-one; 2,2,2-trifluoroacetic acid | 24 | 15 |
| 7 | 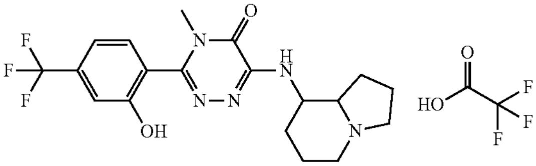 | 6-(1,2,3,5,6,7,8,8a-Octahydroindolizin-8-ylamino)-3-[2-hydroxy-4-(trifluoro-methyl)phenyl]-4-methyl-1,2,4-triazin-5-one; 2,2,2-trifluoro-acetic acid | 51 | 86 |
| 8 | 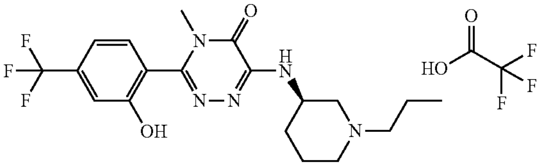 | 3-[2-Hydroxy-4-(trifluoromethyl)-phenyl]-4-methyl-6-[[(3R)-1-propyl-3-piperidyl]amino]-1,2,4-triazin-5-one; 2,2,2-trifluoroacetic acid | 53 | 32 |
| 9 | 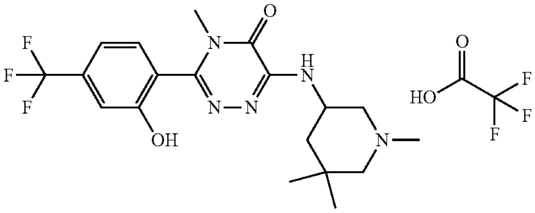 | 3-[2-Hydroxy-4-(trifluoromethyl)-phenyl]-4-methyl-6-[(1,5,5-trimethyl-3-piperidyl)amino]-1,2,4-triazin-5-one; 2,2,2-trifluoroacetic acid | 868 | |

TABLE 1-continued

NLRP3 inhibitory activity

| Example No. | Structure | Name | THP-1 pyroptosis assay IC50 (nM) | Human whole blood IL-1β Assay IC50 (nM) |
|---|---|---|---|---|
| 10 | 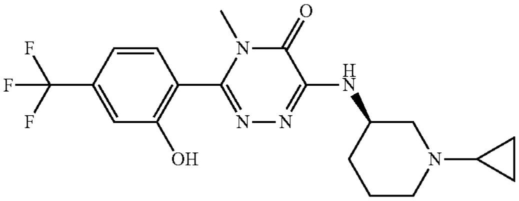 [SMILES: Cn1c(-c2ccc(C(F)(F)F)cc2O)nnc(N[C@@H]2CCCN(C3CC3)C2)c1=O] | (R)-6-((1-Cyclopropylpiperidin-3-yl)amino)-3-(2-hydroxy-4-(trifluoromethyl)phenyl)-4-methyl-1,2,4-triazin-5(4H)-one | 39 | 170 |
| 11 | 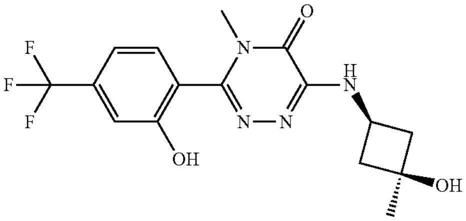 [SMILES: Cn1c(-c2ccc(C(F)(F)F)cc2O)nnc(N[C@H]2C[C@@](C)(O)C2)c1=O] | 6-(((1S,3S)-3-Hydroxy-3-methylcyclobutyl)amino)-3-(2-hydroxy-4-(trifluoromethyl)phenyl)-4-methyl-1,2,4-triazin-5(4H)-one | 391 | 190 |
| 12 | 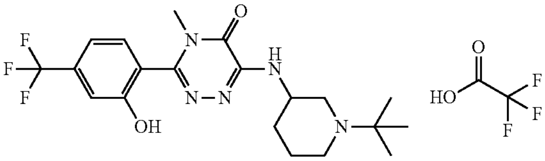 [SMILES: Cn1c(-c2ccc(C(F)(F)F)cc2O)nnc(NC2CCCN(C(C)(C)C)C2)c1=O ; O=C(O)C(F)(F)F] | 6-[(1-tert-Butyl-3-piperidyl)amino]-3-[2-hydroxy-4-(trifluoromethyl)phenyl]-4-methyl-1,2,4-triazin-5-one; 2,2,2-trifluoroacetic acid | | |
| 13 | 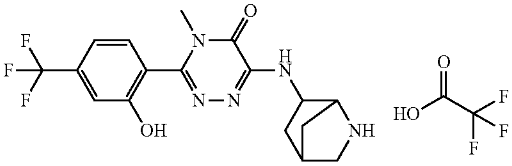 [SMILES: Cn1c(-c2ccc(C(F)(F)F)cc2O)nnc(NC2CC3CNC2C3)c1=O ; O=C(O)C(F)(F)F] | 6-(2-Azabicyclo[2.2.1]heptan-6-ylamino)-3-[2-hydroxy-4-(trifluoromethyl)phenyl]-4-methyl-1,2,4-triazin-5-one; 2,2,2-trifluoroacetic acid | >1000 | |
| 14 | 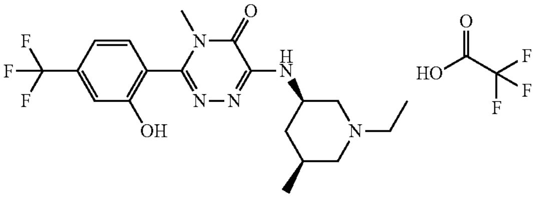 | 6-[[(3R,5S)-1-Ethyl-5-methyl-3-piperidyl]amino]-3-[2-hydroxy-4-(trifluoromethyl)phenyl]-4-methyl-1,2,4-triazin-5-one; 2,2,2-trifluoroacetic acid | 765 | |
| 15 | 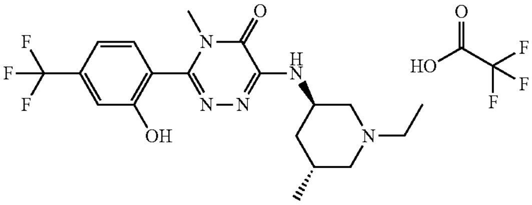 | 6-[[(3R,5R)-1-Ethyl-5-methyl-3-piperidyl]amino]-3-[2-hydroxy-4-(trifluoromethyl)phenyl]-4-methyl-1,2,4-triazin-5-one; 2,2,2-trifluoroacetic acid | >1000 | |
| 16 | 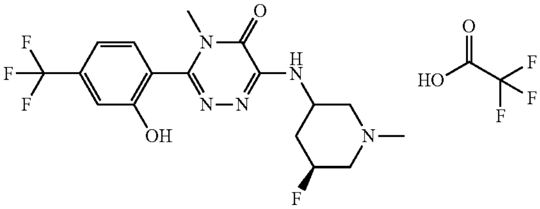 [SMILES: CN1CC(Nc2nnc(-c3ccc(C(F)(F)F)cc3O)n(C)c2=O)C[C@H](F)C1 ; O=C(O)C(F)(F)F] | 6-[[(5S)-5-fluoro-1-methyl-3-piperidyl]amino]-3-[2-hydroxy-4-(trifluoromethyl)phenyl]-4-methyl-1,2,4-triazin-5-one; 2,2,2-trifluoroacetic acid | 860 | |

TABLE 1-continued

NLRP3 inhibitory activity

| Example No. | Structure | Name | THP-1 pyroptosis assay IC50 (nM) | Human whole blood IL-1β Assay IC50 (nM) |
| --- | --- | --- | --- | --- |
| 17 | 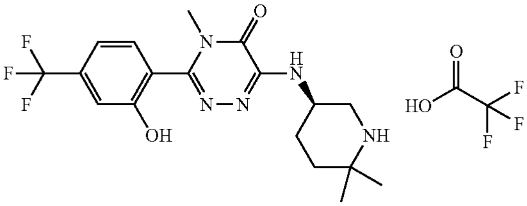 [SMILES: Cn1c(-c2ccc(C(F)(F)F)cc2O)nnc(N[C@@H]2CCC(C)(C)NC2)c1=O ; O=C(O)C(F)(F)F] | 6-[[(3R)-6,6-Dimethyl-3-piperidyl]amino]-3-[2-hydroxy-4-(trifluoromethyl)-phenyl]-4-methyl-1,2,4-triazin-5-one; 2,2,2-trifluoroacetic acid | 683 | |
| 18 | 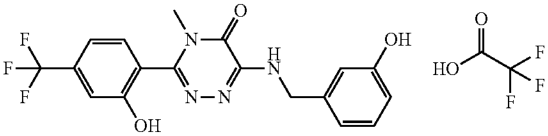 [SMILES: Cn1c(-c2ccc(C(F)(F)F)cc2O)nnc(NCc2cccc(O)c2)c1=O ; O=C(O)C(F)(F)F] | 6-[(3-Hydroxyphenyl)methylamino]-3-[2-hydroxy-4-(trifluoromethyl)-phenyl]-4-methyl-1,2,4-triazin-5-one; 2,2,2-trifluoroacetic acid | 1.2 | 8.1 |
| 19 | 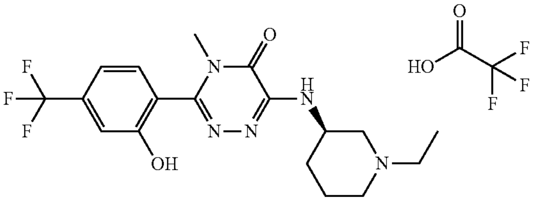 [SMILES: CCN1CCC[C@@H](Nc2nnc(-c3ccc(C(F)(F)F)cc3O)n(C)c2=O)C1 ; O=C(O)C(F)(F)F] | 6-[[(3R)-1-Ethyl-3-piperidyl]amino]-3-[2-hydroxy-4-(trifluoromethyl)-phenyl]-4-methyl-1,2,4-triazin-5-one; 2,2,2-trifluoroacetic acid | 10 | 9.5 |
| 20 | 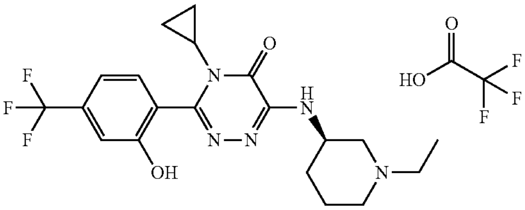 | 4-Cyclopropyl-6-[[(3R)-1-ethyl-3-piperidyl]amino]-3-[2-hydroxy-4-(trifluoromethyl)-phenyl]-1,2,4-triazin-5-one; 2,2,2-trifluoro-acetic acid | 726 | |
| 21 | 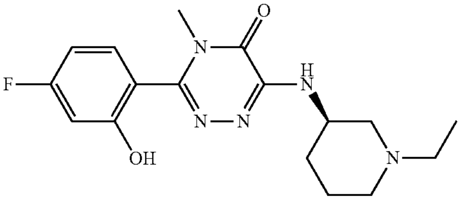 [SMILES: CCN1CCC[C@@H](Nc2nnc(-c3ccc(F)cc3O)n(C)c2=O)C1] | 6-[[(3R)-1-Ethyl-3-piperidyl]amino]-3-(4-fluoro-2-hydroxy-phenyl)-4-methyl-1,2,4-triazin-5-one | 58 | 28 |
| 22 | 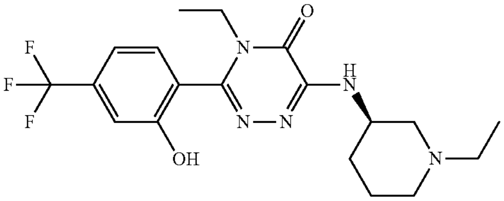 [SMILES: CCN1CCC[C@@H](Nc2nnc(-c3ccc(C(F)(F)F)cc3O)n(CC)c2=O)C1] | 4-Ethyl-6-[[(3R)-1-ethyl-3-piperidyl]-amino]-3-[2-hydroxy-4-(trifluoromethyl)-phenyl]-1,2,4-triazin-5-one | 94 | 48 |

TABLE 1-continued

NLRP3 inhibitory activity

| Example No. | Structure | Name | THP-1 pyroptosis assay IC50 (nM) | Human whole blood IL-1β Assay IC50 (nM) |
|---|---|---|---|---|
| 23 | 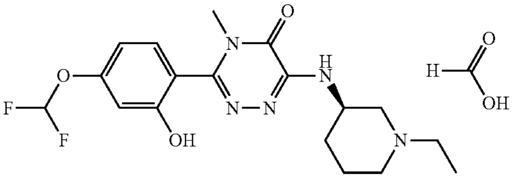 [SMILES: CCN1CCC[C@@H](Nc2nnc(-c3ccc(OC(F)F)cc3O)n(C)c2=O)C1 ; O=CO] | 3-[4-(Difluoromethoxy)-2-hydroxy-phenyl]-6-[[(3R)-1-ethyl-3-piperidyl]amino]-4-methyl-1,2,4-triazin-5-one; formic acid | 8.1 | 6.5 |
| 24 | 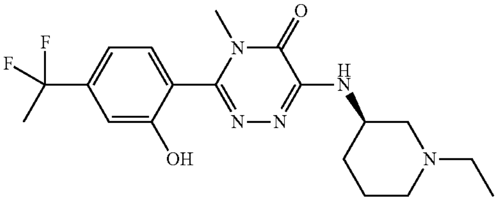 [SMILES: CCN1CCC[C@@H](Nc2nnc(-c3ccc(C(C)(F)F)cc3O)n(C)c2=O)C1] | 3-[4-(1,1-Difluoroethyl)-2-hydroxy-phenyl]-6-[[(3R)-1-ethyl-3-piperidyl]-amino]-4-methyl-1,2,4-triazin-5-one | 106 | 108 |
| 25 | 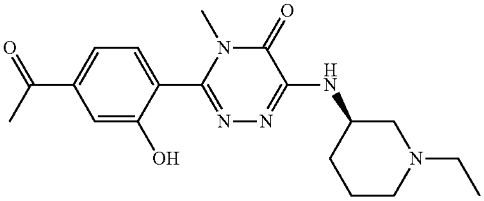 [SMILES: CCN1CCC[C@@H](Nc2nnc(-c3ccc(C(C)=O)cc3O)n(C)c2=O)C1] | 3-(4-Acetyl-2-hydroxy-phenyl)-6-[[(3R)-1-ethyl-3-piperidyl]amino]-4-methyl-1,2,4-triazin-5-one | 9.3 | 15 |
| 26 | 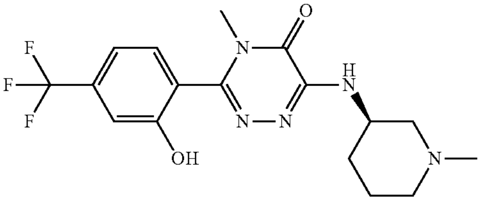 [SMILES: CN1CCC[C@@H](Nc2nnc(-c3ccc(C(F)(F)F)cc3O)n(C)c2=O)C1] | 3-[2-hydroxy-4-(trifluoromethyl)-phenyl]-4-methyl-6-[[(3R)-1-methyl-3-piperidyl]amino]-1,2,4-triazin-5-one | 10.3 | |
| 27 | 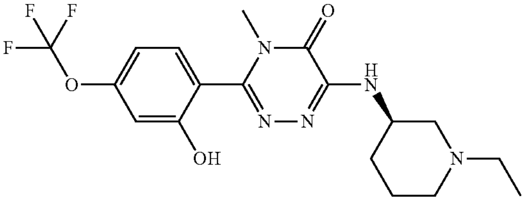 [SMILES: CCN1CCC[C@@H](Nc2nnc(-c3ccc(OC(F)(F)F)cc3O)n(C)c2=O)C1] | 6-[[(3R)-1-Ethyl-3-piperidyl]amino]-3-[2-hydroxy-4-(trifluoromethoxy)-phenyl]-4-methyl-1,2,4-triazin-5-one | 12 | 14 |
| 28 | 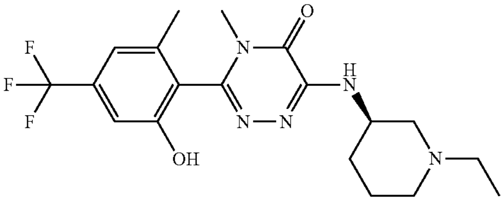 [SMILES: CCN1CCC[C@@H](Nc2nnc(-c3c(C)cc(C(F)(F)F)cc3O)n(C)c2=O)C1] | 6-[[(3R)-1-Ethyl-3-piperidyl]amino]-3-[2-hydroxy-6-methyl-4-(trifluoromethyl)-phenyl]-4-methyl-1,2,4-triazin-5-one | 13 | 31 |

TABLE 1-continued

| NLRP3 inhibitory activity | | | | |
|---|---|---|---|---|
| Example No. | Structure | Name | THP-1 pyroptosis assay IC50 (nM) | Human whole blood IL-1β Assay IC50 (nM) |
| 29 | 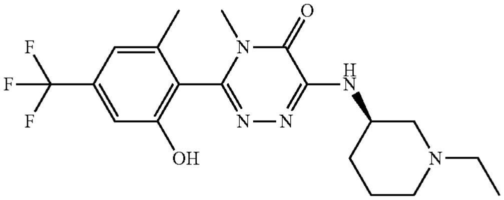 [SMILES: CCN1CCC[C@@H](Nc2nnc(-c3c(C)cc(C(F)(F)F)cc3O)n(C)c2=O)C1] | (M or P)-6-[[(3R)-1-ethyl-3-piperidyl]-amino]-3-[2-hydroxy-6-methyl-4-(trifluoro-methyl)phenyl]-4-methyl-1,2,4-triazin-5-one | 7.8 | |
| 30 | 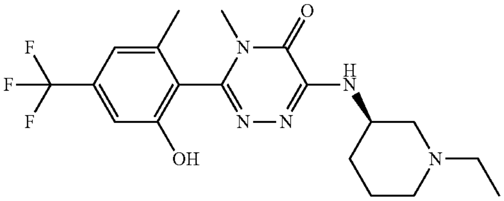 [SMILES: CCN1CCC[C@@H](Nc2nnc(-c3c(C)cc(C(F)(F)F)cc3O)n(C)c2=O)C1] | (P or M)-6-[[(3R)-1-ethyl-3-piperidyl]-amino]-3-[2-hydroxy-6-methyl-4-(trifluoro-methyl)phenyl]-4-methyl-1,2,4-triazin-5-one | 751 | |
| 31 | 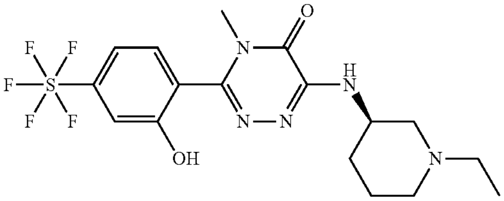 [SMILES: CCN1CCC[C@@H](Nc2nnc(-c3ccc(S(F)(F)(F)(F)F)cc3O)n(C)c2=O)C1] | 6-[[(3R)-1-Ethyl-3-piperidyl]amino]-3-[2-hydroxy-4-(penta-fluoro-26-sulfanyl)-phenyl]-4-methyl-1,2,4-triazin-5-one | 115 | |
| 32 | 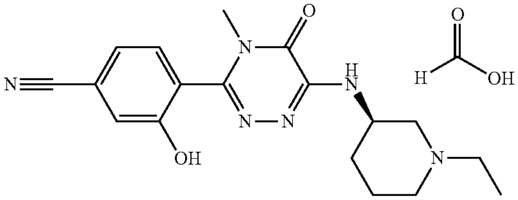 | 4-[6-[[(3R)-1-Ethyl-3-piperidyl]amino]-4-methyl-5-oxo-1,2,4-triazin-3-yl]-3-hydroxy-benzo-nitrile; formic acid | 809 | |
| 33 | 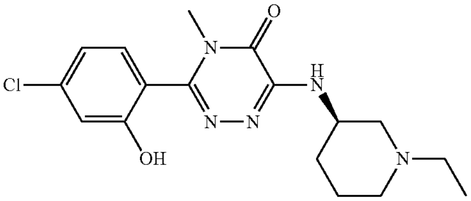 [SMILES: CCN1CCC[C@@H](Nc2nnc(-c3ccc(Cl)cc3O)n(C)c2=O)C1] | 3-(4-Chloro-2-hydroxy-phenyl)-6-[[(3R)-1-ethyl-3-piperidyl]amino]-4-methyl-1,2,4-triazin-5-one | 5.9 | 5.9 |
| 34 | 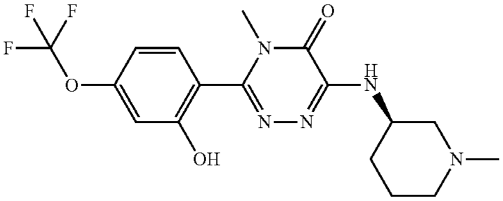 [SMILES: CN1CCC[C@@H](Nc2nnc(-c3ccc(OC(F)(F)F)cc3O)n(C)c2=O)C1] | 3-[2-Hydroxy-4-(trifluoromethoxy)-phenyl]-4-methyl-6-[[(3R)-1-methyl-3-piperidyl]amino]-1,2,4-triazin-5-one | 13.1 | 35.2 |
| 35 | 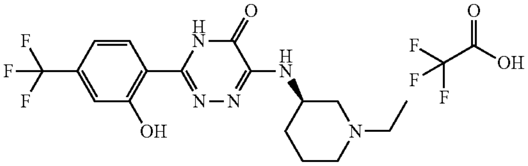 | 6-[[(3R)-1-Ethyl-3-piperidyl]amino]-3-[2-hydroxy-4-(trifluoromethyl)-phenyl]-4H-1,2,4-triazin-5-one; 2,2,2-trifluoroacetic acid | 459 | |

TABLE 1-continued

| NLRP3 inhibitory activity | | | | |
|---|---|---|---|---|
| Example No. | Structure | Name | THP-1 pyroptosis assay IC50 (nM) | Human whole blood IL-1β Assay IC50 (nM) |
| 36 | 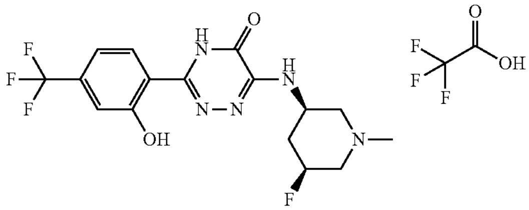 [SMILES: CN1C[C@@H](F)C[C@@H](Nc2nnc(-c3ccc(C(F)(F)F)cc3O)[nH]c2=O)C1 ; O=C(O)C(F)(F)F] | 6-[[(3R,5S)-1-ethyl-5-fluoro-3-piperidyl]-amino]-3-[2-hydroxy-4-(trifluoromethyl)-phenyl]-4H-1,2,4-triazin-5-one; 2,2,2-trifluoroacetic acid | >1000 | |

TABLE 2

| NLRP3 inhibitory activity | | | |
|---|---|---|---|
| Example No. | Structure | Name | hERG assay IC50 (μM) |
| 1 | 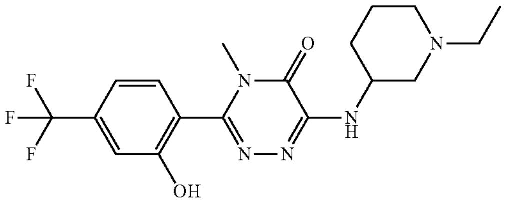 [SMILES: CCN1CCCC(Nc2nnc(-c3ccc(C(F)(F)F)cc3O)n(C)c2=O)C1] | 6-((1-Ethylpiperidin-3-yl)amino)-3-(2-hydroxy-4-(trifluoromethyl)phenyl)-4-methyl-1,2,4-triazin-5(4H)-one | >20 μM |
| 2 | 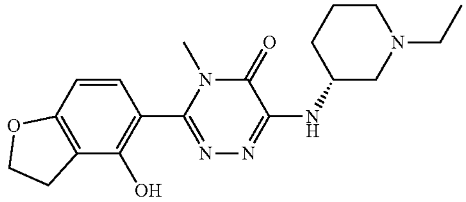 [SMILES: CCN1CCC[C@@H](Nc2nnc(-c3ccc4c(c3O)CCO4)n(C)c2=O)C1] | 6-[[(3R)-1-Ethyl-3-piperidyl]amino]-3-(4-hydroxy-2,3-dihydrobenzofuran-5-yl)-4-methyl-1,2,4-triazin-5-one | >20 μM |
| 10 | 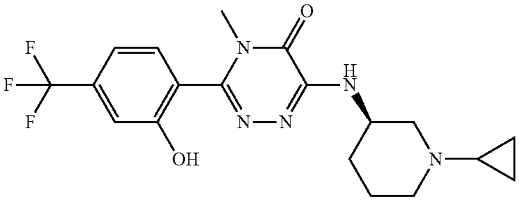 [SMILES: Cn1c(-c2ccc(C(F)(F)F)cc2O)nnc(N[C@@H]2CCCN(C3CC3)C2)c1=O] | (R)-6-((1-Cyclopropylpiperidin-3-yl)amino)-3-(2-hydroxy-4-(trifluoromethyl)phenyl)-4-methyl-1,2,4-triazin-5(4H)-one | >20 μM |
| 19 | 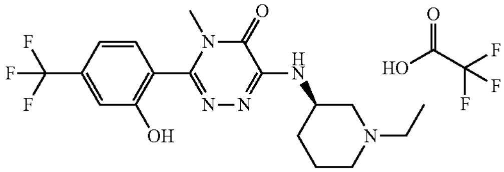 | 6-[[(3R)-1-Ethyl-3-piperidyl]amino]-3-[2-hydroxy-4-(trifluoromethyl)phenyl]-4-methyl-1,2,4-triazin-5-one; 2,2,2-trifluoroacetic acid | >20 μM |

TABLE 2-continued

| NLRP3 inhibitory activity | | | |
|---|---|---|---|
| Example No. | Structure | Name | hERG assay IC50 (μM) |
| 21 | 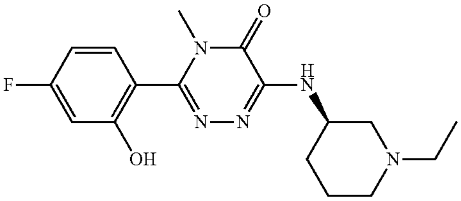 [SMILES: CCN1CCC[C@@H](Nc2nnc(-c3ccc(F)cc3O)n(C)c2=O)C1] | 6-[[(3R)-1-Ethyl-3-piperidyl]amino]-3-(4-fluoro-2-hydroxy-phenyl)-4-methyl-1,2,4-triazin-5-one | >20 μM |
| 27 | 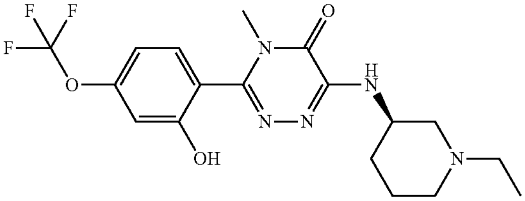 [SMILES: CCN1CCC[C@@H](Nc2nnc(-c3ccc(OC(F)(F)F)cc3O)n(C)c2=O)C1] | 6-[[(3R)-1-Ethyl-3-piperidyl]amino]-3-[2-hydroxy-4-(trifluoro-methoxy)phenyl]-4-methyl-1,2,4-triazin-5-one | >20 μM |
| 28 | 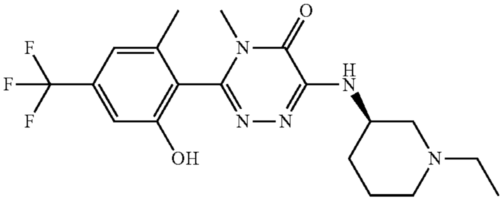 [SMILES: CCN1CCC[C@@H](Nc2nnc(-c3c(C)cc(C(F)(F)F)cc3O)n(C)c2=O)C1] | 6-[[(3R)-1-Ethyl-3-piperidyl]amino]-3-[2-hydroxy-6-methyl-4-(trifluoromethyl)phenyl]-4-methyl-1,2,4-triazin-5-one | >20 μM |
| 33 | 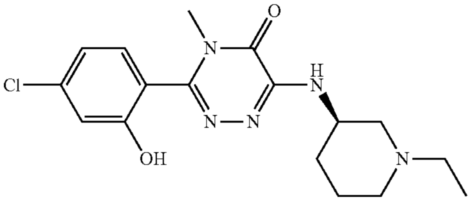 [SMILES: CCN1CCC[C@@H](Nc2nnc(-c3ccc(Cl)cc3O)n(C)c2=O)C1] | 3-(4-Chloro-2-hydroxy-phenyl)-6-[[(3R)-1-ethyl-3-piperidyl]amino]-4-methyl-1,2,4-triazin-5-one | >20 μM |
| RE-A* | 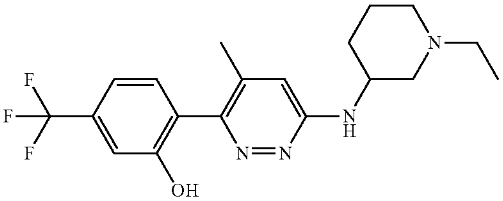 | 2-[6-[(1-ethyl-3-piperidyl)-amino]-4-methyl-pyrid-azin-3-yl]-5-(trifluoro-methyl)phenol | 1.2 μM |

*RE-A was synthesized in analogy to as described in WO20200234715.

The invention will now be illustrated by the following examples which have no limiting character.

In case the preparative examples are obtained as a mixture of enantiomers, the pure enantiomers can be obtained by methods described herein or by methods known to those skilled in the art, such as e.g. chiral chromatography or crystallization.

Experimental Methods

Abbreviations

| | |
|---|---|
| EtOAc | ethyl acetate |
| TFA | trifluoroacetic acid |
| DCM | dichloromethane |
| THF | tetrahydrofuran |
| ACN | acetonitrile |
| PE | petroleum ether |
| TEA | triethylamine |

-continued

| | |
|---|---|
| DIEA, DIPEA | diisopropylethylamine |
| DMF | N,N-dimethylformamide |
| EDCI | 1-Ethyl-3-(3-dimethylaminopropyl)carbodiimide |
| HOBt | Hydroxybenzotriazole |
| Prep-HPLC | preparative-High performance liquid chromatography |
| MeOH | methanol |
| eq | equivalent |
| aq. | aqueous phase |

Analytical Methods

NMR spectra were run on Bruker 400 MHz spectrometers using ICON-NMR, under TopSpin program control. Spectra were measured at 298 K, unless indicated otherwise, and were referenced relative to the solvent resonance.

LC-MS Methods

Method 1: Using SHIMADZU LCMS-2020, Agilent 1200 LC/G1956A MSD and Agilent 1200\G6110A, Agilent 1200 LC & Agilent 6110 MSD. Mobile Phase: A: 0.038% TFA in water (v/v); B: 0.019% TFA in Acetonitrile (v/v). Column: Kinetex EVO $C_{18}$ 2.1×30 mm, 5 μm.

Method 2: Using SHIMADZU LCMS-2020, Agilent 1200 LC/G1956A MSD and Agilent 1200\G6110A, Agilent 1200 LC & Agilent 6110 MSD. Mobile Phase: A: 0.025% $NH_3 \cdot H_2O$ in water (v/v); B: Acetonitrile. Column: Kinetex EVO C18 2.1×30 mm, 5 um.

Purification Method (Example 1; Step I)

Automated reversed phase column chromatography was carried out using a Gilson GX-281 system driven by a Gilson-322 pump module, Gilson-156 UV photometer detection unit and Gilson-281 fraction collector.

Phenomenex Gemini: 150 mm*25 mm*5 um pH (water(10 mM $NH_4HCO_3$)-ACN): 7-8

Average particle size: 5 μm

The column was conditioned before use with 100% MeCN (2 min) then brought to 1% MeCN (in 0.8 min). Flow rate=28 mL/min.

Separation Runs:

| Time (min) | A: water(10 mM $NH_4HCO_3$) | B: MeCN |
|---|---|---|
| 0 | 68% | 32% |
| 1.0 | 68% | 32% |
| 10.0 | 38% | 62% |
| 10.2 | 0% | 100% |
| 12.0 | 0% | 100% |
| 12.2 | 95% | 5% |
| 13.0 | 95% | 5% |

Detection wavelength: 220 and 254 nm. Before each new run, the cartridge was cleaned using the conditioning method.

EXAMPLES

All examples and intermediates were prepared under nitrogen atmosphere if not specified otherwise.

Example 1: 6-((1-ethylpiperidin-3-yl)amino)-3-(2-hydroxy-4-(trifluoromethyl)phenyl)-4-methyl-1,2,4-triazin-5(4H)-one

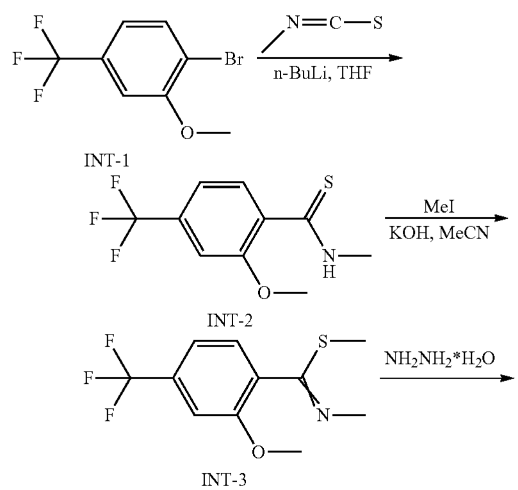

INT-1

INT-2

INT-3

-continued

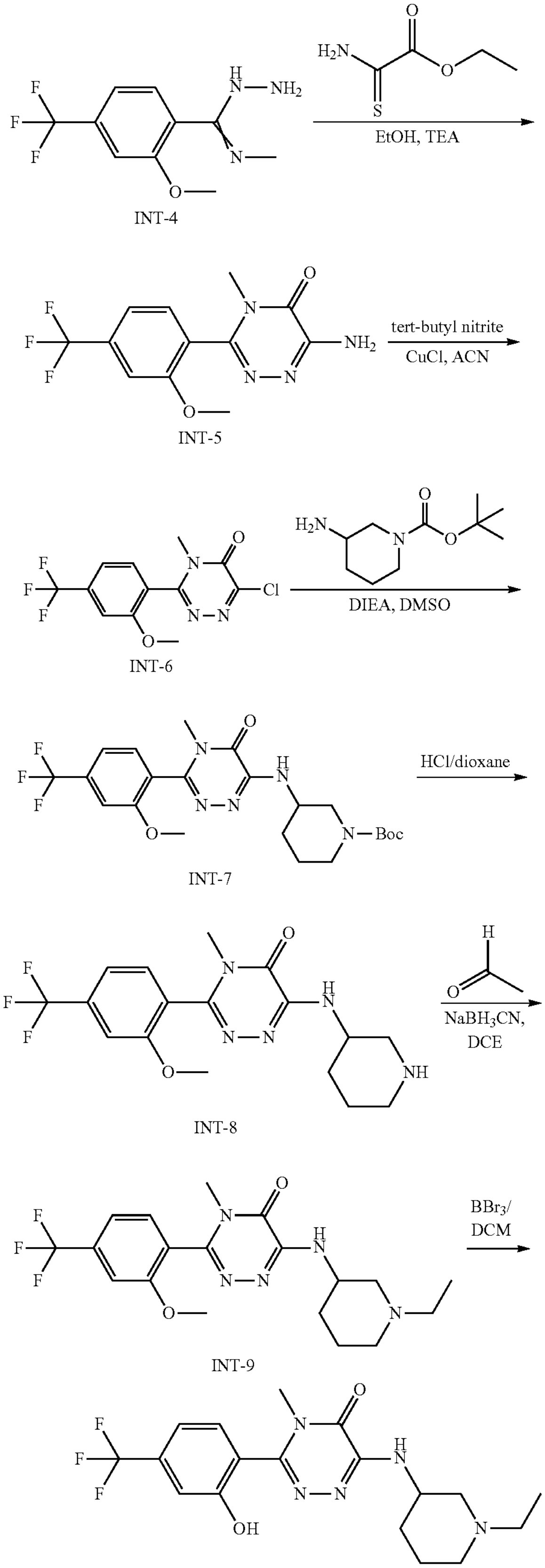

INT-4

INT-5

INT-6

INT-7

INT-8

INT-9

Example 1

Step A: 2-Methoxy-N-methyl-4-(trifluoromethyl)benzothioamide

INT-2

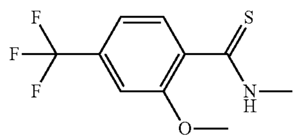

To a mixture of 1-bromo-2-methoxy-4-(trifluoromethyl)benzene (5.0 g, 19.6 mmol, 1 eq) was dropwise added n-BuLi in THF (10.2 mL, 25.5 mmol, 1.3 eq) at −70° C. under $N_2$, and stirred for 10 mins, then the methyl isothiocyanate (2150 mg, 29.4 mmol, 1.5 eq) was added and stirred for 1 hour at 25° C. TLC (PE/EtOAc=3:1) showed the reaction was completed. The mixture was quenched by water (10 ml) and the aqueous layer was extracted with EtOAc (100 mL) twice. The combined organic layers were washed with an aqueous solution of 50 mL water and dried over $Na_2SO_4$. The crude product was purified by column chromatography on silica gel (gradient with PE:EtOAc=100:1 to 5:1) to yield the title compound (1 g, 20.5% yield) as black oil.

LCMS: m/z 249.9 $(M+H)^+$ $(ES^+)$.

Step B: Methyl 2-methoxy-N-methyl-4-(trifluoromethyl)benzenecarboximidothioate

INT-3

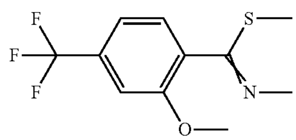

To 2-methoxy-N-methyl-4-(trifluoromethyl)benzenecarbothioamide (3.3 g, 11.3 mmol, 1 eq) in MeCN (20 mL) KOH (694 mg, 12.4 mmol, 1.1 eq) and Mel (1.6 g, 11.3 mmol, 1 eq) were subsequently added and the reaction was stirred for 2 h at 50° C. The mixture was poured into ice-water (w/w=1/1) (10 mL) and stirred for 1 mins. The aqueous phase was extracted with EtOAc (100 mL*3). The combined organic phase was washed with brine (50 mL), dried with anhydrous $Na_2SO_4$, filtered and concentrated in vacuum. The crude product was purified by prep-TLC ($SiO_2$, PE/EtOAc=3:1) to give title compound (1.7 g, 40% yield) as black oil.

LCMS: m/z 263.8 $(M+H)^+$ $(ES^+)$.

Step C: N-amino-2-methoxy-N'-methyl-4-(trifluoromethyl)benzamidine

INT-4

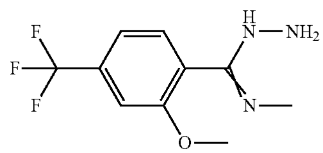

To a mixture of hydrazine hydrate (1.4 g, 26.6 mmol, 10 eq) in EtOH (2 mL) was added dropwise a solution of methyl 2-methoxy-N-methyl-4-(trifluoromethyl)benzenecarboximidothioate (700 mg, 2.7 mmol, 1 eq) in EtOH (1 mL) at 70° C. under $N_2$ and stirred for 2 hours at 70° C. The mixture was poured into ice-water (w/w=1/1) (10 mL) and stirred for 5 mins. The aqueous phase was extracted with EtOAc (50 mL*2). The combined organic phase was washed with brine (10 mL*2), dried with anhydrous $Na_2SO_4$, filtered and concentrated in vacuum. The crude product was purified by reversed-phase flash chromatography (0.1% TFA condition) to give the title compound (340 mg, 45% yield) as a white solid.

LCMS: m/z 248.1 $(M+H)^+$ $(ES^+)$.

Step D: 6-Amino-3-(2-methoxy-4-(trifluoromethyl)phenyl)-4-methyl-1,2,4-triazin-5(4H)-one

INT-5

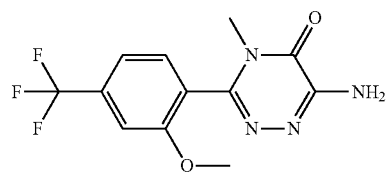

A mixture of N-amino-2-methoxy-N'-methyl-4-(trifluoromethyl)benzamidine (290 mg, 1.2 mmol, 1 eq), TEA (237 mg, 2.4 mmol, 2 eq) and ethyl thiooxamate (234 mg, 1.8 mmol, 1.5 eq) in EtOH (5 mL) was stirred for 2 hours at 80° C. The mixture was filtered and the filtrate was concentrated in vacuum. The crude product was purified by reversed-phase flash chromatography (0.1% TFA condition) to give the title compound (160 mg, 43% yield) as a light yellow solid.

LCMS: m/z 300.9 $(M+H)^+$ $(ES^+)$.

Step E: 6-Chloro-3-(2-methoxy-4-(trifluoromethyl)phenyl)-4-methyl-1,2,4-triazin-5(4H)-one

INT-6

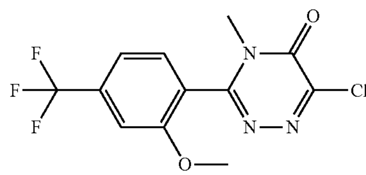

A mixture of 6-amino-3-[2-methoxy-4-(trifluoromethyl)phenyl]-4-methyl-1,2,4-triazin-5-one (100 mg, 0.33 mmol, 1 eq), tert-butyl nitrite (69 mg, 0.67 mmol, 2 eq), CuCl (66 mg, 0.67 mmol, 2 eq) in ACN (3 mL) was stirred at 70° C. for 1 hour under $N_2$ atmosphere. The mixture was poured into ice-water (w/w=1/1) (5 mL) and stirred for 5 mins. The aqueous phase was extracted with ethyl acetate (20 mL*3). The combined organic phase was washed with brine (10 mL*2), dried with anhydrous $Na_2SO_4$, filtered and concentrated in vacuum. The residue was purified by prep-TLC ($SiO_2$, PE/EtOAc=1/1) to afford the title compound (40 mg, 38% yield) as a yellow solid.

LCMS: m/z 320.0 $(M+H)^+$ $(ES^+)$.

Step F: Tert-butyl 3-[[3-[2-methoxy-4-(trifluoromethyl)phenyl]-4-methyl-5-oxo-1,2,4-triazin-6-yl]amino]piperidine-1-carboxylate

INT-7

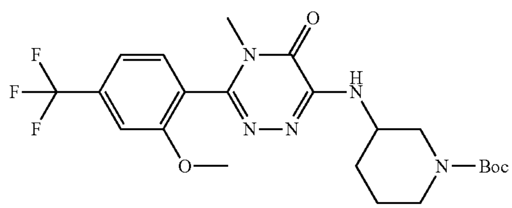

To a mixture of 6-chloro-3-[2-methoxy-4-(trifluoromethyl)phenyl]-4-methyl-1,2,4-triazin-5-one (40 mg, 0.11 mmol, 1 eq) and tert-butyl 3-aminopiperidine-1-carboxylate (214 mg, 1.1 mmol, 10 eq) was added DIEA (276 mg, 2.14 mmol, 20 eq) in DMSO (1 mL) and the reaction was stirred at 60° C. for 16 hours. Afterwards, the mixture was concentrated in vacuum. The crude product was purified by reversed-phase HPLC (0.1% TFA condition) to give the title compound (40 mg, 73% yield) as a white solid.

LCMS: m/z 484.1 $(M+H)^+$ $(ES^+)$.

Step G: 3-[2-Methoxy-4-(trifluoromethyl)phenyl]-4-methyl-6-(3-piperidylamino)-1,2,4-triazin-5(4H)-one

INT-8

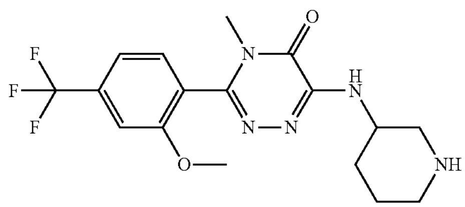

A mixture of tert-butyl 3-[[3-[2-methoxy-4-(trifluoromethyl)phenyl]-4-methyl-5-oxo-1,2,4-triazin-6-yl]amino]piperidine-1-carboxylate (40 mg, 0.08 mmol, 1 eq) and HCl/dioxane (1.0 mL, 4 mmol, 48 eq) was stirred at 25° C. for 1 hour. Afterwards, the mixture was concentrated in vacuum. The crude product was purified by reversed-phase HPLC (0.1% HCl condition) to give the title compound as a yellow solid (HCl salt, 30 mg, 72% yield).

LCMS: m/z 384.0 $(M+H)^+$ $(ES^+)$.

Step H: 6-[(1-Ethyl-3-piperidyl)amino]-3-[2-methoxy-4-(trifluoromethyl)phenyl]-4-methyl-1,2,4-triazin-5-one

INT-9

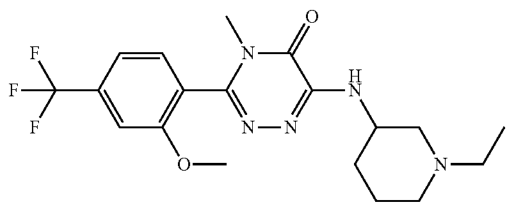

The mixture of 3-[2-methoxy-4-(trifluoromethyl)phenyl]-4-methyl-6-(3-piperidylamino)-1,2,4-triazin-5-one; hydrochloride (30 mg, 0.07 mmol, 1 eq) and acetaldehyde (0.05 mL, 0.36 mmol, 5 eq), NaOAc (29 mg, 0.36 mmol, 5 eq) in 1,2-dichloroethane (1 mL) was stirred at 25° C. for 1 hour, then the $NaBH_3CN$ (23 mg, 0.36 mmol, 5 eq) was added and stirred at 25° C. for 1 hour. The mixture was filtered and the filtrate was concentrated in vacuum. The crude product was purified by reversed-phase flash (0.1% TFA condition) to give the title compound as a yellow solid (TFA salt, 30 mg, 72% yield)

LCMS: m/z 412.0 $(M+H)^+$ $(ES^+)$.

Step I: 6-[(1-Ethyl-3-piperidyl)amino]-3-[2-hydroxy-4-(trifluoromethyl)phenyl]-4-methyl-1,2,4-triazin-5(4H)-one Example 1

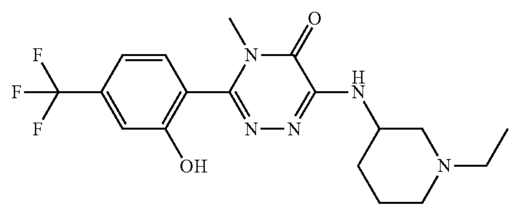

A mixture of boron tribromide (143 mg, 0.57 mmol, 10 eq) and 6-[(1-ethyl-3-piperidyl)amino]-3-[2-methoxy-4-(trifluoromethyl)phenyl]-4-methyl-1,2,4-triazin-5-one;2,2,2-trifluoroacetic acid (30.0 mg, 0.06 mmol, 1 eq) in DCM (3 mL) was stirred at −70° C. for 2 hours. Afterwards, the pH was adjusted to pH~8 by addition of $NH_3H_2O$, then filtered and the filtrate was concentrated in vacuum. The crude product was purified by prep-HPLC (column Waters Xbridge 150*25 mm*5 um, water (10 mM $NH4HCO_3$)-ACN, B %: 32%-62%, 10 min) to give the title compound (10 mg, 0.03 mmol, 43% yield) as a white solid.

LCMS: m/z 398.1 $(M+H)^+$ $(ES^+)$.

Example 2: 6-[[(3R)-1-Ethyl-3-piperidyl]amino]-3-(4-hydroxy-2,3-dihydrobenzofuran-5-yl)-4-methyl-1,2,4-triazin-5-one

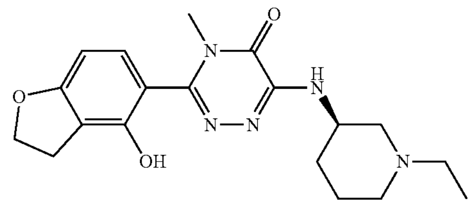 [SMILES: CCN1CCC[C@@H](Nc2nnc(-c3ccc4c(c3O)CCO4)n(C)c2=O)C1]

Step A: 6-Bromo-2-[(4-methoxyphenyl)methyl]-4-methyl-1,2,4-triazine-3,5-dione

6-Bromo-4-methyl-2H-1,2,4-triazine-3,5-dione (13.8 g, 63.1 mmol, 1.0 eq) and potassium carbonate (4.84 g, 31.5 mmol, 0.50 eq) were suspended in dry DMF (125 mL) and 4-methoxy benzylchloride (10.3 mL, 75.7 mmol, 1.2 eq) was added. The reaction mixture was stirred at room temperature for 24 h. The reaction mixture was diluted with EtOAc (50 mL) and washed with 10 wt % aqueous LiCl (2×30 mL), dried using a phase separator and concentrated in vacuo. The resulting residue was purified by chromatography on silica gel (330 g column, 0-50% EtOAc/isohexane) to afford the title compound (15.9 g, 77% yield) as a white solid. $^1$H NMR (500 MHz, DMSO-$d_6$) δ7.33-7.25 (m, 2H), 6.97-6.89 (m, 2H), 5.00 (s, 2H), 3.74 (s, 3H), 3.20 (s, 3H).

Step B: 6-[[(3R)-1-Ethyl-3-piperidyl]amino]-2-[(4-methoxyphenyl)methyl]-4-methyl-1,2,4-triazine-3,5-dione (3R)-1-ethylpiperidin-3-amine (6.0 g, 46.9 mmol, 1.53 eq) and 6-bromo-2-[(4-methoxyphenyl)methyl]-4-methyl-1,2,4-triazine-3,5-dione (10 g, 30.7 mmol, 1.0 eq) and cesium carbonate (20 g, 61.3 mmol, 2.0 eq) were dissolved in DMSO (125 mL) and the mixture degassed ($N_2$) for 5 min. The reaction vessel was evacuated and back-filled with $N_2$ (3×), then (rac)-BINAP Pd G3 (1 g, 1.01 mmol, 0.030 eq) was added and the reaction mixture placed under $N_2$, then stirred at 95° C. for 24 h. The reaction mixture was partitioned between EtOAc (500 mL) and water (500 mL). The organic phase was isolated, washed with brine (3×300 mL), dried using a phase separator and concentrated in vacuo. The resulting residue was purified by chromatography on silica gel (220 g column, 0-7% (0.7 N ammonia in MeOH) in DCM) to afford the title compound (10.4 g, 86% yield) as an orange oil. LCMS m/z 374.2 [M+H]$^+$, ESI pos.

Step C: 6-[[(3R)-1-Ethyl-3-piperidyl]amino]-4-methyl-2H-1,2,4-triazine-3,5-dione; Trifluoromethanesulfonic Acid Salt 6-[[(3R)-1-ethyl-3-piperidyl]amino]-2-[(4-methoxyphenyl)methyl]-4-methyl-1,2,4-triazine-3,5-dione (10.4 g, 25.1 mmol, 1.0 eq) was dissolved in DCM (75 mL). Trifluoromethanesulfonic acid (3.33 mL, 37.7 mmol, 1.5 eq) was added to the reaction. The resulting solution was stirred at room temperature for 24 h. A further portion of trifluoromethanesulfonic acid (3.33 mL, 37.7 mmol, 1.5 eq) was added and the reaction mixture stirred for a further 3 h. The reaction mixture was concentrated in vacuo and the resulting residue was purified by chromatography on silica gel (220 g column, 0-10% (0.7 N ammonia in MeOH/DCM) to afford the title compound (17.04 g, 84% yield) as a yellow oil. LCMS m/z 254.5 [M+H]$^+$, ESI pos.

Step D: 3-Chloro-6-[[(3R)-1-ethyl-3-piperidyl]amino]-4-methyl-1,2,4-triazin-5-one 6-[[(3R)-1-Ethyl-3-piperidyl]amino]-4-methyl-2H-1,2,4-triazine-3,5-dione; trifluoromethanesulfonic acid salt (17.04 g, 21.1 mmol, 1 eq) was dissolved in phosphorus oxychloride (75.0 mL, 804.6 mmol, 38.1 eq). The reaction was stirred at 120° C. for 72 h. A 15 mL aliquot of the reaction mixture was concentrated in vacuo and the resulting residue diluted with EtOAc (200 mL), washed with 1:1 brine: saturated aqueous $NaHCO_3$ solution (200 mL). The organic phase was isolated and the aqueous back-extracted with EtOAc (200 mL). The combined organic extracts were dried ($MgSO_4$) and concentrated in vacuo to afford the title compound (1.03 g, 17% yield) as a brown oil. The remaining reaction mixture was subjected to the same workup conditions, proportionately scaled, and afforded the title compound (5.06 g, 79% yield) as a brown oil. LCMS m/z 274.4 ([37Cl]M+H)$^+$, ESI pos.

Step A': 5-Bromo-2,3-dihydrobenzofuran-4-ol

To a solution of 2,3-dihydrobenzofuran-4-ol (CAS #144822-82-2, 2.00 g, 14.7 mmol, 1 eq) in methanol (40 mL) was added pyridine tribromide (4.70 g, 14.7 mmol, 1 eq) at −40° C. The resulting mixture was stirred at −40° C. for 0.5 hour, then warmed to 20° C. and stirred for 16 hours. After reaction completion, the reaction mixture was dissolved in EtOAc (100 mL). The organic layer was washed with 1 N hydrochloric acid (100 mL×2), followed by brine (100 mL), dried over anhydrous sodium sulfate, filtered and the filtrate was concentrated under reduced pressure. The residue was purified by column chromatography ($SiO_2$, PE:EtOAc=15:1 to 10:1) to afford the title compound (1.90 g, 60% yield) as a yellow solid. LCMS: m/z 212.8 [M−H]$^-$, ESI neg.

Step B': 2-[(5-Bromo-2,3-dihydrobenzofuran-4-yl)oxymethoxy]ethyl-trimethylsilane To a solution of 5-bromo-2,3-dihydrobenzofuran-4-ol (Example 7, Step A) (1.00 g, 4.65 mmol, 1.0 eq) in ACN (20 mL) was added $K_2CO_3$ (1.29 g, 9.3 mmol, 2.0 eq). The mixture was stirred at 20° C. for 0.5 hour and 2-(trimethylsilyl)ethoxymethyl chloride (0.99 mL, 5.58 mmol, 1.2 eq) was added to the mixture by drop wise. The mixture was stirred at 20° C. for 2 hours. TLC (PE:EtOAc=10:1) showed the starting material was consumed up and another main spot was formed. The mixture was quenched with water (100 mL) and extracted with EtOAc (100 mL×3). The organic phase was washed with brine (150 mL), dried over anhydrous sodium sulfate, filtered and the filtrate was concentrated under reduced pressure. The residue was purified by column chromatography ($SiO_2$, PE:EtOAc=20:1 to 15:1) to the title compound (1.30 g, 81% yield) as yellow oil. $^1$H NMR (400 MHZ, DMSO-$d_6$) δ=7.30 (d, 1H), 6.49 (d, 1H), 5.19 (s, 2H), 4.54 (t, 2H), 3.87-3.74 (m, 2H), 3.32-3.26 (m, 2H), 0.94-0.86 (m, 2H), −0.01-−0.05 (m, 9H).

Step C': Trimethyl-[2-[[5-(4,4,5,5-tetramethyl-1,3,2-dioxaborolan-2-yl)-2,3-dihydrobenzofuran-4-yl]oxymethoxy]ethyl]silane To a solution of 2-[(5-bromo-2,3-dihydrobenzofuran-4-yl)oxymethoxy]ethyl-trimethylsilane (1.20 g, 3.48 mmol, 1.0 eq) in isopropyl acetate (20 mL) was added bis(pinacolato)diboron (1.06 g. 4.17 mmol. 1.2 eq), anhydrous AcOK (0.75 g. 7.65 mmol, 2.2 eq), Xphos (166 mg, 0.350 mmol, 0.100 eq) and XPhos Pd G3 (295 mg. 0.350 mmol, 0.100 eq). The mixture was degassed with $N_2$ three times and stirred at 80° C. 12 hours under $N_2$. TLC (PE:EtOAc=20:1) showed the starting material was consumed and one new spot was detected. The mixture was quenched with water (30 mL) and extracted with EtOAc (30 mL×3). The organic phase was washed with brine (30 mL×2), dried over anhydrous sodium sulfate, filtered and the filtrate was concentrated under reduced pressure. The residue was first purified by column chromatography (SiO2, PE:EtOAc=80:1 to 50:1), followed by reversed-phase flash (CombiFlash 0.1% $NH_3 \cdot H_2O$ aqueous-ACN) and follow up lyophilization to afford the title compound (288.3 mg. 20% yield) as colorless oil. LCMS: m/z 393.1 [M+H]$^+$, ESI pos.

Step E: 6-[[(3R)-1-Ethyl-3-piperidyl]amino]-3-(4-hydroxy-2,3-dihydrobenzofuran-5-yl)-4-methyl-1,2,4-triazin-5-one 3-Chloro-6-[[(3R)-1-ethyl-3-piperidyl]amino]-4-methyl-1,2,4-triazin-5-one (160 mg, 0.530 mmol, 1.0 eq) (example 2, step D), trimethyl-[2-[[5-(4,4,5,5-tetramethyl-1,3,2-dioxaborolan-2-yl)-2,3-dihydrobenzofuran-4-yl]oxymethoxy]ethyl]silane (208 mg. 0.530 mmol, 1.0 eq) (example 2, step C') and sat. aq. $Na_2CO_3$ (0.75 mL) were suspended in 1,4-dioxane (4 mL) and the reaction mixture was sparged with $N_2$, then evacuated and back-filled with $N_2$ (3×). XPhos Pd G3 (45 mg, 0.050 mmol, 0.10 eq) was added and the reaction mixture placed under $N_2$, then stirred at 80° C. for 24 h. The reaction mixture was diluted with EtOAc (50 mL) and washed with 1:1 water:brine (50 mL). The organic phase was filtered through Celite® and concentrated in vacuo. The resulting residue was purified by chromatography on silica gel (24 g column, 0-10% (0.7 N $NH_3$ in MeOH)/DCM) to afford the SEM protected product. This was taken up in DCM (6 mL) and TFA (3 mL) and stirred at room temperature for 3 h, before being concentrated in vacuo. The resulting residue was dissolved in MeOH (4 mL) and ethylenediamine (1 mL) was added. The mixture was stirred for 2 h, then concentrated in vacuo. The resulting residue was dissolved in 5 mL of DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH $C_{18}$ ODB prep column, 130 Å, 5 μm, 30 mm×100 mm, flow rate 40 mL min-1 eluting with a 0.1% formic acid in water-MeCN gradient over 12.5 mins using UV across all wavelengths with PDA as well as a QDA and ELS detector. At-column dilution pump gives 2 mL min-1 Methanol over the entire method, which is included in the following MeCN percentages. Gradient information: 0.0-0.5 min, 5% MeCN: 0.5-10.5 min, ramped from 5% MeCN to 15% MeCN: 10.5-10.6 min, ramped from 15% MeCN to 100% MeCN: 10.6-12.5 min, held at 100% MeCN. This afforded the title compound (47 mg, 23% yield) as a light brown solid. LCMS m/z 372.2 $[M+H]^+$, ESI pos.

Example 3: 3-[2-Hydroxy-4-(trifluoromethyl)phenyl]-4-methyl-6-[[(3R)-3-piperidyl]amino]-1,2,4-triazin-5-one;2,2,2-trifluoroacetic Acid

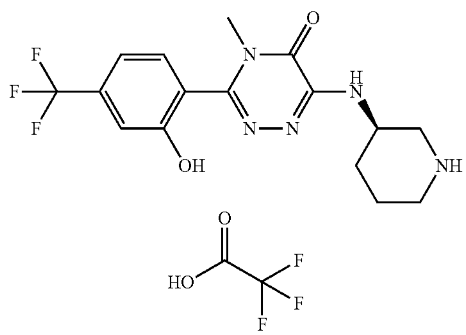

Step A: tert-Butyl-(R)-3-((3-(2-methoxy-4-(trifluoromethyl)phenyl)-4-methyl-5-oxo-4,5-dihydro-1,2,4-triazin-6-yl)amino)piperidine-1-carboxylate To a solution of 6-chloro-3-(2-methoxy-4-(trifluoromethyl)phenyl)-4-methyl-1,2,4-triazin-5(4H)-one (Example 1, step E) (50.0 mg, 0.16 mmol, 1.0 eq) in NMP (0.5 mL) was added DIEA (2.03 g, 1.56 mmol, 10.0 eq) and tert-butyl (R)-3-aminopiperidine-1-carboxylate (1.57 g, 0.78 mmol, 5.0 eq), then the reaction mixture was stirred at 100° C. for 2 hours in the microwave. The above reaction mixture was diluted with DMF (2 mL), and then purified by reverse phase column chromatography ($C_{18}$, 0.1% TFA in water/MeCN). Finally, the eluent was lyophilized to afford the title compound (50 mg, 65% yield) as a yellow solid. LC-MS (Method 1): m/z 484.0 $[M+H]^+$, ESI pos.

Step B: 3-[2-Hydroxy-4-(trifluoromethyl)phenyl]-4-methyl-6-[[(3R)-3-piperidyl]amino]-1,2,4-triazin-5-one;2,2,2-trifluoroacetic Acid To a solution of tert-butyl (R)-3-((3-(2-methoxy-4-(trifluoromethyl)phenyl)-4-methyl-5-oxo-4,5-dihydro-1,2,4-triazin-6-yl)amino)piperidine-1-carboxylate (Example 3. Step A) (40.0 mg, 0.08 mmol, 1.0 eq) in DCM (1 mL) was added $BBr_3$ (0.2 mL) at −40° C., then the reaction mixture was stirred at 20° C. for 1 hour under nitrogen atmosphere. The above reaction mixture was quenched with water (0.5 mL), the pH was adjusted to 8 with $NH_3 \cdot H_2O$, then concentrated under reduced pressure. The residue was dissolved in MeOH (2 mL) and then purified by reverse phase column chromatography ($C_{18}$, 0.1% TFA in water/MeCN). The eluent was lyophilized to afford the title compound (38.1 mg, 94% yield) as a yellow solid. LC-MS (Method 1): m/z 370.1 $[M+H]^+$, ESI pos.

Example 4: 3-[2-Hydroxy-4-(trifluoromethyl)phenyl]-4-methyl-6-[(8-methyl-8-azabicyclo[3.2.1]octan-2-yl)amino]-1,2,4-triazin-5-one;2,2,2-trifluoroacetic Acid

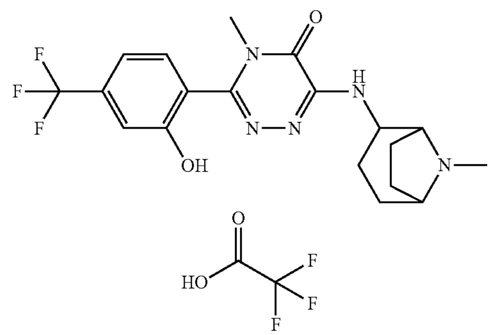

Step A: tert-butyl-(1R,2R,5R)-2-(((benzyloxy)carbonyl)amino)-8-azabicyclo[3.2.1]octane-8-carboxylate To a solution of benzyl alcohol (1.91 g, 17.6 mmol, 5.0 eq) in toluene (54 mL) was added TEA (7.12 g, 7.05 mmol, 2.0 eq) and DPPA (1.07 g, 3.88 mmol, 1.1 eq). The resulting reaction mixture was stirred at 80° C. for 4 hours, and then the commercially available 8-(1,1-dimethylethyl) 8-azabicyclo[3.2.1]octane-2,8-dicarboxylate (CAS #1366053-52-2, 900 mg, 3.53 mmol, 1.0 eq) was added and stirred at 70° C. for 12 hours under nitrogen atmosphere. The above reaction solution was diluted with water (100 mL), extracted with ethyl acetate (50 mL×3). The combined organic phase was washed with brine (100 mL), dried over anhydrous $Na_2SO_4$, filtered and the filtrate was concentrated under reduced pressure. The residue was purified by column chromatography (silica gel, petroleum ether:ethyl acetate=1:0 to 5:1) to afford the desired title compound (900 mg, 71% yield) as yellow oil. LC-MS (Method 1): m/z 359.2 $[M-H]^-$, ESI neg.

Step B: Benzyl ((1R,2R,5S)-8-azabicyclo[3.2.1]octan-2-yl)carbamate

To a solution of aforementioned tert-butyl-(1R,2R,5R)-2-(((benzyloxy)carbonyl)amino)-8-azabicyclo[3.2.1]octane-8-carboxylate (Example 4, step A) (800 mg, 2.22 mmol, 1.0 eq) in DCM (8 mL) was added TFA (16.0 mL, 208 mmol, 93.6 eq). The resulting reaction mixture was stirred at 20° C. for 1 hour, and then it was concentrated under reduced pressure to afford the title product (800 mg, 96% yield) as a yellow gum. LC-MS (Method 1): m/z 261.1 $[M+H]^+$, ESI pos.

Step C: Benzyl ((1R,2R,5R)-8-methyl-8-azabicyclo[3.2.1]octan-2-yl)carbamate

To a solution of aforementioned benzyl ((1R,2R,5S)-8-azabicyclo[3.2.1]octan-2-yl)carbamate (Example 4, step B) (800.0 mg, 2.14 mmol, 1.0 eq) in MeOH (16 mL) was added TEA (0.6 mL, 4.27 mmol, 2.0 eq), acetic acid (513.3 mg, 8.55 mmol, 4.0 eq), 4 Å molecular sieve (400 mg) and formaldehyde (1734.50 mg, 37% w/w in water, 21.4 mmol, 10 eq.). The reaction mixture was stirred at 20° C. for 0.5 hours, and then sodium cyanoborohydride (402.9 mg, 6.41 mmol, 3.0 eq) was added. The reaction mixture was stirred at 20° C. for 1 hour, then quenched with water (0.2 mL) and diluted with MeOH (5 mL), filtered and the filtrate was concentrated under reduced pressure. The residue was purified by reverse phase column chromatography ($C_{18}$, 0.1% $NH_3 \cdot H_2O$ in water/MeCN), then the eluent was lyophilized to afford the title compound (400 mg, 63% yield) as a yellow solid. LC-MS (Method 1): m/z 275.1 $[M+H]^+$, ESI pos.)

Step D: (1R,2R,5R)-8-Methyl-8-azabicyclo[3.2.1]octan-2-amine

To a solution of aforementioned benzyl (8-methyl-8-azabicyclo[3.2.1]octan-2-yl)carbamate (Example 4, step C) (200 mg, 0.73 mmol, 1.0 eq) in MeOH (2 mL) was added Pd/C (40.0 mg), then the reaction mixture was degassed and purged with hydrogen three times and stirred at 20° C. for 2 hours under hydrogen atmosphere (760 mmHg). The reaction mixture was filtered and the filtrate was concentrated under reduced pressure to afford the title compound (100 mg, 98% yield) as a yellow solid. LC-MS (Method 1): m/z 141.2 $[M+H]^+$, ESI pos.

Step E: 3-[2-Methoxy-4-(trifluoromethyl)phenyl]-4-methyl-6-[[(8-methyl-8-azabicyclo[3.2.1]octan-2-yl]amino]-1,2,4-triazin-5-one To a solution of aforementioned 6-chloro-3-(2-methoxy-4-(trifluoromethyl)phenyl)-4-methyl-1,2,4-triazin-5(4H)-one (Example 1, step E) (50.0 mg, 0.16 mmol, 1.0 eq) in NMP (0.1 mL) was added DIEA (100.0 mg, 0.77 mmol, 4.92 eq), and aforementioned 8-methyl-8-azabicyclo[3.2.1]octan-2-amine (Example 4, step C) (50.0 mg, 0.36 mmol, 2.28 eq). The mixture was stirred at 130° C. for 2 hours under microwave condition. The reaction was diluted with DMF (2 mL), filtered and the filtrate was purified by reversed-phase column chromatography ($C_{18}$, 0.1% TFA in water-MeCN), then the eluent was lyophilized to the title compound (5 mg, 7% yield) as a yellow solid. LC-MS (Method 1): m/z 424.1 $[M+H]^+$, ESI pos.

Step F: 3-[2-Hydroxy-4-(trifluoromethyl)phenyl]-4-methyl-6-[[(2R)-8-methyl-8-azabicyclo[3.2.1]octan-2-yl]amino]-1,2,4-triazin-5-one;2,2,2-trifluoroacetic Acid To a solution of 6-((8-azabicyclo[3.2.1]octan-2-yl)amino)-3-(2-methoxy-4-(trifluoromethyl)phenyl)-4-methyl-1,2,4-triazin-5(4H)-one (Example 4, step E) (5.0 mg, 0.01 mmol, 1.0 eq) in DCM (1 mL) was added $BBr_3$ (50.0 mg, 0.2 mmol, 16.94 eq) portion wise at −40° C., then the mixture was stirred at 20° C. for 1 hour. The mixture was quenched with water (0.5 mL), then the pH was adjusted to 8 with $NH_3 \cdot H_2O$, dissolved with MeOH (1 mL), then purified by reverse phase column chromatography ($C_{18}$, 0.1% TFA in water/MeCN). The eluent was lyophilized to afford the title compound (1.21 mg, 18% yield) as yellow oil. LC-MS (Method 1): m/z 410.2 $[M+H]^+$, ESI pos.

Example 5: (R)-6-((1-(Cyclopropylmethyl)piperidin-3-yl)amino)-3-(2-hydroxy-4-(trifluoromethyl)phenyl)-4-methyl-1,2,4-triazin-5(4H)-one;2,2,2-trifluoroacetic Acid

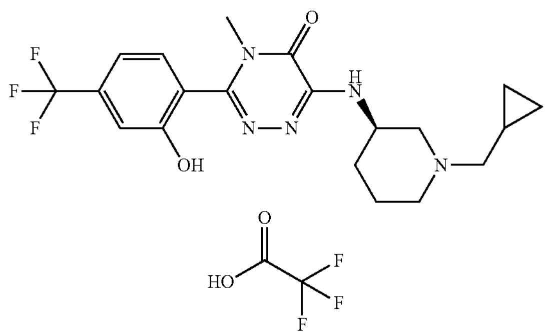

Step A: tert-Butyl (R)-(1-(cyclopropylmethyl)piperidin-3-yl)carbamate

To a mixture of commercially available tert-butyl (R)-piperidin-3-ylcarbamate (CAS #309956-78-3, 1.0 g, 4.99 mmol, 1.0 eq), (bromomethyl)cyclopropane (0.48 mL, 4.99 mmol, 1.0 eq) in MeCN (10 mL) was added $K_2CO_3$ (7.58 g, 5.49 mmol, 1.1 eq) at 25° C., the reaction mixture was stirred for 2 hours under $N_2$. LC-MS showed the desired mass was detected. The mixture was poured into water (20 mL) and extracted with ethyl acetate (100 mL×3). The combined organic layers were washed with brine (20 mL), dried over anhydrous $Na_2SO_4$, filtered and the filtrate was concentrated under reduced pressure. The crude product was purified by reversed-phase column chromatography ($C_{18}$, 0.1% TFA in water/MeCN condition); the eluent was lyophilized to afford the title compound (300 mg, 24% yield) as an off-white solid. LC-MS (Method 2): m/z 255.6 $[M+H]^+$, ESI pos.

Step B: (R)-1-(Cyclopropylmethyl)piperidin-3-amine

To a mixture of aforementioned tert-butyl N-[(3R)-1-(cyclopropylmethyl)-3-piperidyl]carbamate (Example 5, step A) (150 mg, 0.59 mmol, 1.0 eq) in EtOAc (2 mL) was added another solution of HCl in EtOAc (2.0 mL, 8.0 mmol, 4 M, 13.6 eq) at 25° C., the reaction mixture was stirred at 25° C. for 2 hours. The mixture was concentrated under reduced pressure to give the crude product, then dissolved in water (5 mL), adjusted to pH~8 by sat. $Na_2CO_3$ solution. The solution was lyophilized and then triturated with DCM (30 mL), filtrated and the filtrate was concentrated under reduced pressure to afford the title compound (70.0 mg, 77% yield) as yellow oil. $^1$H NMR (400 MHz, $CD_3OD$): δ 3.22-3.20 (m, 1H), 3.08-2.95 (m, 1H), 2.85-2.90 (m, 1H), 2.33-2.31 (m, 2H), 2.24-2.22 (m, 1H), 2.02-1.98 (m, 1H), 1.78-1.88 (m, 1H), 1.75-1.73 (m, 1H), 1.66-1.54 (m, 1H), 1.27-1.24 (m, 1H), 0.90-0.80 (m, 1H), 0.57-0.50 (m, 2H), 0.15-0.14 (m, 2H).

Step C: (R)-6-((1-(Cyclopropylmethyl)piperidin-3-yl)amino)-3-(2-methoxy-4-(trifluoromethyl)phenyl)-4-methyl-1,2,4-triazin-5(4H)-one To a mixture of aforementioned 6-chloro-3-(2-methoxy-4-(trifluoromethyl)phenyl)-4-methyl-1,2,4-triazin-5(4H)-one (Example 1, step E) (30.0 mg, 0.09 mmol, 1.0 eq) and (R)-1-(cyclopropylmethyl)piperidin-3-amine (Example 5, step B) (70.0 mg, 0.45 mmol, 4.84 eq) in NMP (1 mL) was added DIEA (60.6 mg, 0.47 mmol, 5.0 eq). The mixture was stirred at 90° C. for 2 hours under nitrogen atmosphere. LC-MS showed the desired mass was detected. The mixture was concentrated in vacuum. The residue to give was purified by reversed-phase column chromatography ($C_{18}$, 0.1% TFA in water/MeCN condition), the eluent was lyophilized to afford the title compound (30.0 mg, 73% yield) as a yellow solid. LC-MS (Method 2): m/z 438.0 [M+H]$^+$, ESI pos.

Step D: (R)-6-((1-(Cyclopropylmethyl)piperidin-3-yl)amino)-3-(2-hydroxy-4-(trifluoromethyl)phenyl)-4-methyl-1,2,4-triazin-5(4H)-one;2,2,2-trifluoroacetic Acid To a mixture of aforementioned (R)-6-((1-(cyclopropylmethyl)piperidin-3-yl)amino)-3-(2-methoxy-4 (trifluoromethyl)phenyl)-4-methyl-1,2,4-triazin-5(4H)-one (Example 5, step C) (30.0 mg, 0.07 mmol, 1.0 eq) in DCM (2 mL) was added boron tribromide (687.2 mg, 2.74 mmol, 40.0 eq) portion wise, the reaction mixture was stirred at −60° C. for 10 minutes, then stirred at 25° C. for 50 minutes, LC-MS showed desired mass was detected, The mixture was adjusted to pH~7 by $NH_3 \cdot H_2O$, then filtered and filtrate was concentrated in vacuum. The crude product was purified by reversed-phase column chromatography ($C_{18}$, 0.1% TFA in water/MeCN condition), the eluent was lyophilized to afford the title compound (5.67 mg, 13% yield) as a yellow solid. LC-MS (Method 2): m/z 423.9 [M+H]$^+$, ESI pos.

Example 6: (R)-3-(2-Hydroxy-4-(trifluoromethyl)phenyl)-4-methyl-6-((1-methylpiperidin-3-yl)amino)-1,2,4-triazin-5(4H)-one;2,2,2-trifluoroacetic Acid

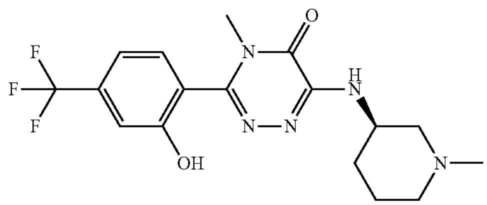

-continued

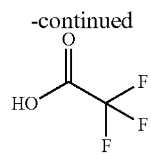

Step A: (R)-3-(2-Methoxy-4-(trifluoromethyl)phenyl)-4-methyl-6-((1-methylpiperidin-3-yl)amino)-1,2,4-triazin-5(4H)-one To a mixture of 6-chloro-3-(2-methoxy-4-(trifluoromethyl)phenyl)-4-methyl-1,2,4-triazin-5(4H)-one (Example 1, step E) (40.0 mg, 0.13 mmol, 1.0 eq) and ((R)-1-methylpiperidin-3-amine (71.4 mg, 0.63 mmol, 5 eq) in NMP (1 mL) was added DIEA (80.86 mg, 0.63 mmol, 5.0 eq). The reaction mixture was stirred at 90° C. for 2 hours. The mixture was concentrated in vacuum. The residue was purified by reversed-phase column chromatography ($C_{18}$, 0.1% TFA in water/MeCN condition), then the fraction was lyophilized to afford the title compound (30.0 mg, 60% yield) as a white solid. LC-MS (Method 2): m/z 398.2 [M+H]$^+$, ESI pos.

Step B: (R)-3-(2-Hydroxy-4-(trifluoromethyl)phenyl)-4-methyl-6-((1-methylpiperidin-3-yl)amino)-1,2,4-triazin-5(4H)-one;2,2,2-trifluoroacetic Acid A mixture of aforementioned (R)-3-(2-methoxy-4-(trifluoromethyl)phenyl)-4-methyl-6-((1-methylpiperidin-3-yl) amino)-1,2,4-triazin-5(4H)-one (Example 6, step A) (30.0 mg, 0.08 mmol, 1.0 eq) and boron tribromide (189.12 mg, 0.75 mmol, 10.0 eq) in DCM (1 mL) was stirred at −60° C. for 10 minutes, then stirred at 25° C. for 50 minutes. The mixture was adjusted to pH~7 by $NH_3 \cdot H_2O$, then filtered and the filtrate was concentrated in vacuum. The crude product was purified by reversed-phase column chromatography ($C_{18}$, 0.1% TFA in water/MeCN condition), then the eluent was lyophilized to afford the title product (5.48 mg, 14% yield) as a yellow solid. LC-MS (Method 2): m/z 384.1 [M+H]$^+$, ESI pos.

Example 7: 6-(1,2,3,5,6,7,8,8a-Octahydroindolizin-8-ylamino)-3-[2-hydroxy-4-(trifluoromethyl)phenyl]-4-methyl-1,2,4-triazin-5-one;2,2,2-trifluoroacetic Acid

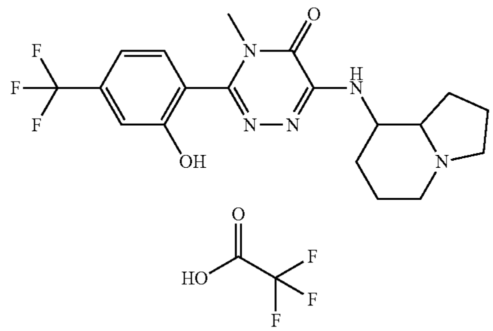

Step A: 6,7-Dihydroindolizin-8(5H)-one Oxime

To a solution of commercially available 6,7-dihydroindolizin-8(5H)-one (CAS #54906-44-4, 400.0 mg, 2.96 mmol, 1.0 eq) in ethanol (6 mL) and water (2 mL) was added hydroxylamine hydrochloride (617 mg, 8.88 mmol, 3.0 eq) and $NaOAc \cdot 3H_2O$ (1.21 g, 8.88 mmol, 3.0 eq), then stirred at 100° C. for 4 hours. The above reaction solution was cooled to room temperature and plenty of solid formed, then filtered and the solid was dried under reduced pressure to afford the title compound (300 mg, 67% yield) as a yellow solid. LC-MS (Method 1): m/z 151.1 $[M+H]^+$, ESI pos.

Step B: Octahydroindolizin-8-amine

To a solution of aforementioned 6,7-dihydroindolizin-8 (5H)-one oxime (Example 7, step A) (300 mg, 2.0 mmol, 1.0 eq) in MeOH (10 mL) was added Pd/C (100.0 mg) and concentrated HCl (1.97 g. 2.0 mmol, 1.0 eq). The reaction mixture was degassed and purged with hydrogen three times and then stirred at 20° C. for 12 hours under hydrogen atmosphere (760 mmHg). The above reaction mixture was filtered and the filtrate was concentrated under reduced pressure. The residue was diluted with MeOH (20 mL), the pH was adjusted to 8 with a saturated aq. solution of sodium bicarbonate, then the solution was lyophilized to give a yellow solid, which was triturated with a mixture of DCM (20 mL) and MeOH (2 mL) and finally filtered. The filtrate was concentrated under reduced pressure to afford the title compound (200 mg, 71% yield) as black oil. $^1H$ NMR (400 MHZ, MeOH-$d_4$) δ 3.79-3.51 (m, 3H), 3.46-3.36 (m, 1H), 3.26-3.01 (m, 2H), 2.57-2.41 (m, 1H), 2.37-2.28 (m, 1H), 2.25-2.09 (m, 3H), 2.08-1.93 (m, 2H), 1.90-1.70 (m, 1H).

Step C: 3-(2-Methoxy-4-(trifluoromethyl)phenyl)-4-methyl-6-((octahydroindolizin-8-yl)amino)-1,2,4-triazin-5(4H)-one To a solution of aforementioned 6-chloro-3-(2-methoxy-4-(trifluoromethyl)phenyl)-4-methyl-1,2,4-triazin-5(4H)-one (Example 1, step E) (100 mg, 0.31 mmol, 1.0 eq) and aforementioned octahydroindolizin-8-amine (Example 7, step B) (132 mg, 0.94 mmol, 3.0 eq) in NMP (0.5 mL) was added DIEA (406.7 mg, 3.13 mmol, 10.0 eq). The mixture was stirred at 100° C. for 2 hours under microwave condition. The above reaction was diluted with DMF (2 mL), filtered and the filtrate was purified by reverse phase flash (0.1% TFA in water-MeCN), then the eluent was lyophilized to afford the title compound (60 mg, 44.4% yield) as a yellow solid. LC-MS (Method 1): m/z 424.1 $[M+H]^+$, ESI pos.

Step D: 6-(1,2,3,5,6,7,8,8a-Octahydroindolizin-8-ylamino)-3-[2-hydroxy-4-(trifluoromethyl)phenyl]-4-methyl-1,2,4-triazin-5-one;2,2,2-trifluoroacetic Acid To a solution of aforementioned 3-(2-methoxy-4-(trifluoromethyl)phenyl)-4-methyl-6-((octahydroindolizin-8-yl)amino)-1,2,4-triazin-5(4H)-one (Example 7, step C) (30.0 mg, 0.07 mmol, 1.0 eq) in DCM (1 mL) was added $BBr_3$ (88.7 mg, 0.35 mmol, 5.0 eq) drop wise at −40° C., then stirred at 20° C. for 1 hour. The above reaction mixture was quenched with water (0.5 mL). The pH was adjusted to 8 with $NH_3 \cdot H_2O$, dissolved in MeOH (1 mL), then purified by reverse phase column chromatography ($C_{18}$, 0.1% TFA in water/MeCN). Afterwards, the eluent was lyophilized to afford the title compound (8.74 mg, 22% yield) as yellow oil. LC-MS (Method 1): m/z 410.0 $[M+H]^+$, ESI pos.

Example 8: 3-[2-Hydroxy-4-(trifluoromethyl)phenyl]-4-methyl-6-[[(3R)-1-propyl-3-piperidyl]amino]-1,2,4-triazin-5-one;2,2,2-trifluoroacetic Acid

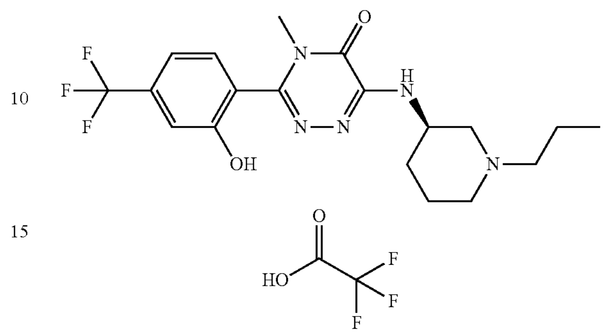

To a solution of (R)-3-(2-hydroxy-4-(trifluoromethyl)phenyl)-4-methyl-6-(piperidin-3-ylamino)-1,2,4-triazin-5(4H)-one (Example 3, step B) (15.0 mg, 0.03 mmol, 1.0 eq) in ethanol (1 mL) was added DIEA (8.01 mg, 0.06 mmol, 2.0 eq), followed by 1-bromopropane (38.2 mg, 0.31 mmol, 10.0 eq) was added at 0° C. dropwise, then the reaction was stirred at 50° C. for 4 hours under nitrogen atmosphere. The reaction solution was concentrated under reduced pressure to give yellow oil, which was purified by preparative HPLC (column Phenomenex Synergi Polar-RP 100*25 mm*4 μm; Condition: water (TFA)-MeCN)), then the eluent was lyophilized to afford the title compound (3.96 mg, 23% yield) as yellow oil. LC-MS (Method 1): m/z 411.9 $[M+H]^+$, ESI pos.

Example 9: 3-[2-Hydroxy-4-(trifluoromethyl)phenyl]-4-methyl-6-[(1,5,5-trimethyl-3-piperidyl)amino]-1,2,4-triazin-5-one;2,2,2-trifluoroacetic Acid

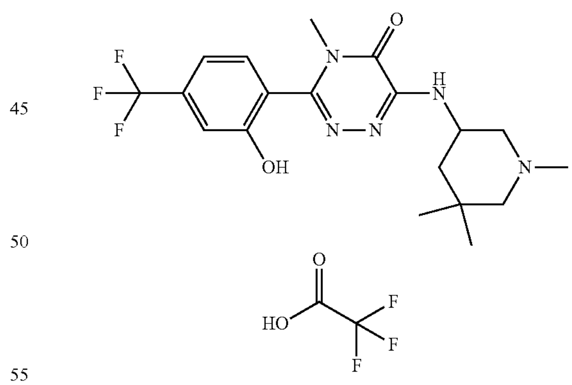

Step A: tert-Butyl 5-((3-(2-methoxy-4-(trifluoromethyl)phenyl)-4-methyl-5-oxo-4,5-dihydro-1,2,4-triazin-6-yl)amino)-3,3-dimethylpiperidine-1-carboxylate To a solution of aforementioned 6-chloro-3-(2-methoxy-4-(trifluoromethyl)phenyl)-4-methyl-1,2,4-triazin-5(4H)-one (Example 1, step E) (100 mg, 0.31 mmol, 1.0 eq) and commercially available tert-butyl 5-amino-3,3-dimethylpiperidine-1-carboxylate (CAS #1896921-12-2, 100 mg, 0.44 mmol, 1.4 eq) in 1,4-dioxane (2 mL) was added $Cs_2CO_3$ (255 mg, 0.78 mmol, 2.5 eq) and $BinapPdG_3$ (62.1 mg, 0.06 mmol, 0.2 eq). The mixture was stirred at 80° C. for 2 hours under $N_2$. The above reaction solution was diluted with water (50 mL), extracted with ethyl acetate (20 mL×3). The combined organic phase was washed with brine (50 mL), dried over anhydrous $Na_2SO_4$, filtered and the filtrate was concentrated under reduced pressure. The residue was purified by column chromatography ($SiO_2$, petroleum ether: ethyl acetate=1:0 to 2:1) to afford the title compound (70 mg, 39% yield) as a yellow solid. LC-MS (Method 1): m/z 512.0 $[M+H]^+$, ESI pos.

Step B: 6-((5,5-Dimethylpiperidin-3-yl)amino)-3-(2-methoxy-4-(trifluoromethyl)phenyl)-4-methyl-1,2,4-triazin-5(4H)-one To a solution of aforementioned tert-butyl 5-((3-(2-methoxy-4-(trifluoromethyl)phenyl)-4-methyl-5-oxo-4,5-dihydro-1,2,4-triazin-6-yl)amino)-3,3-dimethylpiperidine-1-carboxylate (Example 9, step A) (60.0 mg, 0.12 mmol, 1.0 eq) in DCM (1 mL) was added TFA (6.0 mL, 77.9 mmol, 664 eq), then the reaction mixture was stirred at 20° C. for 1 hour. The reaction solution was concentrated under reduced pressure to afford the title compound (60 mg, 97% yield) as yellow oil. LC-MS (Method 1): m/z 411.9 $[M+H]^+$, ESI pos.

Step C: 3-(2-Methoxy-4-(trifluoromethyl)phenyl)-4-methyl-6-((1,5,5-trimethylpiperidin-3-yl)amino)-1,2,4-triazin-5(4H)-one To a solution of aforementioned 6-((5,5-dimethylpiperidin-3-yl)amino)-3-(2-methoxy-4-(trifluoromethyl)phenyl)-4-methyl-1,2,4-triazin-5(4H)-one (Example 9, step B) (60.0 mg, 0.11 mmol, 1.0 eq) in ethanol (2 mL) was added DIEA (73.7 mg, 0.57 mmol, 5.0 eq) and iodomethane (16.2 mg, 0.11 mmol, 1.0 eq) drop wise, then the reaction mixture was stirred at 20° C. for 2 hours. The reaction mixture was purified directly by reversed-phase column chromatography ($C_{18}$, 0.1% $NH_3{\cdot}H_2O$ in water/MeCN), and then the eluent was lyophilized to afford the title compound (25 mg, 51% yield) as a yellow solid. LC-MS (Method 1): m/z 426.0 $[M+H]^+$, ESI pos.

Step D: 3-[2-Hydroxy-4-(trifluoromethyl)phenyl]-4-methyl-6-[(1,5,5-trimethyl-3-piperidyl)amino]-1,2,4-triazin-5-one;2,2,2-trifluoroacetic Acid To a solution of aforementioned 3-(2-methoxy-4-(trifluoromethyl)phenyl)-4-methyl-6-((1,5,5-trimethyl piperidin-3-yl)amino)-1,2,4-triazin-5(4H)-one (Example 9, step C) (20.0 mg, 0.05 mmol, 1.0 eq) in DCM (1 mL) was added $BBr_3$ (0.5 mL) at −40° C., then stirred at 20° C. for 1 hour under $N_2$. The reaction mixture was quenched with water (0.5 mL) at 0° C., diluted with MeOH (1 mL), then the pH was adjusted to 7 with ammonium hydroxide, purified by reversed-phase column chromatography ($C_{18}$, 0.1% TFA in water/MeCN). The eluent was lyophilized to afford the title compound (10.4 mg, 40% yield) as a yellow solid. LC-MS (Method 1): m/z 411.9 $[M+H]^+$, ESI pos.

Example 10: (R)-6-((1-Cyclopropylpiperidin-3-yl)amino)-3-(2-hydroxy-4-(trifluoromethyl)phenyl)-4-methyl-1,2,4-triazin-5(4H)-one

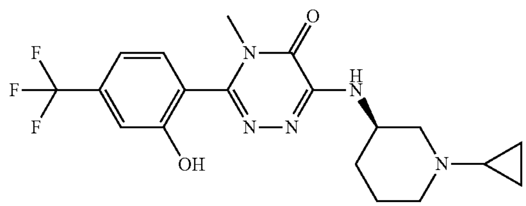 [SMILES: Cn1c(-c2ccc(C(F)(F)F)cc2O)nnc(N[C@@H]2CCCN(C3CC3)C2)c1=O]

Step A: tert-Butyl (R)-(1-cyclopropylpiperidin-3-yl)carbamate

To a solution of commercially available tert-butyl (R)-piperidin-3-ylcarbamate (CAS #184637-48-7, 1.0 g, 4.99 mmol, 1.0 eq) in MeOH (40 mL) and acetic acid (5 mL) was added $NaBH_3CN$ (1.57 g, 24.9 mmol, 5.0 eq) and (1-ethoxycyclopropoxy)trimethylsilane (1.74 g, 9.99 mmol, 2.0 eq) at 0° C. Then the mixture was stirred at 65° C. for 12 hours. The reaction was cooled to 20° C., diluted with water (200 mL) and extracted with DCM (40 mL×3). The organic layer was washed with a saturated $Na_2CO_3$ aq. solution (60 mL), dried over anhydrous $Na_2SO_4$, filtered and the filtrate was concentrated under vacuum. The residue was purified by silica gel column chromatography (PE:EtOAc=10:1~2:1) to afford the title compound (700 mg, 58% yield) as a white solid. $^1H$ NMR (400 MHZ, $CDCl_3$) δ 5.23-4.75 (m, 1H), 3.80-3.60 (m, 1H), 2.80-2.10 (m, 4H), 1.75-1.25 (m, 13H), 0.75-0.25 (m, 4H).

Step B: (1R)-1-cyclopropylpiperidin-3-amine;2,2,2-trifluoroacetic Acid

To a solution of aforementioned tert-butyl (R)-(1-cyclopropylpiperidin-3-yl)carbamate (Example 10, step A) (600 mg, 2.5 mmol, 1.0 eq) in DCM (5 mL) was added 2,2,2-trifluoroacetic acid (2.0 mL). The mixture was stirred at 20° C. for 1 hour. The reaction mixture was concentrated under reduced pressure to afford the title compound (919 mg, 100% yield) as colourless oil, which was used directly in next step without further purification. LC-MS (Method 2): m/z 141.29 $[M+H]^+$, ESI pos.

Step C: (R)-6-((1-Cyclopropylpiperidin-3-yl)amino)-3-(2-methoxy-4-(trifluoromethyl)phenyl)-4-methyl-1,2,4-triazin-5(4H)-one To a solution of aforementioned (R)-1-cyclopropylpiperidin-3-amine;2,2,2-trifluoroacetic acid (Example 10, step B) (273 mg, 0.74 mmol, 3.0 eq) in 1-butanol (2 mL) was added DIEA (319.4 mg, 2.47 mmol, 10.0 eq) and aforementioned 6-chloro-3-(2-methoxy-4-(trifluoromethyl)phenyl)-4-methyl-1,2,4-triazin-5(4H)-one (Example 1, step E) (79.0 mg, 0.25 mmol, 1.0 eq). The mixture was stirred at 110° C. for 3 hours. The reaction solution was filtered and the filtrate was purified by reversed-phase column chromatography ($C_{18}$, 0.1% in TFA/MeCN), and the eluent was lyophilized to afford the title compound (90 mg, 68% yield) as yellow gum. LC-MS (Method 2): m/z 424.1 $[M+H]^+$, ESI pos.

Step D: (R)-6-((1-Cyclopropylpiperidin-3-yl)amino)-3-(2-hydroxy-4-(trifluoromethyl)phenyl)-4-methyl-1,2,4-triazin-5(4H)-one To a solution of aforementioned (R)-6-((1-cyclopropylpiperidin-3-yl)amino)-3-(2-methoxy-4-(trifluoromethyl)phenyl)-4-methyl-1,2,4-triazin-5(4H)-one (Example 10, step C) (90.0 mg, 0.17 mmol, 1.0 eq) in DCM (2 mL) was added $BBr_3$ (210 mg, 0.84 mmol, 5.0 eq) at −60° C. The mixture was warmed to 20° C. and stirred for 1 hour. The reaction was quenched with water (1 mL), adjusted to pH~8 with $NH_3{\cdot}H_2O$ and concentrated under reduced pressure. The residue was purified by Prep-HPLC (column: waters Xbridge 150*25 mm*5 μm; Condition: water ($NH_4HCO_3$)/MeCN). The eluent was lyophilized to afford the title compound (15.7 mg, 22% yield) as white solid. LC-MS (Method 2): m/z 410.29 $[M+H]^+$, ESI pos.

Example 11: 6-(((1S,3S)-3-Hydroxy-3-methylcyclobutyl)amino)-3-(2-hydroxy-4-(trifluoromethyl)phenyl)-4-methyl-1,2,4-triazin-5(4H)-one

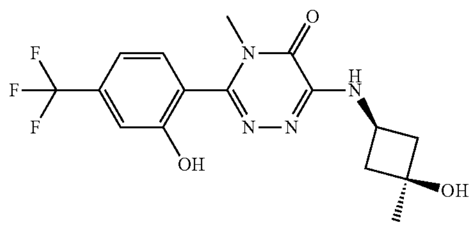 [SMILES: Cn1c(-c2ccc(C(F)(F)F)cc2O)nnc(N[C@H]2C[C@@](C)(O)C2)c1=O]

Step A: 6-(((1S,3S)-3-Hydroxy-3-methylcyclobutyl)amino)-3-(2-methoxy-4-(trifluoromethyl)phenyl)-4-methyl-1,2,4-triazin-5(4H)-one To a mixture of 6-chloro-3-(2-methoxy-4-(trifluoromethyl)phenyl)-4-methyl-1,2,4-triazin-5(4H)-one (Example 1, step E) (200.0 mg, 0.45 mmol, 1.0 eq) and commercially available (1S,3S)-3-amino-1-methylcyclobutane-1-ol hydrochloride (CAS #1523606-23-6, 125 mg, 0.90 mmol, 2 eq) in NMP (3 mL) was added DIEA (175.3 mg, 1.36 mmol, 3.0 eq). The mixture was stirred at 95° C. for 2 hours. LC-MS showed the desired mass was detected. The mixture was concentrated in vacuum. The residue was purified by reversed-phase column chromatography ($C_{18}$, 0.1% $NH_3{\cdot}H_2O$ in water/MeCN condition), the eluent was lyophilized to yield the title compound (70.0 mg, 37% yield) as a white solid. LC-MS (Method 2): m/z 385.1 $[M+H]^+$, ESI pos.

Step B: 6-(((1S,3S)-3-Hydroxy-3-methylcyclobutyl)amino)-3-(2-hydroxy-4-(trifluoromethyl)phenyl)-4-methyl-1,2,4-triazin-5(4H)-one To a mixture of aforementioned 6-(((1S,3S)-3-hydroxy-3-methylcyclobutyl)amino)-3-(2-methoxy-4-(trifluoro methyl)phenyl)-4-methyl-1,2,4-triazin-5(4H)-one (Example 11, step A) (70.0 mg, 0.18 mmol, 1.0 eq) in DCM (2 mL) was added boron tribromide (456.3 mg, 1.82 mmol, 10.0 eq). The reaction mixture was stirred at −60° C. for 10 minutes, and then stirred at 25° C. for 50 minutes. LC-MS showed desired mass was detected. The mixture was adjusted to pH~7 by $NH_3{\cdot}H_2O$, then filtered and filtrate was concentrated in vacuum. The crude product was purified by reversed-phase column chromatography ($C_{18}$, 0.1% $NH_3{\cdot}H_2O$ in water/MeCN condition), the eluent was lyophilized to afford the title compound (3.94 mg, 6% yield) as a light yellow solid. LC-MS (Method 2): m/z 371.0 $[M+H]^+$, ESI pos.

Example 12: 6-[(1-tert-Butyl-3-piperidyl)amino]-3-[2-hydroxy-4-(trifluoromethyl)phenyl]-4-methyl-1,2,4-triazin-5-one;2,2,2-trifluoroacetic Acid

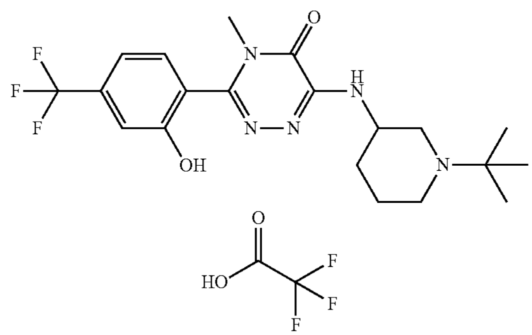

Step A: 6-[(1-tert-Butyl-3-piperidyl)amino]-3-[2-methoxy-4-(trifluoromethyl)phenyl]-4-methyl-1,2,4-triazin-5-one To a mixture of 6-chloro-3-(2-methoxy-4-(trifluoromethyl)phenyl)-4-methyl-1,2,4-triazin-5(4H)-one (Example 1, step E) (100.0 mg, 0.23 mmol, 1.0 eq) and 1-tert-butylpiperidin-3-amine;hydrochloride (131 mg, 0.68 mmol, 3.0 eq) in NMP (1 mL) was added DIEA (87.7 mg, 0.68 mmol, 3.0 eq). The reaction mixture was stirred at 95° C. for 2 hours under $N_2$. LC-MS showed the desired mass was detected. The mixture was concentrated in vacuum to give the crude product, which was purified by reversed-phase column chromatography ($C_{18}$, 0.1 TFA in water/MeCN condition), the eluent was lyophilized to afford the title compound (45.0 mg, 44% yield) as a white solid. LC-MS (Method 2): m/z 440.1 $[M+H]^+$, ESI pos.

Step B: 6-[(1-tert-Butyl-3-piperidyl)amino]-3-[2-hydroxy-4-(trifluoromethyl)phenyl]-4-methyl-1,2,4-triazin-5-one;2,2,2-trifluoroacetic Acid To a mixture of 6-[(1-tert-butyl-3-piperidyl)amino]-3-[2-methoxy-4-(trifluoromethyl)phenyl]-4-methyl-1,2,4-triazin-5-one (45.0 mg, 0.1 mmol, 1.0 eq) in DCM (2 mL) was added boron tribromide (128 mg, 0.51 mmol, 5.0 eq), the reaction mixture was stirred at −60° C. for 10 minutes, then stirred at 25° C. for 50 minutes under $N_2$. LC-MS showed desired mass was detected. The mixture was adjusted to pH~7 by $NH_3{\cdot}H_2O$, then filtered and filtrate was concentrated in vacuum. The residue was purified by reversed-phase column chromatography ($C_{18}$, 1% TFA in water/MeCN condition) and the eluent was lyophilized to afford the title compound (24.6 mg, 43% yield) as a light yellow solid. LC-MS (Method 2): m/z 426.2 $[M+H]^+$, ESI pos.

Example 13: 6-(2-Azabicyclo[2.2.1]heptan-6-ylamino)-3-[2-hydroxy-4-(trifluoromethyl)phenyl]-4-methyl-1,2,4-triazin-5-one;2,2,2-trifluoroacetic Acid

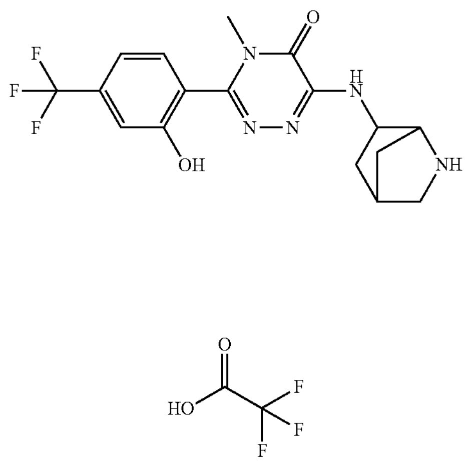

Step A: tert-Butyl 6-((3-(2-methoxy-4-(trifluoromethyl)phenyl)-4-methyl-5-oxo-4,5-dihydro-1,2,4-triazin-6-yl)amino)-2-azabicyclo[2.2.1]heptane-2-carboxylate To a mixture of aforementioned 6-chloro-3-(2-methoxy-4-(trifluoromethyl)phenyl)-4-methyl-1,2,4-triazin-5(4H)-one (Example 1, step E) (48.2 mg, 0.15 mmol, 0.2 eq) in NMP (0.5 mL) was added DIEA (195 mg, 1.51 mmol, 2.0 eq) and commercially available tert-butyl 6-amino-2-azabicyclo[2.2.1]heptane-2-carboxylate (CAS #1005077-74-6, 160 mg, 0.75 mmol, 1.0 eq) in a microwave tube. Then the mixture was stirred at 130° C. for 2 hours under microwave atmosphere. The reaction mixture was quenched by addition of water (5 mL). The residue was purified by reverse phase column chromatography ($C_{18}$, 0.1% TFA in water/MeCN condition) to yield the title compound (30.0 mg, 8% yield) as yellow oil. LC-MS (Method 2): m/z 496.2 $[M+H]^+$, ESI pos.

Step B: 6-(2-Azabicyclo[2.2.1]heptan-6-ylamino)-3-[2-hydroxy-4-(trifluoromethyl)phenyl]-4-methyl-1,2,4-triazin-5-one;2,2,2-trifluoroacetic Acid To a mixture of aforementioned tert-butyl 6-[[3-[2-methoxy-4-(trifluoromethyl)phenyl]-4-methyl-5-oxo-1,2,4-triazin-6-yl]amino]-2-azabicyclo[2.2.1]heptane-2-carboxylate (Example 13, step A) (30.0 mg, 0.06 mmol, 1.0 eq) in DCM (1 mL) was added $BBr_3$ (1.51 mg, 0.61 mmol, 10.0 eq) at −60° C. under $N_2$, and the mixture was stirred at −60° C. for 10 minutes, then stirred at 25° C. for 1 hour. The reaction mixture was quenched by addition of ice water (2 mL) and adjusted to pH~7 with $NH_3 \cdot H_2O$ solution. The mixture was purified by reverse phase column chromatography ($C_{18}$, 0.1% TFA in water/MeCN condition) to afford the title compound (10.7 mg, 43% yield) as a yellow solid. LC-MS (Method 2): m/z 382.1 $[M+H]^+$, ESI pos.

Example 14: 6-[[(3R,5S)-1-Ethyl-5-methyl-3-piperidyl]amino]-3-[2-hydroxy-4-(trifluoromethyl)phenyl]-4-methyl-1,2,4-triazin-5-one;2,2,2-trifluoroacetic Acid

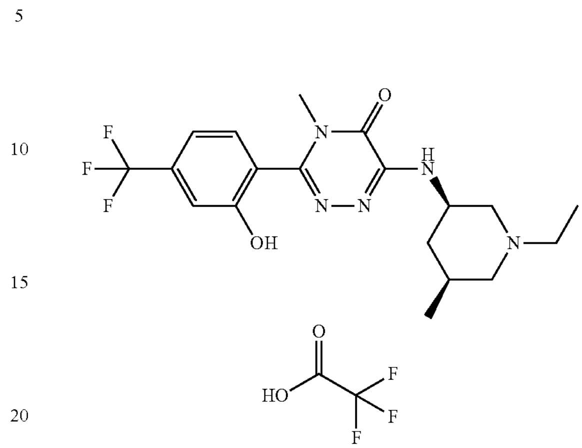

Step A: tert-Butyl ((3R,5S)-1-ethyl-5-methylpiperidin-3-yl)carbamate

To a solution of commercially available tert-butyl ((3R,5S)-5-methylpiperidin-3-yl)carbamate (CAS #1187055-56-6, 250 mg, 1.17 mmol, 1.0 eq) in MeCN (2.5 mL) was added $K_2CO_3$ (323 mg, 2.33 mmol, 2.0 eq) and ethyl bromide (0.1 mL, 1.28 mmol, 1.1 eq). The reaction mixture was stirred at 25° C. for 12 hours under $N_2$. Then, the reaction mixture was filtrated and the filtrate was concentrated under reduced pressure, the residue was purified by column chromatography on silica gel (DCM:MeOH=10:1, $R_f$=0.2) to afford the title compound (85.0 mg, 31% yield) as a white solid. $^1H$ NMR (400 MHZ, MeOD-$d_4$) δ 3.81-3.55 (m, 1H), 3.10-3.07 (m, 1H), 2.88-2.84 (m, 1H), 2.51-2.42 (m, 2H), 1.91 (d, 1H), 1.77-1.69 (m, 1H), 1.61 (t, 1H), 1.51 (t, 1H), 1.43 (s, 9H), 1.10 (t, 3H), 0.92 (d, 3H), 0.82 (q, 1H).

Step B: (3R,5S)-1-Ethyl-5-methylpiperidin-3-amine; 2,2,2-trifluoroacetic Acid To a mixture of tert-Butyl ((3R,5S)-1-ethyl-5-methylpiperidin-3-yl)carbamate (Example 14, step A) (265 mg, 1.09 mmol, 1.0 eq) in DCM (5 mL) was added TFA (2.0 mL, 2.19 mmol, 2.0 eq) at 0° C., then the mixture was stirred at 25° C. for 1 hour. Then the reaction mixture was concentrated under reduced pressure to afford the title compound (160 mg, 57% yield) as yellow oil. LC-MS (Method 2): m/z 143.1 $[M+H]^+$, ESI pos.

Step C: 6-(((3R,5S)-1-Ethyl-5-methylpiperidin-3-yl)amino)-3-(2-methoxy-4-(trifluoromethyl)phenyl)-4-methyl-1,2,4-triazin-5(4H)-one To a mixture of 6-chloro-3-(2-methoxy-4-(trifluoromethyl)phenyl)-4-methyl-1,2,4-triazin-5(4H)-one (Example 1, step E) (35.9 mg, 0.11 mmol, 0.2 eq) in NMP (0.5 mL) was added (3R,5S)-1-ethyl-5-methylpiperidin-3-amine: 2,2,2-trifluoroacetic acid (Example 14, step B) (80.0 mg, 0.56 mmol, 1.0 eq) in a microwave tube, then the mixture was stirred at 130° C. for 2 hours under microwave condition. The reaction mixture was quenched by addition of water (5 mL). The residue was purified by reverse phase column chromatography ($C_{18}$, 0.1% TFA in water/MeCN). The eluate was dried by lyophilization to afford the title compound (20.0 mg, 8% yield) as yellow oil. LC-MS (Method 2): m/z 426.2 $[M+H]^+$, ESI pos.

Step D: 6-[[(3R,5S)-1-Ethyl-5-methyl-3-piperidyl]amino]-3-[2-hydroxy-4-(trifluoromethyl)phenyl]-4-methyl-1,2,4-triazin-5-one;2,2,2-trifluoroacetic Acid To a mixture of 6-[[(3R,5S)-1-ethyl-5-methyl-3-piperidyl]amino]-3-[2-methoxy-4-(trifluoro methyl)phenyl]-4-methyl-1,2,4-triazin-5-one: 2,2,2-trifluoroacetic acid (Example 14, step C) (20.0 mg, 0.04 mmol, 1.0 eq) in DCM (1 mL) was added $BBr_3$ (92.9 mg, 0.37 mmol, 10.0 eq) dropwise at −60° C. The mixture was stirred at −60° C. for 10 minutes, then the mixture was stirred at 25° C. under $N_2$ for 1 hour. The reaction mixture was quenched by addition of ice water (2 mL) and adjusted to pH~7 with $NH_3 \cdot H_2O$ solution. The mixture was purified by reverse phase column chromatography ($C_{18}$, 0.1% TFA in water/MeCN condition) and then purified by preparative HPLC (column: 3_Phenomenex Luna $C_{18}$ 75*30 mm*3 μm, Condition water (TFA)-MeCN) to afford the title compound (1.83 mg, 7% yield) as a white solid. LC-MS (Method 2): m/z 412.1 $[M+H]^+$, ESI pos.

Example 15: 6-[[(3R,5R)-1-Ethyl-5-methyl-3-piperidyl]amino]-3-[2-hydroxy-4-(trifluoromethyl)phenyl]-4-methyl-1,2,4-triazin-5-one;2,2,2-trifluoroacetic Acid

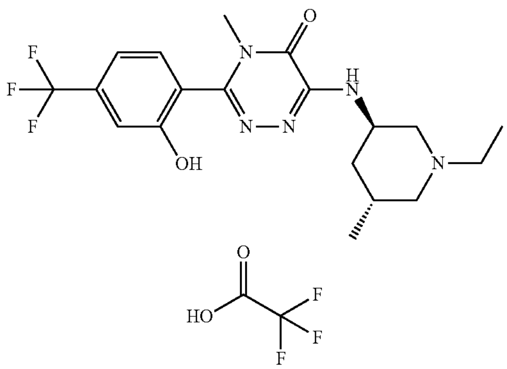

Step A: tert-Butyl (3R,5R)-3-((3-(2-methoxy-4-(trifluoromethyl)phenyl)-4-methyl-5-oxo-4,5-dihydro-1,2,4-triazin-6-yl)amino)-5-methylpiperidine-1-carboxylate To a mixture of tert-butyl (3R,5R)-3-amino-5-methylpiperidine-1-carboxylate (50.3 mg, 0.23 mmol, 1.0 eq) in NMP (0.4 mL) was added aforementioned 6-chloro-3-(2-methoxy-4-(trifluoromethyl)phenyl)-4-methyl-1,2,4-triazin-5(4H)-one (Example 1, step E) (150.0 mg, 0.47 mmol, 2.0 eq) in a microwave tube, then the mixture was stirred at 130° C. for 2 hours under microwave reactor. After cool down to room temperature, the reaction mixture was quenched by addition of water (5 mL). The residue was purified by reverse phase column chromatography ($C_{18}$, 0.1% TFA in water/MeCN condition) to afford the title compound (30.0 mg, 13% yield) as a yellow solid. LC-MS (Method 2): m/z 498.2 $[M+H]^+$, ESI pos.

Step B: 3-[2-Methoxy-4-(trifluoromethyl)phenyl]-4-methyl-6-[[(3R,5R)-5-methyl-3-piperidyl]amino]-1,2,4-triazin-5-one;2,2,2-trifluoroacetic Acid To a mixture of tert-butyl (3R,5R)-3-[[3-[2-methoxy-4-(trifluoromethyl)phenyl]-4-methyl-5-oxo-1,2,4-triazin-6-yl]amino]-5-methyl-piperidine-1-carboxylate (30.0 mg, 0.06 mmol, 1.0 eq) in DCM (1 mL) was added TFA (20.6 mg, 0.18 mmol, 3.0 eq) at 0° C., then the mixture was stirred at 25° C. for 1 hour. The reaction mixture was concentrated under reduce pressure to afford the title compound (50.0 mg, >99% yield) as yellow oil. LC-MS (Method 2): m/z 398.1 $[M+H]^+$, ESI pos.

Step C: 6-[[(3R,5R)-1-Ethyl-5-methyl-3-piperidyl]amino]-3-[2-methoxy-4-(trifluoromethyl)phenyl]-4-methyl-1,2,4-triazin-5-one;2,2,2-trifluoroacetic Acid To a mixture of 3-[2-methoxy-4-(trifluoromethyl)phenyl]-4-methyl-6-[[(3R,5R)-5-methyl-3-piperidyl]amino]-1,2,4-triazin-5-one;2,2,2-trifluoroacetic acid (50.0 mg, 0.1 mmol, 1.0 eq) in DMF (0.5 mL) was added DIEA (25.2 mg, 0.2 mmol, 2.0 eq) and iodoethane (0.01 mL, 0.11 mmol, 1.1 eq). Then the mixture was stirred at 25° C. for 2 hours. The reaction mixture was quenched by addition of water (10 mL), then extracted with EtOAc (50 mL×3), washed with brine (30 mL×2), dried over anhydrous $Na_2SO_4$, filtered and the filtrate was concentrated under reduced pressure. The residue was purified by reverse phase column chromatography ($C_{18}$, 0.1% TFA in water/MeCN condition) to afford the title compound (10.0 mg, 19% yield) as a yellow solid. LC-MS (Method 2): m/z 426.2 $[M+H]^+$, ESI pos.

Step D: 6-[[(3R,5R)-1-Ethyl-5-methyl-3-piperidyl]amino]-3-[2-hydroxy-4-(trifluoromethyl)phenyl]-4-methyl-1,2,4-triazin-5-one;2,2,2-trifluoroacetic Acid To a mixture of 6-[[(3R,5R)-1-ethyl-5-methyl-3-piperidyl]amino]-3-[2-methoxy-4-(trifluoro methyl)phenyl]-4-methyl-1,2,4-triazin-5-one; 2,2,2-trifluoroacetic acid (10.0 mg, 0.02 mmol, 1.0 eq) and in DCM (0.5 mL) was added $BBr_3$ (46.4 mg, 0.19 mmol, 10.0 eq) at −60° C. under $N_2$, and the mixture was stirred at −60° C. for 10 minutes, then the mixture warmed to 25° C. and stirred for 1 hour. The reaction mixture was quenched by 2 mL of ice water and adjusted to pH~7 with $NH_3 \cdot H_2O$ solution. The mixture was purified by reversed-phase column chromatography ($C_{18}$, 0.1% TFA water/MeCN condition) to afford the title compound (1.76 mg, 12% yield) as a white solid. LC-MS (Method 2): m/z 412.1 $[M+H]^+$, ESI pos.

Example 16: 6-[[(5S)-5-fluoro-1-methyl-3-piperidyl]amino]-3-[2-hydroxy-4-(trifluoromethyl)phenyl]-4-methyl-1,2,4-triazin-5-one;2,2,2-trifluoroacetic Acid

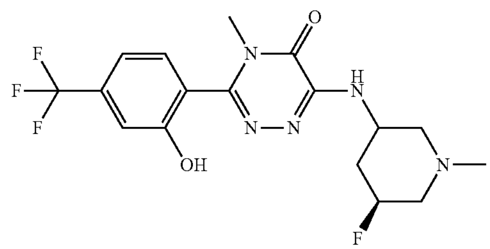

-continued

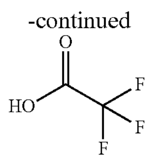

Step A: tert-Butyl (3S,5R)-3-fluoro-5-((3-(2-methoxy-4-(trifluoromethyl)phenyl)-4-methyl-5-oxo-4,5-dihydro-1,2,4-triazin-6-yl)amino)piperidine-1-carboxylate To a solution of 6-chloro-3-(2-methoxy-4-(trifluoromethyl)phenyl)-4-methyl-1,2,4-triazin-5(4H)-one (Example 1, step E) (100.0 mg, 0.31 mmol, 1.0 eq) in NMP (1.0 mL) was added DIEA (0.11 mL, 0.63 mmol, 2.0 eq) and tert-butyl (3R,5S)-3-amino-5-fluoropiperidine-1-carboxylate (CAS #1271810-13-9, 136.6 mg, 0.63 mmol, 2.0 eq). The mixture was stirred at 90° C. for 12 hours. The mixture was cooled to 20° C. and purified by reverse phase column chromatography ($C_{18}$, 0.1% TFA in water/MeCN). The eluent was lyophilized to afford the title compound (100.0 mg, 64% yield) as yellow solid. LC-MS (Method 2): m/z 502.0 $[M+H]^+$, ESI pos.

Step B: 6-[[(3R,5S)-5-Fluoro-3-piperidyl]amino]-3-[2-hydroxy-4-(trifluoromethyl)phenyl]-4-methyl-1,2,4-triazin-5-one To a solution of aforementioned tert-butyl (3S,5R)-3-fluoro-5-((3-(2-methoxy-4-(trifluoromethyl)phenyl)-4-methyl-5-oxo-4,5-dihydro-1,2,4-triazin-6-yl)amino)piperidine-1-carboxylate (Example 16, step A) (100.0 mg, 0.20 mmol, 1.0 eq) in DCM (2 mL) was added TFA (2.0 mL). The mixture was stirred at 25° C. for 1 hour. The above reaction mixture was concentrated in vacuum to afford the title compound (2.04 mg, 4% yield) as yellow oil. LC-MS (Method 2): m/z 401.9 $[M+H]^+$, ESI pos.

Step C: 6-(((3R,5S)-5-Fluoro-1-methylpiperidin-3-yl)amino)-3-(2-methoxy-4-(trifluoromethyl)phenyl)-4-methyl-1,2,4-triazin-5(4H)-one To a solution of aforementioned 6-(((3R,5S)-5-fluoropiperidin-3-yl)amino)-3-(2-methoxy-4-(trifluoromethyl)phenyl)-4-methyl-1,2,4-triazin-5(4H)-one (Example 16, step B) (80.0 mg, 0.2 mmol, 1.0 eq) in ethanol (2 mL) was added DIEA (0.07 mL, 0.4 mmol, 2.0 eq) and iodomethane (28.3 mg, 0.2 mmol, 1.0 eq). The mixture was stirred at 20° C. for 2 hours. Then, the mixture was quenched with water (3 mL). The pH was adjusted to ~7 by addition of aq. 1M HCl solution, and then the mixture was purified by reverse phase column chromatography ($C_{18}$, 0.1% TFA in water/MeCN). The eluent was lyophilized to yield the title compound (60.0 mg, 72% yield) as a yellow solid. LC-MS (Method 2): m/z 416.1 $[M+H]^+$, ESI pos.

Step D: 6-(((3R,5S)-5-Fluoro-1-methylpiperidin-3-yl)amino)-3-(2-hydroxy-4-(trifluoromethyl)phenyl)-4-methyl-1,2,4-triazin-5(4H)-one To a mixture of 6-(((3R,5S)-5-fluoro-1-methylpiperidin-3-yl)amino)-3-(2-methoxy-4-(trifluoromethyl)phenyl)-4-methyl-1,2,4-triazin-5(4H)-one (Example 16, step C) (50.0 mg, 0.12 mmol, 1.0 eq) and $K_2CO_3$ (166.1 mg, 1.2 mmol, 10.0 eq) in NMP (2 mL) was added benzenethiol (186 μL, 1.82 mmol, 15.1 eq) under $N_2$. Then, the mixture was stirred at 190° C. for 15 minutes under microwave condition. The reaction mixture was cooled to 20° C. and purified by reversed-phase column chromatography ($C_{18}$, 0.1% TFA in water/MeCN). The eluent was lyophilized to give the crude product, which was purified by Prep-HPLC (Column: Phenomenex Synergi Polar-RP 100*25 mm*4 μm; Condition water (0.1% TFA)-MeCN). The eluent was lyophilized to afford the title compound (1.7 mg, 3% yield) as white solid. Note: It seems that the racemization occurred during the de-protection at the high temperature. $^1H$ NMR (400 MHZ, MeOD-$d_4$) δ 7.55 (d, 1H), 7.31-7.28 (m, 1H), 7.24 (s, 1H), 5.40-5.30 (m, 1H), 4.20-4.07 (m, 1H), 4.00-3.79 (m, 2H), 3.78-3.45 (m, 2H), 3.64 (s, 3H), 2.95 (s, 3H), 2.48-2.40 (m, 1H), 2.28-2.20 (m, 1H). LC-MS (Method 2): m/z 402.2 $[M+H]^+$, ESI pos.

Example 17: 6-[[(3R)-6,6-Dimethyl-3-piperidyl]amino]-3-[2-hydroxy-4-(trifluoromethyl)phenyl]-4-methyl-1,2,4-triazin-5-one;2,2,2-trifluoroacetic Acid

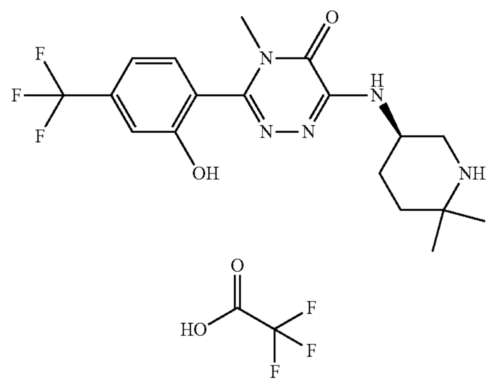

Step A: tert-Butyl (R)-(6,6-dimethylpiperidin-3-yl)carbamate

To a mixture of commercially available tert-butyl (R)-(6-oxopiperidin-3-yl)carbamate (CAS #1228566-94-6, 450.0 mg, 2.1 mmol, 1.0 eq) in 2-methyltetrahydrofuran (20 mL) was added $ZrCl_4$ (2.94 g, 12.6 mmol, 6.0 eq) at −10° C. and stirred for 0.5 hour at this temperature, then methyl magnesium bromide (14.0 mL, 42.0 mmol, 20.0 eq) was added and the mixture was stirred at 20° C. for 12 hours. The above reaction mixture was quenched with cold water (100 mL), filtered and the filtrate was extracted with ethyl acetate (20 mL×3). The combined organic phase was washed with brine (50 mL), dried over anhydrous $Na_2SO_4$, filtered and the filtrate was concentrated under reduced pressure. The crude product was purified by silica gel column (petroleum ether: ethyl acetate=5:1 to 0:1) to afford the title compound (130 mg, 27% yield) as yellow oil. $^1H$ NMR (400 MHz, MeOD-$d_4$) δ 3.42-3.32 (m, 1H), 2.93-2.81 (m, 1H), 2.63-2.50 (m, 1H), 1.83-1.73 (m, 1H), 1.62-1.52 (m, 2H), 1.48-1.41 (m, 10H), 1.14-1.09 (m, 6H).

Step B: (R)-6,6-Dimethylpiperidin-3-amine; 2,2,2-trifluoroacetic Acid

To a solution of tert-butyl (R)-(6,6-dimethylpiperidin-3-yl)carbamate (130.0 mg, 0.57 mmol, 1.0 eq) in DCM (1 mL)

was added TFA (1.0 mL) dropwise, then the mixture was stirred at 20° C. for 2 hours. The above reaction solution was concentrated under reduced pressure to give a yellow solid, which was triturated with ethyl acetate (2 mL), filtered and the cake was collected and dried under reduced pressure to afford the title compound (100 mg, 73% yield) as a white solid. $^1$H NMR (400 MHz, MeOD-$d_4$) δ 3.56-3.43 (m, 2H), 3.27-3.16 (m, 1H), 2.16-2.06 (m, 1H), 1.96-1.74 (m, 3H), 1.50-1.33 (m, 6H).

Step C: (R)-6-((6,6-Dimethylpiperidin-3-yl)amino)-3-(2-methoxy-4-(trifluoromethyl)phenyl)-4-methyl-1,2,4-triazin-5(4H)-one To a solution of (R)-6,6-dimethylpiperidin-3-amine: 2,2,2-trifluoroacetic acid (43.29 mg, 0.18 mmol, 1.0 eq) in 1,4-dioxane (1 mL) was added $Cs_2CO_3$ (145.57 mg, 0.45 mmol, 2.5 eq), 6-chloro-3-(2-methoxy-4-(trifluoromethyl) phenyl)-4-methyl-1,2,4-triazin-5(4H)-one (Example 1, step E) (60.0 mg, 0.18 mmol, 1.0 eq) and BrettPhos Pd G3 (32.4 mg, 0.04 mmol, 0.2 eq), then stirred at 80° C. for 2 hours under nitrogen atmosphere. The above reaction mixture was diluted with acetonitrile (2 mL), filtered and the filtrate was concentrated under reduced pressure. The crude product was purified by reverse phase column chromatography ($C_{18}$, 0.1% TFA in water/MeCN), then the eluent was lyophilized to afford the title compound (5.0 mg, 5% yield) as a white solid. LC-MS (Method 1): m/z 412.2 $[M+H]^+$, ESI pos.

Step D: 6-[[(3R)-6,6-dimethyl-3-piperidyl]amino]-3-[2-hydroxy-4-(trifluoromethyl)phenyl]-4-methyl-1,2,4-triazin-5-one;2,2,2-trifluoroacetic Acid To a solution of (R)-6-((6,6-dimethylpiperidin-3-yl) amino)-3-(2-methoxy-4-(trifluoromethyl)phenyl)-4-methyl-1,2,4-triazin-5(4H)-one (Example 17, step C) (10.0 mg, 0.02 mmol, 1.0 e.) in DCM (1 mL) was added $BBr_3$ (0.1 mL) drop wise at −40° C., then the reaction mixture was stirred at 20° C. for 1 hour. The above reaction mixture was quenched with water (0.5 mL) at 0° C., diluted with MeOH (1 mL), then the pH was adjusted to ~7 with ammonium hydroxide, then purified by reverse phase column chromatography ($C_{18}$, 0.1% TFA in water-ACN). The eluent was lyophilized to give a yellow solid, which was further purified by Prep-HPLC (Column 3_Phenomenex Luna $C_{18}$ 75*30 mm*3 μm; conditions: water (TFA)-$CH_3CN$), then the eluent was lyophilized to afford the title compound (1.21 mg, 18% yield) as a white solid. LC-MS (Method 1): m/z 398.0 $[M+H]^+$, ESI pos.

Example 18: 6-[(3-Hydroxyphenyl)methylamino]-3-[2-hydroxy-4-(trifluoromethyl)phenyl]-4-methyl-1,2,4-triazin-5-one;2,2,2-trifluoroacetic Acid

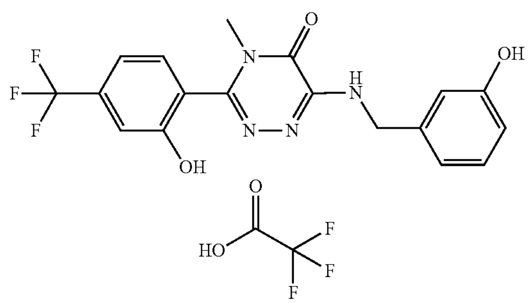

Step A: 6-((3-Hydroxybenzyl)amino)-3-(2-methoxy-4-(trifluoromethyl)phenyl)-4-methyl-1,2,4-triazin-5(4H)-one To a mixture of aforementioned 6-chloro-3-[2-methoxy-4-(trifluoromethyl)phenyl]-4-methyl-1,2,4-triazin-5-one (Example 1, step E) (30.0 mg, 0.09 mmol, 1.0 eq) and commercially available 3-(aminomethyl)phenol (CAS #73604-31-6, 57.9 mg, 0.47 mmol, 5.0 eq) in NMP (1 mL) was added DIEA (6.64 mg, 0.47 mmol, 5.0 eq), the reaction mixture was stirred at 95° C. for 2 hours under $N_2$. LC-MS showed the desired mass was detected. The mixture was concentrated under reduced pressure to give a crude product, which was purified by reversed-phase column chromatography ($C_{18}$, 0.1% TFA in water/MeCN condition) and then the eluent was lyophilized to afford the title compound (20.0 mg, 52% yield) as a yellow solid. LC-MS (Method 2): m/z 406.9 $[M+H]^+$, ESI pos.

Step B: 6-[(3-Hydroxyphenyl)methylamino]-3-[2-hydroxy-4-(trifluoromethyl)phenyl]-4-methyl-1,2,4-triazin-5-one;2,2,2-trifluoroacetic Acid A mixture of aforementioned 6-((3-hydroxybenzyl) amino)-3-(2-methoxy-4-(trifluoromethyl)phenyl)-4-methyl-1,2,4-triazin-5(4H)-one (Example 18, step A) (20.0 mg, 0.05 mmol, 1.0 eq) and boron tribromide (493.2 mg, 1.97 mmol, 40.0 eq) in DCM (1 mL) was stirred at −60° C. for 10 minutes, then stirred at 25° C. for 50 minutes. LC-MS showed desired mass was detected. The mixture was adjusted to pH~7 by addition of $NH_3·H_2O$, then filtered and the filtrate was concentrated in vacuum to give the crude product, which was purified by reverse phase column chromatography ($C_{18}$, 0.1% TFA in water/MeCN condition), then the eluent was lyophilized to afford the title compound (2.95 mg, 12% yield) as a yellow solid. LC-MS (Method 2): m/z 393.2 $[M+H]^+$, ESI pos.

Example 19: 6-[[(3R)-1-Ethyl-3-piperidyl]amino]-3-[2-hydroxy-4-(trifluoromethyl)phenyl]-4-methyl-1,2,4-triazin-5-one;2,2,2-trifluoroacetic Acid

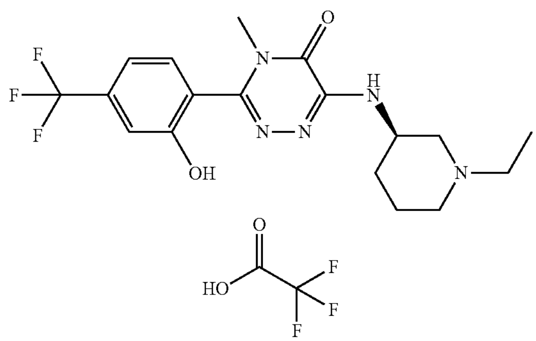

Step A: (R)-6-((1-Ethylpiperidin-3-yl)amino)-3-(2-methoxy-4-(trifluoromethyl)phenyl)-4-methyl-1,2,4-triazin-5(4H)-one To a mixture of aforementioned 6-chloro-3-(2-methoxy-4-(trifluoromethyl)phenyl)-4-methyl-1,2,4-triazin-5(4H)-one (Example 1, step E) (180.0 mg, 0.41 mmol, 1.0 eq) and (R)-1-ethylpiperidin-3-amine (156.6 mg, 1.22 mmol, 3.0 eq)

in NMP (3 mL) was added DIEA (157.8 mg, 1.22 mmol, 3.0 eq), the reaction mixture was stirred at 95° C. for 2 hours. LC-MS showed desired mass was detected. The mixture was concentrated in vacuum to give a crude product, which was purified by reversed-phase column chromatography ($C_{18}$, 0.1% TFA in water/MeCN condition). The eluent was lyophilized to afford the title compound (75.0 mg, 61% yield) as a white solid. LC-MS (Method 2): m/z 412.2 $[M+H]^+$, ESI pos.

Step B: 6-[[(3R)-1-Ethyl-3-piperidyl]amino]-3-[2-hydroxy-4-(trifluoromethyl)phenyl]-4-methyl-1,2,4-triazin-5-one;2,2,2-trifluoroacetic Acid A mixture of aforementioned (R)-6-((1-ethylpiperidin-3-yl)amino)-3-(2-methoxy-4-(trifluoromethyl)phenyl)-4-methyl-1,2,4-triazin-5(4H)-one (Example 19, step A) (75.0 mg, 0.19 mmol, 1.0 eq) and boron tribromide (243.6 mg, 0.97 mmol, 5.0 eq) in DCM (2 mL) was stirred at −60° C. for 10 minutes, then stirred at 25° C. for 50 minutes. LC-MS showed desired mass was detected. The mixture was adjusted to pH~7 by $NH_3 \cdot H_2O$, then filtered and the filtrate was concentrated in vacuum. The crude product was purified by reverse phase column chromatography ($C_{18}$, 0.1% TFA in water/MeCN condition), then the eluent was lyophilized to afford the title compound (35 mg. 32% yield) as a white solid. LC-MS (Method 2): m/z 398.0 $[M+H]^+$, ESI pos. Example 19 was also synthesized following to this method as free base:

6-[[(3R)-1-Ethyl-3-piperidyl]amino]-3-[2-hydroxy-4-(trifluoromethyl)phenyl]-4-methyl-1,2,4-triazin-5-one 3-Chloro-6-[[(3R)-1-ethyl-3-piperidyl]amino]-4-methyl-1,2,4-triazin-5-one (Example 2, step D)) (750.0 mg. 2.76 mmol, 1.0 eq), saturated aq. sodium carbonate (2.50 mL, 0.59 mmol, 0.21 eq) and 2-methoxy-4-(trifluoromethyl)-phenylboronic acid (CAS #312936-89-3, 667.7 mg, 3.04 mmol, 1.1 eq) were suspended in 1,4-dioxane (16 mL) and the reaction mixture was sparged with $N_2$, then evacuated and back-filled with $N_2$ (3×). Xphos Pd G3 (233.89 mg, 0.28 mmol, 0.1 eq) was added and the reaction mixture placed under $N_2$, then stirred at 80° C. for 24 h. The reaction mixture was filtered, dry-loaded onto silica gel and purified by chromatography on silica gel (24 g column, 0-10% (0.7 N $NH_3$ in MeOH)/DCM) to afford the intermediate product which was then dissolved in DCM (30 mL) and $BBr_3$ (1 M in DCM) (13.8 mL, 13.8 mmol, 5.0 eq) was added slowly at 0° C. The reaction mixture was stirred at room temperature for 3 h, then concentrated in vacuo. The resulting residue was taken up in MeOH (40 mL) and solid $NaHCO_3$ (5 g) was added. The mixture was stirred at room temperature for 30 min, then filtered and the filtrate concentrated in vacuo. The resulting residue was purified by chromatography on silica gel (24 g column, 0-10% (0.7 N $NH_3$ in MeOH)/DCM) and then purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) using a Waters XBridge BEH $C_{18}$ ODB prep column, 130 Å, 5 µm, 30 mm×100 mm, flow rate 40 mL min-1 eluting with a 0.3% ammonia in water-MeCN gradient over 12.5. At-column dilution pump gives 2 mL min-1 MeCN over the entire method, which is included in the following MeCN percentages. Gradient information: 0.0-0.5 min, 5% MeCN: 0.5-10.5 min, ramped from 5% MeCN to 30% MeCN: 10.5-10.6 min, ramped from 30% MeCN to 100% MeCN: 10.6-12.5 min, held at 100% MeCN. The clean fractions were evaporated in a Genevac to afford the title compound (196.0 mg. 18% yield) as a white solid. LC-MS m/z. 398.4 $[M+H]^+$, ESI pos.

Example 20: 4-Cyclopropyl-6-[[(3R)-1-ethyl-3-piperidyl]amino]-3-[2-hydroxy-4-(trifluoromethyl)phenyl]-1,2,4-triazin-5-one;2,2,2-trifluoroacetic Acid

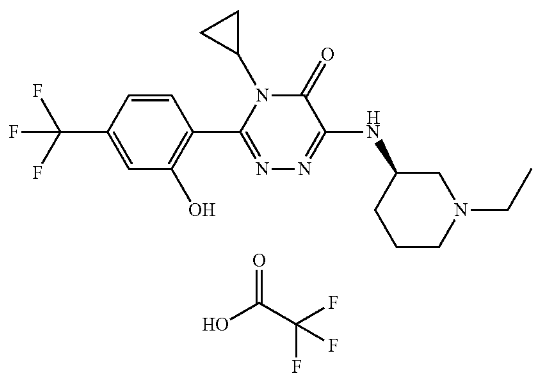

Step A: N-Cyclopropyl-2-methoxy-4-(trifluoromethyl)benzothioamide

To a solution of commercially available 1-bromo-2-methoxy-4-(trifluoromethyl)benzene (CAS #402-07-3, 5.00 g, 19.6 mmol, 1.0 eq) in THF (50 mL) was added n-BuLi (11.8 mL, 29.4 mmol, 1.5 eq) drop wise at −60° C. under nitrogen atmosphere and stirred at this temperature for 0.5 hour, then a solution of isothiocyanatocyclopropane (2.53 g, 25.5 mmol, 1.3 eq) in THF (3 mL) was added and the reaction mixture was stirred at −60° C. for 10 minutes and then left warmed to 25° C. and stirred for another 50 minutes under nitrogen atmosphere. The reaction mixture was quenched with a saturated aq. solution of $NH_4Cl$ (30 mL), extracted with EtOAc (100 mL×3), washed with brine (30 mL), dried over anhydrous $Na_2SO_4$, filtrated and the filtrate was concentrated under reduced pressure. The residue was purified by column chromatography ($SiO_2$, PE~PE:EA=30/1~10/1) to afford the title compound (1.60 g, 30% yield) as yellow oil. LC-MS (Method 1): m/z 276.1 $[M+H]^+$, ESI pos.

Step B: Methyl N-cyclopropyl-2-methoxy-4-(trifluoromethyl)benzimidothioate

To a solution of N-cyclopropyl-2-methoxy-4-(trifluoromethyl)benzothioamide (Example 20, step A) (1.60 g, 5.81 mmol, 1.0 eq) in DMF (10 mL) was added DIEA (0.82 g, 6.33 mmol, 1.1 eq) at 20° C. and stirred for 10 minutes, followed by addition of Mel (1.0 g, 7.08 mmol, 1.22 eq). The mixture was stirred at 20° C. for 3 hours. The mixture was poured into water (100 mL) and extracted with ethyl acetate (50 mL×3). The combined organic layers were washed with brine (100 mL), dried over anhydrous $Na_2SO_4$, filtered and the filtrate was concentrated under reduced pressure. The residue was purified by column chromatography ($SiO_2$, Petroleum ether/Ethyl acetate=10/1 to 3/1) to afford the title compound (1.30 g, 76% yield) as yellow oil. LC-MS (Method 1): m/z 290.0 $[M+H]^+$, ESI pos.

Step C: N"-Cyclopropyl-2-methoxy-4-(trifluoromethyl)benzimidohydrazide

To a solution of methyl N-cyclopropyl-2-methoxy-4-(trifluoromethyl)benzimidothioate (Example 20, step B) (1.30 g, 4.49 mmol, 1.0 eq) in ethanol (15 mL) was added hydrazine hydrate (2.28 g, 45.5 mmol, 10.1 eq). The mixture was stirred at 70° C. for 24 hours under nitrogen atmosphere. The mixture was concentrated under reduced pressure, then purified by reversed-phase column chromatography ($C_{18}$, 0.1% TFA in water/MeCN condition). The eluent was lyophilized to afford the title compound (900.0 mg, 50% yield) as a yellow solid. LC-MS (Method 1): m/z 274.1 $[M+H]^+$, ESI pos.

Step D: 6-Amino-4-cyclopropyl-3-(2-methoxy-4-(trifluoromethyl)phenyl)-1,2,4-triazin-5(4H)-one A mixture of N"-cyclopropyl-2-methoxy-4-(trifluoromethyl)benzimidohydrazide (Example 20, step C) (390.0 mg, 1.43 mmol, 1.0 eq), TEA (288.9 mg, 2.85 mmol, 2.0 eq) and ethyl 2-amino-2-thioxo acetate (285.1 mg, 2.14 mmol, 1.5 eq) in ethanol (8 mL) was stirred for 4 hours at 85° C. under nitrogen atmosphere. The reaction solution was cooled to room temperature and concentrated under reduced pressure, then purified by reversed-phase column chromatography ($C_{18}$, 0.1% TFA in water/MeCN). The eluent was lyophilized to afford the title compound (220 mg, 44% yield) as a yellow solid. LC-MS (Method 1): m/z 327.0 $[M+H]^+$, ESI pos.

Step E: 6-Chloro-4-cyclopropyl-3-(2-methoxy-4-(trifluoromethyl)phenyl)-1,2,4-triazin-5(4H)-one To a mixture of 6-amino-4-cyclopropyl-3-(2-methoxy-4-(trifluoromethyl)phenyl)-1,2,4-triazin-5(4H)-one (Example 20, step D) (200.0 mg, 0.61 mmol, 1.0 eq), CuCl (182.1 mg, 1.84 mmol, 3.0 eq), LiCl (51.97 mg, 1.23 mmol, 2.0 eq), benzyl(triethyl)azanium;chloride (530.56 mg, 2.33 mmol, 3.8 eq) in MeCN (5 mL) was added tert-butyl nitrite (316.1 mg, 3.06 mmol, 5.0 eq) at 25° C., then the reaction mixture was stirred at 70° C. for 1 hour under nitrogen atmosphere. The mixture was filtered and the filtrate was concentrated in vacuum, then purified by reversed-phase column chromatography ($C_{18}$, 0.1% TFA in water/MeCN), then lyophilized to afford the title compound (70.0 mg, 30% yield) as a yellow solid. LC-MS (Method 1): m/z 345.9 $[M+H]^+$, ESI pos.

Step F: (R)-4-Cyclopropyl-6-((1-ethylpiperidin-3-yl)amino)-3-(2-methoxy-4-(trifluoromethyl)phenyl)-1,2,4-triazin-5(4H)-one To a mixture of 6-chloro-4-cyclopropyl-3-(2-methoxy-4-(trifluoromethyl)phenyl)-1,2,4-triazin-5(4H)-one (Example 20, step E) (70.0 mg, 0.2 mmol, 1.0 eq) and (R)-1-ethylpiperidin-3-amine (77.9 mg, 0.61 mmol, 3.0 eq) in NMP (1 mL) was added DIEA (78.5 mg, 0.61 mmol, 3.0 eq) then stirred at 95° C. for 2 hours under nitrogen atmosphere. The mixture was concentrated in vacuum, then purified by reversed-phase column chromatography ($C_{18}$, 0.1% TFA in water/MeCN), the eluent was lyophilized to afford the title compound (40.0 mg, 45% yield) as a yellow solid. LC-MS (Method 1): m/z 437.9 $[M+H]^+$, ESI pos.

Step G: 4-Cyclopropyl-6-[[(3R)-1-ethyl-3-piperidyl]amino]-3-[2-hydroxy-4-(trifluoromethyl)phenyl]-1,2,4-triazin-5-one;2,2,2-trifluoroacetic Acid To a solution of (R)-4-cyclopropyl-6-((1-ethylpiperidin-3-yl)amino)-3-(2-methoxy-4-(tri fluoromethyl)phenyl)-1,2,4-triazin-5(4H)-one (Example 20, step F) (40.0 mg, 0.09 mmol, 1.0 eq) in DCM (4 mL) was added $BBr_3$ (229 mg, 0.91 mmol, 10.0 eq) at −40° C., then stirred at 20° C. for 1 hour. The reaction mixture was quenched with water (0.5 mL), then the pH was adjusted to 8 with ammonium hydroxide, then concentrated under reduced pressure. The residue was dissolved with MeOH (2 mL), then purified by Prep-HPLC (column: 3_Phenomenex Luna $C_{18}$ 75*30 mm*3 μm; Condition: water (TFA)-MeCN). Finally, the eluent was lyophilized to afford the title compound (12.7 mg, 25% yield) as yellow oil. LC-MS (Method 1): m/z 423.9 $[M+H]^+$, ESI pos.

Example 21: 6-[[(3R)-1-Ethyl-3-piperidyl]amino]-3-(4-fluoro-2-hydroxy-phenyl)-4-methyl-1,2,4-triazin-5-one

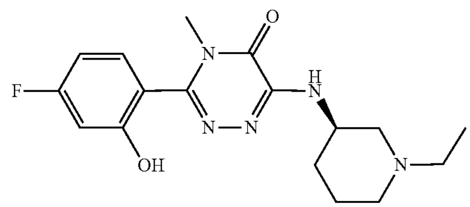 [SMILES: CCN1CCC[C@@H](Nc2nnc(-c3ccc(F)cc3O)n(C)c2=O)C1]

3-Chloro-6-[[(3R)-1-ethyl-3-piperidyl]amino]-4-methyl-1,2,4-triazin-5-one (Example 2, step D) (100 mg, 0.330 mmol, 1.0 eq) sat. aq. $Na_2CO_3$ (0.5 mL), commercially available (4-fluoro-2-hydroxy)phenylboronic acid (CAS #850568-00-2, 56.8 mg, 0.36 mmol, 1.1 eq) were suspended in 1,4-dioxane (3.5 mL) and the reaction mixture was sparged with $N_2$, then evacuated and back-filled with $N_2$ (3×) and Xphos Pd G3 (28.1 mg, 0.03 mmol, 0.1 eq) was added and the reaction mixture placed under $N_2$, then stirred at 80° C. for 18 h. The reaction mixture was concentrated in vacuo. The resulting residue was dissolved in 2 mL of DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters XBridge BEH $C_{18}$ ODB prep column, 130 Å, 5 μm, 30 mm×100 mm, flow rate 40 mL min-1 eluting with a 0.1% Ammonia in water-MeCN gradient over 17.5 mins using UV across all wavelengths with PDA as well as a QDA and ELS detector. At-column dilution pump gives 2 mL min-1 MeCN over the entire method, which is included in the following MeCN percentages. Gradient information: 0.0-0.5 min, 5% MeCN; 0.5-15.5 min, ramped from 5% MeCN to 35% MeCN: 15.5-15.6 min, ramped from 35% MeCN to 100% MeCN: 15.6-17.5 min, held at 100% MeCN. This afforded the title compound (12.02 mg, 10% yield) as a light brown solid. LC-MS m/z 348.3 $[M+H]^+$, ESI pos.

Example 22: 4-Ethyl-6-[[(3R)-1-ethyl-3-piperidyl]amino]-3-[2-hydroxy-4-(trifluoromethyl)phenyl]-1,2,4-triazin-5-one

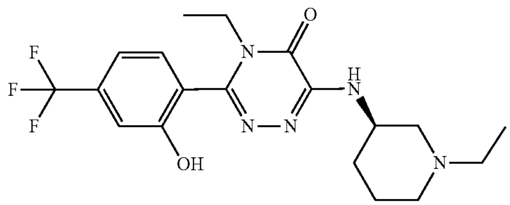 [SMILES: CCN1CCC[C@@H](Nc2nnc(-c3ccc(C(F)(F)F)cc3O)n(CC)c2=O)C1]

Step A: 6-Bromo-4-ethyl-2H-1,2,4-triazine-3,5-dione

Sodium hydride (60% in mineral oil) (7.86 g, 19.7 mmol, 1.1 eq) was placed in DMF (10 mL) under nitrogen, and a solution of commercially available 2-acetyl-6-bromo-1,2,4-triazine-3,5-dione (CAS #20028-51-7, 4.18 g, 17.9 mmol, 1.0 eq) in DMF (30 mL) was added dropwise. The reaction mixture was stirred at room temperature for 45 minutes, then iodoethane (1.57 mL, 19.7 mmol, 1.1 eq) was added dropwise and the reaction mixture stirred at room temperature for 18 h. The reaction mixture was diluted with EtOAc (200 mL) and washed with 10 wt % aq. LiCl (2×100 mL), dried using a phase separator and concentrated in vacuo. The resulting residue was purified by flash chromatography on silica gel (120 g column, 0-5% DCM/MeOH) to afford a yellow oil. The yellow oil was dissolved in EtOH (30 mL) and p-toluenesulfonic acid monohydrate (169.9 mg, 0.89 mmol, 0.05 eq) was added. The reaction mixture was stirred at reflux for 16 h, then concentrated in vacuo and the resulting residue partitioned between water (200 mL) and EtOAc (200 mL). The organic phase was isolated and the aq. extracted with EtOAc (2×200 mL). The combined organic extracts were dried using a phase separator and concentrated in vacuo to afford the title compound (2.85 g, 60% yield) as a light yellow solid. LC-MS m/z 217.8 ([37Cl]M+H)$^+$, ESI pos.

Step B: 6-Bromo-4-ethyl-2-[(4-methoxyphenyl)methyl]-1,2,4-triazine-3,5-dione

6-Bromo-4-ethyl-2H-1,2,4-triazine-3,5-dione (Example 22, step A) (2.85 g, 12.95 mmol, 1.0 eq) and dipotassium carbonate (8.95 g, 6.48 mmol, 0.5 eq) were suspended in dry DMF (30 mL) and 4-methoxy benzylchloride (2.11 mL, 15.5 mmol, 1.2 eq) was added. The reaction mixture was stirred at room temperature for 24 h. The reaction mixture was diluted with EtOAc (50 mL) and washed with 10 wt % aq. LiCl (2×30 mL), dried using a phase separator and concentrated in vacuo. The resulting residue was purified by chromatography on silica gel (24 g column, 0-50% EtOAc/isohexane) to yield the title compound (3.91 g, 80% yield) as a white solid. $^1$H NMR (500 MHz, DMSO-$d_6$) δ 7.30-7.25 (m, 2H), 6.93-6.88 (m, 2H), 5.00 (s, 2H), 3.83 (q, 2H), 3.74 (s, 3H), 1.12 (t, 3H).

Step C: 4-Ethyl-6-[[(3R)-1-ethyl-3-piperidyl]amino]-2-[(4-methoxyphenyl)methyl]-1,2,4-triazine-3,5-dione Cesium carbonate (4.85 mg, 14.9 mmol, 4.5 eq) and 6-bromo-4-ethyl-2-[(4-methoxyphenyl)methyl]-1,2,4-triazine-3,5-dione (Example 22, step B) (1.25 g, 3.31 mmol, 1.0 eq) and (3R)-1-ethylpiperidin-3-amine (6.36 mg, 4.96 mmol, 1.5 eq) were dissolved in DMSO (16 mL) and the mixture degassed ($N_2$) for 5 min. The reaction vessel was evacuated and back-filled with $N_2$ (3×), then Pd-176 (CAS #879689-47-1, 133 mg, 0.17 mmol, 0.05 eq) was added and the reaction mixture placed under $N_2$, then stirred at 95° C. for 24 h. The reaction mixture was partitioned between EtOAc (50 mL) and water (50 mL). The organic phase was isolated, washed with brine (2×30 mL), dried using a phase separator and concentrated in vacuo. The resulting residue was purified by chromatography on silica gel (24 g column, 0-10% (0.7 N ammonia in MeOH) in DCM) to afford the title compound (996 mg, 71% yield) as a light brown oil. LC-MS m/z 388.4 (M+H)$^+$, ESI pos.

Step D: 4-Ethyl-6-[[(3R)-1-ethyl-3-piperidyl]amino]-2H-1,2,4-triazine-3,5-dione; Trifluoromethanesulfonic Acid 4-Ethyl-6-[[(3R)-1-ethyl-3-piperidyl]amino]-2-[(4-methoxyphenyl)methyl]-1,2,4-triazine-3,5-dione (996.0 mg, 2.34 mmol, 1.0 eq) was dissolved in DCM (9 mL) and trifluoromethanesulfonic acid (0.31 mL, 3.51 mmol, 1.5 eq) was added to the reaction. The resulting solution was stirred at room temperature for 24 h. The reaction mixture was concentrated in vacuo and the resulting residue was purified by chromatography on silica gel (24 g column, 0-10% (0.7 N ammonia in MeOH/DCM) to afford the title compound (950 mg, 88% yield) as a yellow oil. LC-MS m/z 268.4 [M+H]$^+$, ESI pos.

Step E: 3-Chloro-4-ethyl-6-[[(3R)-1-ethyl-3-piperidyl]amino]-1,2,4-triazin-5-one 4-Ethyl-6-[[(3R)-1-ethyl-3-piperidyl]amino]-2H-1,2,4-triazine-3,5 dione;trifluoromethanesulfonic acid (950 mg, 2.28 mmol, 1.0 eq) was dissolved in phosphorus oxychloride (6.29 mL, 67.5 mmol, 29.6 eq). The reaction was stirred at 90° C. for 16 h, then concentrated in vacuo. The resulting residue was cooled in an ice bath and slowly quenched with 0.7 N $NH_3$ in MeOH, then dry loaded onto silica, before being purified by chromatography on silica gel (40 g column, 0-10% (0.7 N ammonia in MeOH)/DCM) to afford the title compound (768 mg, 89% yield) as a yellow gum. LC-MS m/z 285.9 ([37Cl]M+H)$^+$, ESI pos.

Step F: This Step was Synthesised by Methods Analogous to Those Outlined Above (See Example 21)

| Example | Structure and Name | Starting materials | Analytics |
|---|---|---|---|
| 22 | 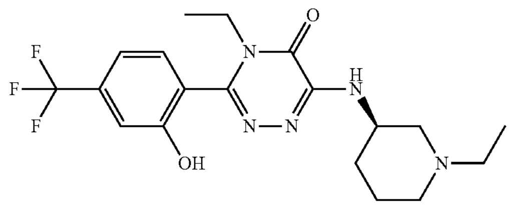 [SMILES: CCN1CCC[C@@H](Nc2nnc(-c3ccc(C(F)(F)F)cc3O)n(CC)c2=O)C1] 4-Ethyl-6-[[(3R)-1-ethyl-3-piperidyl]amino]-3-[2-hydroxy-4-(trifluoromethyl)phenyl]-1,2,4-triazin-5-one | 3-Chloro-4-ethyl-6-[[(3R)-1-ethyl-3-piperidyl]amino]-1,2,4-triazin-5-one (Example 22, Step E) and [2-hydroxy-4-(trifluoromethyl)phenyl]-boronic acid CAS #1072951-50-8 | LC-MS m/z 410.4 $[M + H]^+$, ESI pos |

Example 23: 3-[4-(Difluoromethoxy)-2-hydroxy-phenyl]-6-[[(3R)-1-ethyl-3-piperidyl]amino]-4-methyl-1,2,4-triazin-5-one; Formic Acid

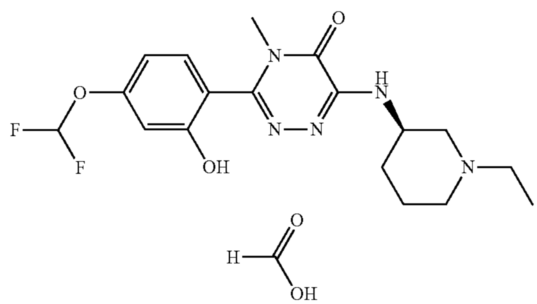

Step A: 3-[4-(Difluoromethoxy)-2-methoxy-phenyl]-6-[[(3R)-1-ethyl-3-piperidyl]amino]-4-methyl-1,2,4-triazin-5-one 3-Chloro-6-[[(3R)-1-ethyl-3-piperidyl]amino]-4-methyl-1,2,4-triazin-5-one (Example 2, step D) (260.0 mg, 0.91 mmol, 1.0 eq), commercially available 2-[4-(difluoromethoxy)-2-methoxy-phenyl]-4,4,5,5-tetramethyl-1,3,2-dioxaborolane (CAS #2121514-61-0, 430.0 mg, 1.07 mmol, 1.18 eq) in sat. aq. $Na_2CO_3$ (0.5 mL, 0.91 mmol, 1.0 eq) and 1,4-dioxane (5 mL) was sparged (10 min bubbling with $N_2$ and sonicating). XPhos Pd G3 (52.0 mg, 0.06 mmol, 0.07 eq) was added and the reaction mixture heated at 90° C. for 18 h. The crude mixture was passed through a plug of Celite® and rinsed with EtOAc (50 mL) and reaction mixture was concentrated in vacuo. The reaction was purified by column chromatography (silica, 24 g, 10-20% MeOH (with 0.7 M $NH_3$) and then by reverse phase column chromatography ($C_{18}$, 26 g, 10-60% Acetonitrile:water (10 mM ammonium bicarbonate), to afford the title compound (99.0 mg, 26% yield), as a light brown solid. LC-MS m/z 410.4 $[M+H]^+$, ESI pos.

Step B: 3-[4-(Difluoromethoxy)-2-hydroxy-phenyl]-6-[[(3R)-1-ethyl-3-piperidyl]amino]-4-methyl-1,2,4-triazin-5-one; Formic Acid A suspension of 3-[4-(difluoromethoxy)-2-methoxy-phenyl]-6-[[(3R)-1-ethyl-3-piperidyl]amino]-4-methyl-1,2,4-triazin-5-one (50.0 mg, 0.12 mmol, 1.0 eq) and potassium carbonate (50.0 mg, 0.36 mmol, 2.96 eq) in NMP (1 mL) in a MW vial was sonicated for 2 min then benzenethiol (0.02 mL, 0.2 mmol, 1.61 eq) was added and the resulting mixture was irradiated to 150° C. for 30 min. The reaction was cooled to rt and diluted with NMP (2.4 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH $C_{18}$ ODB prep column, 130 Å, 5 μm, 30 mm×100 mm, flow rate 40 mL min-1 eluting with a 0.1% Formic acid in water-MeCN gradient over 12.5 mins using UV across all wavelengths with PDA as well as a QDA and ELS detector. At-column dilution pump gives 2 mL min-1 MeOH over the entire method, which is included in the following MeCN percentages. Gradient information: 0.0-0.5 min, 5% MeCN: 0.5-10.5 min, ramped from 5% MeCN to 25% MeCN: 10.5-10.6 min, ramped from 25% MeCN to 100% MeCN: 10.6-12.5 min, held at 100% MeCN. The clean fractions were evaporated in a Genevac to afford the title compound (24.0 mg, 43% yield) as an off-white solid. LC-MS m/z 396.3 $[M+H]^+$, ESI pos.

Example 24: 3-[4-(1,1-Difluoroethyl)-2-hydroxy-phenyl]-6-[[(3R)-1-ethyl-3-piperidyl]amino]-4-methyl-1,2,4-triazin-5-one

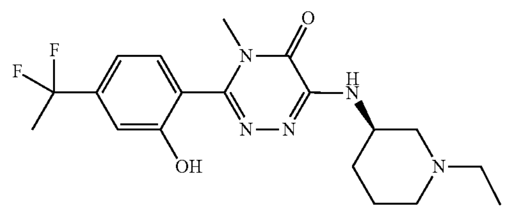 [SMILES: CCN1CCC[C@@H](Nc2nnc(-c3ccc(C(C)(F)F)cc3O)n(C)c2=O)C1]

Step A: 1-Bromo-4-(1,1-difluoroethyl)-2-methoxy-benzene

Diethylaminosulfur trifluoride (6.0 mL, 45.4 mmol, 10.4 eq) was added dropwise to a solution of 1-(4-bromo-3-methoxy-phenyl)ethenone (CAS #50870-44-5, 1.0 g, 4.37 mmol, 1.0 eq) in DCM (8 mL) at 0° C. in a Teflon flask and the reaction mixture was allowed to warm and stir for 16 h. The reaction mixture was cooled to 0° C. and diethylaminosulfur trifluoride (3.0 mL, 22.7 mmol, 5.2 eq) was added and the reaction left to stir for 4 days. The reaction mixture was cooled to 0° C. and diethylaminosulfur trifluoride (3.0 mL, 22.7 mmol, 5.2 eq) was added and the reaction left to stir for 18 h. The reaction mixture was cooled to 0° C. and carefully added by dropwise addition to a vigorously stirring plastic beaker containing ice cold 2M NaOH (250 mL), and the reaction mixture transferred to a separating funnel, rinsing with DCM (75 mL). The separated aq. layer was further extracted with DCM (2×50 mL), the combined organic layers combined, dried ($Na_2SO_4$) and concentrated under reduced pressure. The crude reaction mixture was purified by column chromatography (silica, 40 g, 0-30% EtOAc:isoHexane) and then by reverse phase column chromatography ($C_{18}$, 40 g, 10-80% Acetonitrile (0.1% formic acid):water (0.1% formic acid), to afford the title compound (363.0 mg, 33% yield), as a light yellow oil. $^1H$ NMR (500 MHz, $CDCl_3$) δ 7.58 (d, 1H), 7.03 (s, 1H), 6.96 (d, 1H), 3.93 (s, 3H), 1.91 (t, 3H).

Step B: 3-[4-(1,1-Difluoroethyl)-2-methoxy-phenyl]-6-[[(3R)-1-ethyl-3-piperidyl]amino]-4-methyl-1,2,4-triazin-5-one 1-Bromo-4-(1,1-difluoroethyl)-2-methoxy-benzene (Example 24, step A) (210.0 mg, 0.84 mmol, 1.0 eq), bis (pinacolato)diboron (263.0 mg, 1.04 mmol, 1.24 eq) and potassium acetate (338.0 mg, 3.44 mmol, 4.12 eq) in isopropyl acetate (3 mL) was sparged (bubbling nitrogen for 10 min whilst sonicating). XPhos Pd G3 (35.0 mg, 0.04 mmol, 0.05 eq) and XPhos (9.0 mg, 0.02 mmol, 0.02 eq) were added and the reaction mixture was stirred at 90° C. for 3 h. The reaction mixture was cooled to rt and aforementioned 3-chloro-6-[[(3R)-1-ethyl-3-piperidyl]amino]-4-methyl-1,2,4-triazin-5-one (Example 2, step D) (227.0 mg, 0.84 mmol, 1.0 eq) dissolved in isopropylacetate (2 mL) was added to the reaction followed by potassium carbonate (288.0 mg, 2.08 mmol, 2.49 eq) and water (1 mL). The reaction mixture was degassed with bubbling nitrogen for 10 min whilst stirring then XPhos Pd G3 (21.0 mg, 0.02 mmol, 0.03 eq) and XPhos (4.0 mg, 0.01 mmol, 0.01 eq) were added and the reaction mixture stirred at 90° C. for 16 h. The crude reaction mixture was filtered through a plug of Celite®, rinsing with EtOAc (~50 mL). The filtrate was concentrated under reduced pressure then taken up into DCM (5 mL) which was then passed through a pipette packed with $Na_2SO_4$. The resulting clear yellow solution was concentrated to afford the title compound (588.0 mg, 52% yield) as a light yellow oil. LC-MS m/z 408.4 $[M+H]^+$, ESI pos.

Step C: 3-[4-(1,1-Difluoroethyl)-2-hydroxy-phenyl]-6-[[(3R)-1-ethyl-3-piperidyl]amino]-4-methyl-1,2,4-triazin-5-one Benzenethiol (3.0 μL, 0.03 mmol, 1.0 eq) and potassium carbonate (8.0 mg, 0.06 mmol, 1.97 eq) were added to microwave vial containing 3-[4-(1,1-difluoroethyl)-2-methoxy-phenyl]-6-[[(3R)-1-ethyl-3-piperidyl]amino]-4-methyl-1,2,4-triazin-5-one (12.0 mg, 0.03 mmol, 1.0 eq) (Example 5, Step A) in NMP (1 mL). The reaction was irradiated to 150° C. for 15 min and then concentrated in vacuo. The resulting residue was dissolved in DMSO (1.3 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters XBridge BEH C18 ODB prep column, 130 Å, 5 μm, 30 mm×100 mm, flow rate 40 mL min-1 eluting with a 0.3% Ammonia in water-MeCN gradient over 12.5 mins using UV across all wavelengths with PDA as well as a QDA and ELS detector. At-column dilution pump gives 2 mL min-1 MeOH over the entire method, which is included in the following MeCN percentages. Gradient information: 0.0-0.5 min, 5% MeCN; 0.5-10.5 min, ramped from 5% MeCN to 35% MeCN: 10.5-10.6 min, ramped from 35% MeCN to 100% MeCN: 10.6-12.5 min, held at 100% MeCN. The clean fractions were evaporated in a Genevac to afford the title compound (4.0 mg, 33% yield) as a white solid. LC-MS m/z 394.0 $[M+H]^+$, ESI pos.

Example 25: 3-(4-Acetyl-2-hydroxy-phenyl)-6-[[(3R)-1-ethyl-3-piperidyl]amino]-4-methyl-1,2,4-triazin-5-one

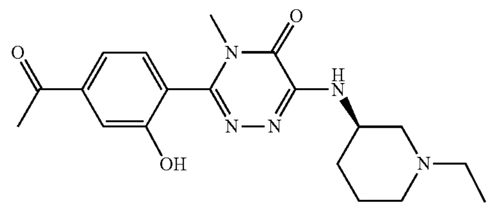 [SMILES: CCN1CCC[C@@H](Nc2nnc(-c3ccc(C(C)=O)cc3O)n(C)c2=O)C1]

A solution of 3-[4-(1,1-difluoroethyl)-2-methoxy-phenyl]-6-[[(3R)-1-ethyl-3-piperidyl]amino]-4-methyl-1,2,4-triazin-5-one (588.0 mg, 0.58 mmol, 1.0 eq) (Example 24, step B) in DCM (5 mL) was treated with boron tribromide (1 M in DCM) (3.5 mL, 3.50 mmol, 6.06 eq) dropwise at 0° C. After 30 min the mixture was allowed to warm and stir at room temperature for 1 hour. The reaction was re-cooled down the reaction mixture was quenched with 0.7M $NH_3$ in MeOH (~15 mL) and left to stir for 30 min. The reaction mixture was concentrated and then dissolved in DMSO/water (1:1, 3.5 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH $C_{18}$ ODB prep column, 130 Å, 5 μm, 30 mm×100 mm, flow rate 40 mL min-1 eluting with a 0.1% Formic acid in water-MeCN gradient over 12.5 mins using UV across all wavelengths with PDA as well as a QDA and ELS detector. At-column dilution pump gives 2 mL min-1 MeOH over the entire method, which is included in the following MeCN percentages. Gradient information: 0.0-0.5 min, 5% MeCN: 0.5-10.5 min, ramped from 5% MeCN to 22.5% MeCN: 10.5-10.6 min, ramped from 22.5% MeCN to 100% MeCN: 10.6-12.5 min, held at 100% MeCN. The clean fractions were evaporated in a Genevac to afford the title compound (15.8 mg, 7% yield) as a light yellow solid. LC-MS m/z 371.9 $[M+H]^+$, ESI pos.

Example 26: 3-[2-hydroxy-4-(trifluoromethyl)phenyl]-4-methyl-6-[[(3R)-1-methyl-3-piperidyl] amino]-1,2,4-triazin-5-one

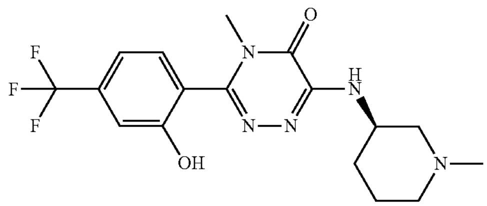 [SMILES: CN1CCC[C@@H](Nc2nnc(-c3ccc(C(F)(F)F)cc3O)n(C)c2=O)C1]

Step A: 6-[[(3R)-1-Benzyl-3-piperidyl]amino]-2-[(4-methoxyphenyl)methyl]-4-methyl-1,2,4-triazine-3,5-dione 6-Bromo-2-[(4-methoxyphenyl)methyl]-4-methyl-1,2,4-triazine-3,5-dione (Example 2, step A) (1.50 g, 4.60 mmol, 1.0 eq) and caesium carbonate (2.997 g, 9.2 mmol, 2.0 eq) and (R)-3-amino-1-benzylpiperidine (1.00 g, 5.26 mmol, 1.14 eq) were dissolved in DMSO (20 mL) and the mixture degassed ($N_2$) for 5 min. The reaction vessel was evacuated and back-filled with $N_2$ (3×), then (rac)-BINAP Pd G3 (228.2 mg, 0.23 mmol, 0.05 eq) was added and the reaction mixture placed under $N_2$, then stirred at 95° C. for 24 h. The reaction mixture was partitioned between EtOAc (250 mL) and water (250 mL). The organic phase was isolated, washed with brine (3×200 mL), dried using a phase separator and concentrated in vacuo. The resulting residue was purified by chromatography on silica gel (40 g column, 0-7% (0.7 N ammonia in MeOH) in DCM) to afford the title compound (1.98 g, 87% yield) as a yellow oil. LC-MS m/z 436.4 $[M+H]^+$, ESI pos.

Step B: 6-[[(3R)-1-benzyl-3-piperidyl]amino]-4-methyl-2H-1,2,4-triazine-3,5-dione 6-[[(3R)-1-benzyl-3-piperidyl]amino]-2-[(4-methoxyphenyl)methyl]-4-methyl-1,2,4-triazine-3,5-dione (Example 26, step A) (1.98 g. 4.0 mmol, 1.0 eq) was dissolved in DCM (18 mL). trifluoromethanesulfonic acid (0.71 mL, 8.0 mmol, 2.0 eq) was added to the reaction. The resulting solution was stirred at room temperature for 18 h, then further trifluoromethanesulfonic acid (0.71 mL, 8.0 mmol, 2.0 eq) was added and the reaction mixture stirred for a further 1 h. The reaction mixture was concentrated in vacuo and the purified by chromatography on silica gel (40 g column, 0-10% (0.7 N ammonia in MeOH/DCM) to afford the title compound (1.56 g, 3.35 mmol, 67% yield) as a light brown solid. LC-MS m/z 316.3 $[M+H]^+$, ESI pos.

Step C: 6-[[(3R)-1-Benzyl-3-piperidyl]amino]-3-chloro-4-methyl-1,2,4-triazin-5-one 6-[[(3R)-1-Benzyl-3-piperidyl]amino]-4-methyl-2H-1,2,4-triazine-3,5-dione (Example 26, step B) (0.25 g, 0.79 mmol, 1.0 eq) was dissolved in phosphorus oxychloride (4.86 mL, 52.1 mmol, 65.7 eq). The reaction was stirred at 100° C. for 24 h then 120° C. for a further 24 h. The reaction mixture was concentrated in vacuo, then diluted with EtOAc (100 mL). The mixture stirred vigorously and sat. aq. $NaHCO_3$ was added slowly to bring the pH>8. The organic phase was separated and the water phase extracted with EtOAc (2×50 mL). The combined organic extracts were dried using a phase separator and concentrated in vacuo to afford the title compound (208 mg, 72% yield) as a light brown oil. LC-MS m/z 334.3 $[M+H]^+$, ESI pos.

Step D: 6-[[(3R)-1-Benzyl-3-piperidyl]amino]-3-[2-methoxy-4-(trifluoromethyl)phenyl]-4-methyl-1,2,4-triazin-5-one 6-[[(3R)-1-Benzyl-3-piperidyl]amino]-3-chloro-4-methyl-1,2,4-triazin-5-one (Example 26, step C) (209.0 mg, 0.58 mmol, 1.0 eq), 2-methoxy-4-(trifluoromethyl)-phenylboronic acid (CAS #312936-89-3, 139.36 mg, 0.63 mmol, 1.1 eq) and sat. aq. $Na_2CO_3$ (0.5 mL) were suspended in 1,4-dioxane (4 mL) and the reaction mixture was sparged with N2, then evacuated and back-filled with $N_2$ (3×). Xphos Pd G3 (48.8 mg, 0.06 mmol, 0.1 eq) was added and the reaction mixture placed under $N_2$, then stirred at 80° C. for 24 h. The reaction mixture was partitioned between EtOAc (50 mL) and brine (50 mL). The organic phase was isolated, dried using a phase separator and concentrated in vacuo to afford the title compound (310.0 mg, 0.65 mmol, 81% yield) as a brown solid. LC-MS m/z 474.3 $[M+H]^+$, ESI pos.

Step E: 3-[2-Hydroxy-4-(trifluoromethyl)phenyl]-4-methyl-6-[[(3R)-1-methyl-3-piperidyl]amino]-1,2,4-triazin-5-one 6-[[(3R)-1-Benzyl-3-piperidyl]amino]-3-[2-methoxy-4-(trifluoromethoxy)phenyl]-4-methyl-1,2,4-triazin-5-one (Example 26, step D) (186.1 mg, 0.38 mmol, 1.0 eq) was dissolved in MeOH (8 mL) and 20 wt % palladium hydroxide on carbon (50% in $H_2O$) (80.1 mg, 0.060 mmol, 0.150 eq) was added followed by formaldehyde (37 wt % in $H_2O$) (0.28 mL, 3.8 mmol, 10 eq). The reaction mixture was stirred under 3 bar of $H_2$ for 72 h. Then additional 20 wt % Palladium hydroxide on carbon (50% in water) (91.9 mg, 0.07 mmol, 0.1 eq) was added and the reaction mixture stirred under 5 bar of $H_2$ for 24 h. The reaction mixture was filtered through a pad of Celite®, and the filtrate concentrated in vacuo. The resulting residue was taken up in DCM (10 mL) and boron tribromide (1 M in DCM) (3.27 mL, 3.27 mmol, 5.0 eq) was added slowly. The reaction mixture was stirred at room temperature for 1 h, then concentrated in vacuo. The resulting residue was dissolved in MeOH (20 mL) and $Na_2CO_3$ (5 g) was added. The reaction mixture was stirred at room temperature for 45 min, then filtered and the filtrate concentrated in vacuo. The resulting residue was dissolved in 7.5 mL of DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters XBridge BEH $C_{18}$ ODB prep column, 130 Å, 5 μm, 30 mm×100 mm, flow rate 40 mL min-1 eluting with a 0.3% Ammonia in water-MeCN gradient over 12.5 mins using UV across all wavelengths with PDA as well as a QDA and ELS detector. At-column dilution pump gives 2 mL min-1 MeOH over the entire method, which is included in the following MeCN percentages. Gradient information: 0.0-0.5 min, 5% MeCN: 0.5-10.5 min, ramped from 5% MeCN to 30% MeCN: 10.5-10.6 min, ramped from 30% MeCN to 100% MeCN: 10.6-12.5 min, held at 100% MeCN. The clean fractions were evaporated in a Genevac to afford the title compound (23.9 mg, 9% yield) as a white solid. LC-MS m/z 384.3 $[M+H]^+$, ESI pos.

The following examples 'Ex.' were synthesised by methods analogous to those outlined above:

| Ex. | Structure | Name | Starting materials | Analytics |
|---|---|---|---|---|
| 27 | 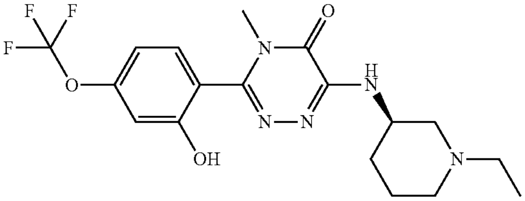 [SMILES: CCN1CCC[C@@H](Nc2nnc(-c3ccc(OC(F)(F)F)cc3O)n(C)c2=O)C1] | 6-[[(3R)-1-Ethyl-3-piperidyl]amino]-3-[2-hydroxy-4-(trifluoromethoxy)-phenyl]-4-methyl-1,2,4-triazin-5-one | 3-Chloro-6-[[(3R)-1-ethyl-3-piperidyl]-amino]-4-methyl-1,2,4-triazin-5-one (Example 2, step D) and 2-methoxy-4-(trifluoromethoxy)-phenylboronic acid CAS # 355836-10-1 | LC-MS m/z 414.4 $[M + H]^+$, ESI pos |
| 28 | 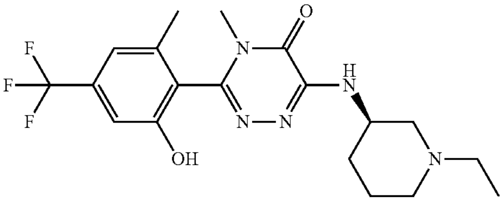 [SMILES: CCN1CCC[C@@H](Nc2nnc(-c3c(C)cc(C(F)(F)F)cc3O)n(C)c2=O)C1] | 6-[[(3R)-1-Ethyl-3-piperidyl]amino]-3-[2-hydroxy-6-methyl-4-(trifluoromethyl)phenyl]-4-methyl-1,2,4-triazin-5-one | 3-Chloro-6-[[(3R)-1-ethyl-3-piperidyl]amino]-4-methyl-1,2,4-triazin-5-one (Example 2, step D) and 2-[2-methoxy-6-methyl-4-(trifluoromethyl)-phenyl]-4,4,5,5-tetramethyl-1,3,2-dioxaborolane CAS # 2557358-25-3 | LC-MS m/z 412.6 $[M + H]^+$, ESI, pos |

Example 29: (M or P)-6-[[(3R)-1-ethyl-3-piperidyl]amino]-3-[2-hydroxy-6-methyl-4-(trifluoromethyl)phenyl]-4-methyl-1,2,4-triazin-5-one and Example 30: (P or M)-6-[[(3R)-1-ethyl-3-piperidyl]amino]-3-[2-hydroxy-6-methyl-4-(trifluoromethyl)phenyl]-4-methyl-1,2,4-triazin-5-one 3-Chloro-6-[[(3R)-1-ethyl-3-piperidyl]amino]-4-methyl-1,2,4-triazin-5-one (Example 2, step D) (350 mg, 1.29 mmol, 1.0 eq), saturated aq. sodium carbonate (1.5 mL, 5.50 mmol, 4.27 eq) and 3-methyl-2-(4,4,5,5-tetramethyl-1,3,2-dioxaborolan-2-yl)-5-(trifluoromethyl)phenol (389.1 mg, 1.29 mmol, 1.0 eq) were suspended in 1,4-Dioxane (10 mL) and the reaction mixture was sparged with $N_2$, then evacuated and back-filled with $N_2$ (3×). Xphos Pd G3 (54.57 mg, 0.06 mmol, 0.05 eq) was added and the reaction mixture placed under N2, then stirred at 80° C. for 18 h. The reaction mixture was diluted with MeOH, then dry-loaded onto silica gel, before being purified by column chromatography on silica gel (12 g column, 0-10% (0.7 N $NH_3$ in MeOH)/DCM) and by chiral SFC on a Waters prep 15 with UV detection by DAD at 210-400 nm, 40° C., 120 bar. The column was an IH 10×250 mm, 5 μM, flow rate 15 mL/min at 10% MeOH (0.03% ammonia), 90% $CO_2$. This afforded two atropisomers:

Atrop 1: Example 29 (36.5 mg, 6% yield) as a yellow solid. LC-MS m/z 412.4 $[M+H]^+$, ESI pos. $^1H$ NMR (500 MHZ, DMSO-$d_6$) δ 7.07 (s, 1H), 7.17 (s, 1H), 6.83 (d, 1H), 4.07-3.97 (m, 1H), 3.11 (s, 3H), 2.79-2.70 (m, 1H), 2.57-2.50 (m, 1H), 2.41-2.32 (m, 2H), 2.26-2.11 (m, 5H), 1.76-1.62 (m, 2H), 1.61-1.44 (m, 2H), 1.00 (t, 3H). Note: Phenol OH not observed.

Atrop 2: Example 30 (49.5 mg, 9% yield) as a yellow solid. LC-MS m/z 412.4 $[M+H]^+$, ESI pos. $^1H$ NMR (500 MHZ, DMSO-$d_6$) δ 10.65 (bs, 1H), 7.18 (s, 1H), 7.13-6.78 (m, 2H), 4.12-3.99 (m, 1H), 3.11 (s, 3H), 2.96-2.79 (m, 1H), 2.72-2.54 (m, 1H), 2.45-1.96 (m, 6H), 1.84-1.41 (m, 4H), 1.12-0.95 (m, 3H). Note: 1×N—CH signal obscured by water peak and thus not observed. Note: Diastereomeric atropisomers around the Ar—Ar double bond (stereochemistry assigned arbitrarily).

Example 31: 6-[[(3R)-1-Ethyl-3-piperidyl]amino]-3-[2-hydroxy-4-(pentafluoro-$\lambda_6$-sulfanyl)phenyl]-4-methyl-1,2,4-triazin-5-one

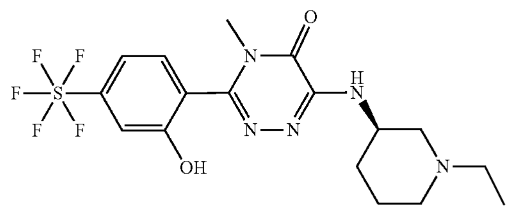 [SMILES: CCN1CCC[C@@H](Nc2nnc(-c3ccc(S(F)(F)(F)(F)F)cc3O)n(C)c2=O)C1]

Step A: 2-Iodo-5-(pentafluoro-$\lambda_6$-sulfanyl)phenol

A solution of p-toluenesulfonic acid (0.09 g, 0.52 mmol, 0.13 eq) and 3-(pentafluorothio)phenol (900.0 mg, 4.09 mmol, 1.0 eq) in MeOH (18 mL) was stirred for 15 min at R.T., then the flask was covered in tinfoil and a solution of N-iodosuccinimide (3.0 g, 13.3 mmol, 3.26 eq) in MeOH (18 mL) was added dropwise over 10 min. The reaction mixture was left to stir at room temperature for 18 h. The solvent was removed under reduced pressure, redissolved in EtOAc (20 mL) and washed with saturated sodium thiosulfate solution (50 mL). The organic layer was collected and concentrated to dryness. The residue was purified by chromatography (SiO2, 24 g cartridge, 0-30% DCM:isohexane) to afford the title compound (1.45 g, 99% yield) as a colourless solid. LC-MS: m/z 345.0 $[M-H]^-$, ESI neg.

Step B: Pentafluoro-(4-iodo-3-methoxy-phenyl)-$\lambda_6$-sulfane

Iodomethane (0.3 mL, 4.82 mmol, 1.15 eq) was added to a stirred mixture of 2-iodo-5-(pentafluoro-$\lambda_6$-sulfanyl)phenol (1.49 g, 4.19 mmol, 1.0 eq), potassium carbonate (1.50 g, 10.9 mmol, 2.59 eq). The mixture was then heated to 56° C. for 3 hours, then at room temperature for 3 days. The reaction mixture was filtered, then concentrated to dryness.

The residue obtained was partitioned between water (20 mL) and EtOAc (40 mL). The organic layer was collected, and the aq. layer was extracted with EtOAc (2×15 mL). The combined organic layers were dried ($MgSO_4$), filtered and concentrated to dryness to give an orange oil. The crude product was purified by column chromatography ($SiO_2$, 40 g cartridge, isocratic isohexane) to afford the title compound (1.36 g, 87% yield) as a colourless oil. $^1$H NMR (400 MHZ, $CDCl_3$) δ 7.87 (dt, 1H), 7.16-7.06 (m, 2H), 3.94 (s, 3H).

Step C: [2-Methoxy-4-(pentafluoro-$\lambda_6$-sulfanyl) phenyl]boronic Acid

Isopropylmagnesium chloride (2 M in THF, 2.4 mL, 4.8 mmol, 1.44 eq) was added to a stirred solution of pentafluoro-(4-iodo-3-methoxy-phenyl)-$\lambda_6$-sulfane (1.2 g, 3.33 mmol, 1.0 eq) in THF (36 mL) cooled to 0° C. The mixture was left to stir at 0° C. for 30 minutes. Tri-methyl borate (0.84 mL, 7.53 mmol, 2.26 eq) was then added and the mixture was left to stir at room temperature for 3 hours. The mixture was concentrated, then redissolved in DCM (20 mL) and washed with 10% w/v aq. $KH_2PO_3$ (3×10 mL) followed by brine (20 mL). The organic layer was dried ($MgSO_4$), filtered and concentrated to dryness. The yellow residue obtained was redissolved in DCM (36 mL), and acetic acid (0.6 mL) was added. The mixture was stirred at room temperature for 30 minutes, then water (0.36 mL) followed by THF (1.2 mL) was added. The mixture was left to stir at room temperature for 18 h. The reaction mixture was washed with 10% w/v aq. $KH_2PO_4$ (25 mL) and the organic layer was dried (MgSO4), filtered and concentrated. The resulting solid was triturated with isohexane (30 mL) to afford the title compound (576.0 mg, 62% yield) as a white powder. LC-MS: m/z 277.0 $[M-H]^-$, ESI neg.

Step D: 6-[[(3R)-1-Ethyl-3-piperidyl]amino]-3-[2-hydroxy-4-(pentafluoro-$\lambda_6$-sulfanyl)phenyl]-4-methyl-1,2,4-triazin-5-one This step was synthesised by methods analogous to those outlined above (see example 27):

| Ex. | Structure | Name | Starting materials | Analytics |
|---|---|---|---|---|
| 31 | 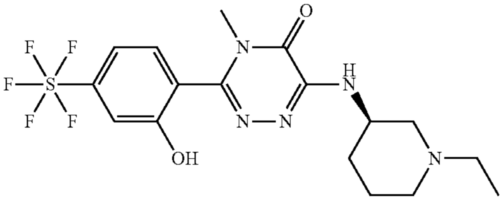 [SMILES: CCN1CCC[C@@H](Nc2nnc(-c3ccc(S(F)(F)(F)(F)F)cc3O)n(C)c2=O)C1] | 6-[[(3R)-1-Ethyl-3-piperidyl]amino]-3-[2-hydroxy-4-(pentafluoro-26-sulfanyl)phenyl]-4-methyl-1,2,4-triazin-5-one | 3-Chloro-6-[[(3R)-1-ethyl-3-piperid-yl]amino]-4-meth-yl-1,2,4-triazin-5-one (Example 2, step D) and [2-methoxy-4-(penta-fluoro-26-sulfan-yl)phenyl]boronic acid (Example 30, step C) | LC-MS m/z 456.3 $[M + H]^+$, ESI pos |
| 32 | 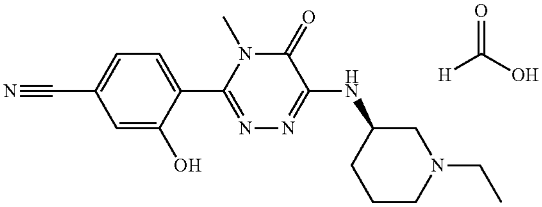 [SMILES: CCN1CCC[C@@H](Nc2nnc(-c3ccc(C#N)cc3O)n(C)c2=O)C1 ; O=CO] | 4-[6-[[(3R)-1-Ethyl-3-piperidyl]amino]-4-methyl-5-oxo-1,2,4-triazin-3-yl]-3-hydroxy-benzo-nitrile; formic acid | 3-Chloro-6-[[(3R)-1-ethyl-3-piperidyl] amino]-4-methyl-1,2,4-triazin-5-one (Example 2, step D) and 4-cyano-2-methoxy-phenylboronic acid CAS # 1256345-67-1 | LC-MS m/z 355.0 $[M + H]^+$, ESI pos |
| 33 | 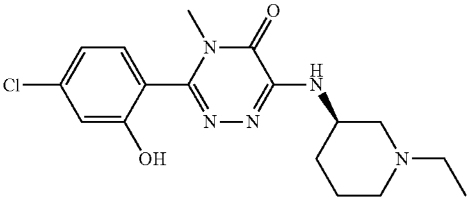 [SMILES: CCN1CCC[C@@H](Nc2nnc(-c3ccc(Cl)cc3O)n(C)c2=O)C1] | 3-(4-Chloro-2-hydroxy-phenyl)-6-[[(3R)-1-ethyl-3-piperidyl]amino]-4-methyl-1,2,4-triazin-5-one | 3-Chloro-6-[[(3R)-1-ethyl-3-piperidyl] amino]-4-methyl-1,2,4-triazin-5-one (Example 2, step D) and 4-chloro-2-methoxy-phenylboronic acid CAS # 762287-57-0 | LC-MS m/z 364.5 ([35Cl] $M + H)^+$, ESI pos |

Example 34: 3-[2-Hydroxy-4-(trifluoromethoxy) phenyl]-4-methyl-6-[[(3R)-1-methyl-3-piperidyl] amino]-1,2,4-triazin-5-one

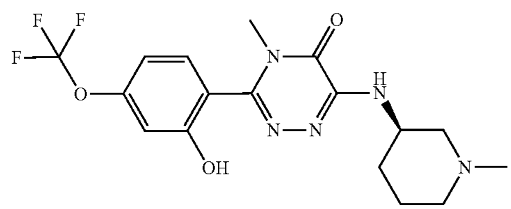 [SMILES: CN1CCC[C@@H](Nc2nnc(-c3ccc(OC(F)(F)F)cc3O)n(C)c2=O)C1]

Step A: 6-[[(3R)-1-Benzyl-3-piperidyl]amino]-3-[2-methoxy-4-(trifluoromethoxy)phenyl]-4-methyl-1,2,4-triazin-5-one 6-[[(3R)-1-Benzyl-3-piperidyl]amino]-3-chloro-4-methyl-1,2,4-triazin-5-one (Example 26, step C) (250.0 mg, 0.71 mmol, 1.0 eq), 2-methoxy-4-(trifluoromethoxy)-phenylboronic acid (184.7 mg, 0.78 mmol, 1.1 eq) and sat. aq. $Na_2CO_3$ (0.3 mL) were suspended in 1,4-Dioxane (4 mL) and the reaction mixture was sparged with $N_2$, then evacuated and back-filled with $N_2$ (3×). Xphos Pd G3 (60.3 mg, 0.07 mmol, 0.1 eq) was added and the reaction mixture placed under $N_2$, then stirred at 80° C. for 24 h. The reaction mixture was partitioned between EtOAc (50 mL) and brine (50 mL). The organic phase was isolated, dried using a phase separator and concentrated in vacuo. The resulting residue was purified by chromatography on silica gel (24 g column, 0-10% (0.7 N $NH_3$ in MeOH)/DCM) to afford the title compound (180.0 mg, 47% yield) as a light yellow solid. LC-MS m/z 490.4 $[M+H]^+$, ESI pos.

Step B: 6-[[(3R)-1-Benzyl-3-piperidyl]amino]-3-[2-methoxy-4-(trifluoromethoxy)phenyl]-4-methyl-1,2,4-triazin-5-one 6-[[(3R)-1-Benzyl-3-piperidyl]amino]-3-[2-methoxy-4-(trifluoromethoxy)phenyl]-4-methyl-1,2,4-triazin-5-one (Example 35, step A) (186.1 mg, 0.38 mmol, 1.0 eq) was dissolved in MeOH (8 mL) and 20 wt % Palladium hydroxide on carbon (50% in $H_2O$) (80.08 mg, 0.06 mmol, 0.15 eq) was added followed by formaldehyde (37 wt % in $H_2O$) (0.28 mL, 3.80 mmol, 10.0 eq). The reaction mixture was stirred under 5 bar of $H_2$ for 24 h. Further 20 wt % Palladium hydroxide on carbon (50% in $H_2O$) (91.9 mg, 0.070 mmol, 0.100 eq) was added and the reaction mixture stirred under 5 bar of $H_2$ for 24 h. The reaction mixture was filtered through a pad of Celite® and the filtrate concentrated in vacuo. The resulting residue was taken up in DCM (10 mL) and boron tribromide (1 M in DCM) (1.9 mL, 1.90 mmol, 5.0 eq) was added slowly. The reaction mixture was stirred at room temperature for 1 h, then concentrated in vacuo. The resulting residue was dissolved in MeOH (20 mL) and $Na_2CO_3$ (5 g) was added. The reaction mixture was stirred at room temperature for 45 min, then filtered and the filtrate concentrated in vacuo. The resulting residue was dissolved in 11 mL of DMSO, filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters XBridge BEH $C_{18}$ ODB prep column, 130 Å, 5 μm, 30 mm×100 mm, flow rate 40 mL min-1 eluting with a 0.3% Ammonia in water-MeCN gradient over 12.5 mins using UV across all wavelengths with PDA as well as a QDA and ELS detector. At-column dilution pump gives 2 mL min-1 MeOH over the entire method, which is included in the following MeCN percentages. Gradient information: 0.0-0.5 min, 5% MeCN: 0.5-10.5 min, ramped from 5% MeCN to 30% MeCN: 10.5-10.6 min, ramped from 30% MeCN to 100% MeCN: 10.6-12.5 min, held at 100% MeCN. The clean fractions were evaporated in a Genevac to afford the title compound (70.4 mg, 46% yield) as a white solid. LC-MS m/z 400.3 $[M+H]^+$, ESI pos.

Example 35: 6-[[(3R)-1-Ethyl-3-piperidyl]amino]-3-[2-hydroxy-4-(trifluoromethyl)phenyl]-4H-1,2,4-triazin-5-one;2,2,2-trifluoroacetic Acid

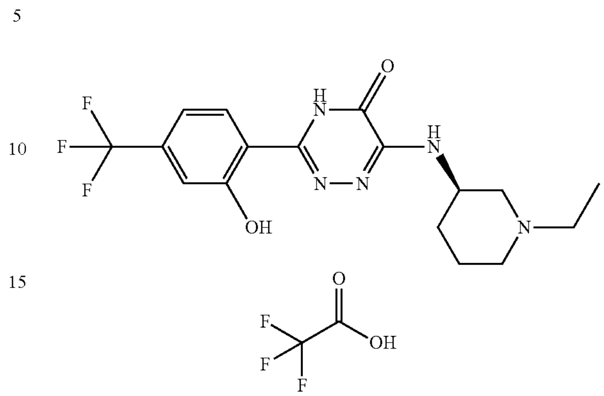

Step A: N-(Cyclopropylmethyl)-2-methoxy-4-(trifluoromethyl)benzamide

To a solution of commercially available 2-methoxy-4-(trifluoromethyl)benzoic acid (CAS #448-36-2, 2.00 g, 9.08 mmol, 1.0 eq) and commercially available cyclopropylmethanamine (CAS #2516-47-4, 0.95 mL, 10.9 mmol, 1.2 eq) in DCM (20 mL) was added DIPEA (2952.5 mg, 22.7 mmol, 2.5 eq.), EDCI (2.09 g, 10.9 mmol, 1.2 eq) and HOBt (1.60 g, 11.8 mmol, 1.3 eq). The obtained reaction mixture was stirred at 40° C. for 2 hours. After reaction completion, water (50 mL) was added and solution was extracted with EtOAc (20 mL×3). The combined organic phase was washed with brine (100 ml), dried over anhydrous sodium sulfate, filtered and concentrated under reduced pressure. The residue was purified by column chromatography (silica gel, petroleum ether:ethyl acetate=1:0 to 3:1) to afford the title compound (2.10 g, 85% yield) as yellow oil. LC-MS (Method 2): m/z 273.8 $[M+H]^+$, ESI pos.

Step B: N-(Cyclopropylmethyl)-2-methoxy-4-(trifluoromethyl)benzothioamide

To a solution of aforementioned N-(cyclopropylmethyl)-2-methoxy-4-(trifluoromethyl)benzamide (Example 35, step A) (2.10 g, 7.69 mmol, 1.0 eq.) in THF (40 mL) was added Lawessons reagent (2.312 g, 4.61 mmol, 0.6 eq.). The mixture was stirred at 70° C. for 2 hours and after completion was cooled to room temperature. The above reaction solution was diluted with water (100 mL), extracted with ethyl acetate (50 mL×3). The combined organic phase was washed with brine (50 mL), dried over anhydrous $Na_2SO_4$, filtered and concentrated under reduced pressure. The crude product was purified by silica gel column chromatography column (petroleum ether:ethyl acetate=1:0 to 10:1) to afford the title compound (2.20 g, 93% yield) as a yellow oil. LC-MS (Method 2): m/z 290 $[M+H]^+$, ESI pos.

Step C: Methyl N-(cyclopropylmethyl)-2-methoxy-4-(trifluoromethyl)benzimidothioate To a solution of aforementioned N-(cyclopropylmethyl)-2-methoxy-4-(trifluoromethyl)benzothioamide (Example 35, step B) (2.00 g, 6.91 mmol, 1.0 eq) in DMF (40 mL) was added DIEA (2.68 g, 20.74 mmol, 3.0 eq) at 20° C. and stirred at for 10 min. Then MeI (1.67 g, 11.8 mmol, 1.7 eq)

was added to the mixture. The mixture was stirred at 40° C. for 2 hours. the mixture was poured into water (100 mL) and extracted with ethyl acetate (50 mL×3). The combined organic layers were washed with brine (50 mL), dried over anhydrous sodium sulfate, filtered, and the filtrate was concentrated under reduced pressure. The residue was purified by column chromatography ($C_{18}$, 120 g, 0.1% TFA in water/MeCN), then the desired fractions were combined, lyophilized to afford the title compound (1.0 g, 48% yield) as a yellow oil. LC-MS (Method 2): m/z 303.9 $[M+H]^+$, ESI pos.

Step D: N"-(Cyclopropylmethyl)-2-methoxy-4-(trifluoromethyl)benzimidohydrazide

To a solution of methyl N-(cyclopropylmethyl)-2-methoxy-4-(trifluoromethyl)benzimidothioate (Example 35, step C) (500.0 mg, 1.65 mmol, 1.0 eq) in ethanol (15 mL) was added hydrazine hydrate (835 mg, 16.7 mmol, 10.1 eq). The mixture was stirred at 70° C. for 6 hours. The above reaction solution was cooled to room temperature and then concentrated under reduced pressure. The crude product was purified by column chromatography ($C_{18}$, 20 g, 0.1% $NH_3 \cdot H_2O$ in water/MeCN), then the desired fractions were combined and lyophilized to afford the title compound (200 mg, 41% yield) as a yellow solid. LC-MS (Method 2): m/z 288.1 $[M+H]^+$, ESI pos.

Step E: 6-Amino-4-(cyclopropylmethyl)-3-(2-methoxy-4-(trifluoromethyl)phenyl)-1,2,4-triazin-5 (4H)-one A mixture of aforementioned N"-(cyclopropylmethyl)-2-methoxy-4-(trifluoromethyl)benzimidohydrazide (Example 35, step D) (150 mg, 0.52 mmol, 1.0 eq), TEA (106 mg, 1.04 mmol, 2.0 eq) and ethyl thiooxamate (104 mg, 0.78 mmol, 1.5 eq) in ethanol (3 mL) was stirred for 1 hour at 85° C. The reaction solution was cooled to room temperature and concentrated under reduced pressure. The crude product was purified by column chromatography ($C_{18}$, 20 g, 0.1% TFA in water/MeCN), then the desired fractions were combined and lyophilized to afford the title compound (70.0 mg, 37% yield) as a yellow solid. LC-MS (Method 2): m/z 341.1 $[M+H]^+$, ESI pos.

Step F: 6-Chloro-4-(cyclopropylmethyl)-3-(2-methoxy-4-(trifluoromethyl)phenyl)-1,2,4-triazin-5 (4H)-one To a mixture of aforementioned 6-amino-4-(cyclopropylmethyl)-3-(2-methoxy-4-(trifluoromethyl)phenyl)-1,2,4-triazin-5(4H)-one (Example 35, step E) (70.0 mg, 0.21 mmol, 1.0 eq), CuCl (61.09 mg, 0.62 mmol, 3.0 eq), LiCl (17.4 mg, 0.41 mmol, 2.0 eq), benzyl(triethyl)azanium; chloride (178 mg, 0.78 mmol, 3.8 eq) in MeCN (2.5 mL) was added tert-butyl nitrite (106.1 mg, 1.03 mmol, 5.0 eq) at 25° C., then stirred at 70° C. for 1 hour under $N_2$ atmosphere. After reaction completion, the solution was cooled to room temperature, the mixture was filtered and the filtrate was concentrated in vacuum. The crude product was purified by reversed-phase flash (0.1% TFA in water/MeCN) followed by lyophilization to afford the title compound (30.0 mg, 38% yield) as yellow solid. LC-MS (Method 2): m/z 360.0 $[M+H]^+$, ESI pos.

Step G: (R)-4-(Cyclopropylmethyl)-6-((1-ethylpiperidin-3-yl)amino)-3-(2-methoxy-4-(trifluoromethyl) phenyl)-1,2,4-triazin-5(4H)-one To a mixture of aforementioned 6-chloro-4-(cyclopropylmethyl)-3-(2-methoxy-4-(trifluoromethyl)phenyl)-1,2,4-triazin-5(4H)-one (Example 35, step E) (30.0 mg, 0.08 mmol, 1.0 eq) and (3R)-1-ethylpiperidin-3-amine (53.5 mg, 0.42 mmol, 5.0 eq) in NMP (0.5 mL) was added DIEA (32.3 mg, 0.25 mmol, 3.0 eq) then stirred at 90° C. for 2 hours under $N_2$ atmosphere. The reaction mixture was filtered and the filtrate was concentrated under reduced pressure. The crude product was purified by column chromatography ($C_{18}$, 20 g, 0.1% TFA in water/MeCN), then the desired fractions were combined and lyophilized to afford the title compound (30.0 mg, 75% yield) as yellow solid. LCMS (Method 2): m/z 452.2 [M+H]+, ESI pos.

Step H: 6-[[(3R)-1-Ethyl-3-piperidyl]amino]-3-[2-hydroxy-4-(trifluoromethyl)phenyl]-4H-1,2,4-triazin-5-one;2,2,2-trifluoroacetic Acid To a solution of aforementioned (R)-4-(cyclopropylmethyl)-6-((1-ethylpiperidin-3-yl)amino)-3-(2-methoxy-4-(trifluoromethyl)phenyl)-1,2,4-triazin-5(4H)-one (Example 35, step F) (10.0 mg, 0.02 mmol, 1.0 eq) in DCM (1 mL) was added $BBr_3$ (55.4 mg, 0.22 mmol, 10.0 eq) at −40° C., then stirred at 20° C. for 1 hour. The above reaction mixture was quenched with water (0.5 mL), then the pH was adjusted to about 8 with $NH_3 \cdot H_2O$, then concentrated under reduced pressure, the residue was dissolved with methanol (2 mL), then purified by preparative HPLC (Column 3_Phenomenex Luna $C_{18}$ 75×30 mm×3 μm; Condition water (TFA)-MeOH; Begin B 23; End B 43; Gradient Time (min) 7; 100% B; Hold Time (min) 2; Flow Rate (mL/min) 25), then the solvent was removed by lyophilization to afford the title compound (0.82 mg, 7% yield) as a white solid. LCMS (Method 2): m/z 384.1 [M+H]+, ESI pos.

Example 36: 6-[[(3R,5S)-1-Methyl-5-fluoro-3-piperidyl]amino]-3-[2-hydroxy-4-(trifluoromethyl)phenyl]-4H-1,2,4-triazin-5-one;2,2,2-trifluoroacetic Acid

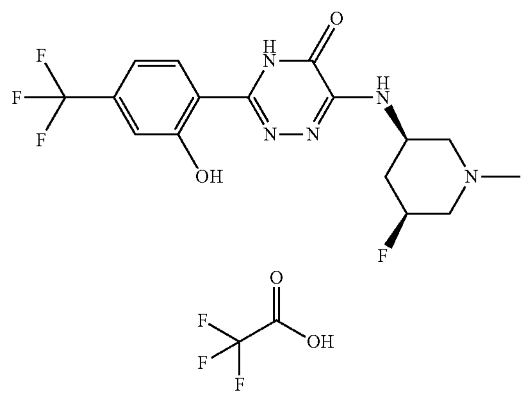

Step A: 6-[[(3R,5S)-1-Methyl-5-fluoro-3-piperidyl] amino]-3-[2-hydroxy-4-(trifluoromethyl)phenyl]-4H-1,2,4-triazin-5-one;2,2,2-trifluoroacetic Acid To a mixture of 6-(((3R,5S)-5-fluoropiperidin-3-yl) amino)-3-(2-methoxy-4-(trifluoromethyl)phenyl)-4-methyl-1,2,4-triazin-5(4H)-one (Example 16, step B) (20.0 mg, 0.05 mmol, 1.0 eq) and $K_2CO_3$ (66.4 mg, 0.48 mmol, 10.0 eq) in NMP (1 mL) was added benzenethiol (49 μL, 0.48 mmol, 10.0 eq.), under $N_2$, then stirred at 190° C. for 30 minutes under microwave conditions. The reaction mixture was cooled to 20° C., and purified by column chromatography ($C_{18}$, 0.1% TFA in water/MeCN). The eluent was lyophilized to give the product, which was purified a second time by preparative HPLC (Column: 3_Phenomenex Luna $C_{18}$ 75×30 mm×3 μm, Condition: water (0.1% TFA)-MeCN, Begin B: 15; End B: 45, Gradient Time (min): 7; 100% B Hold Time (min): 2; flow rate (mL/min): 25). The desired fractions were combined and lyophilized to afford the title compound (4.14 mg, 16% yield) as yellow solid. LCMS (Method 2): m/z 387.9 $[M+H]^+$, ESI pos.

Reference Example RE-A: 2-[6-[(1-ethyl-3-piperidyl)amino]-4-methyl-pyridazin-3-yl]-5-(trifluoromethyl)phenol RE-A was synthesized in analogy to as described in WO20200234715.

Example A'

A compound of formula Ib can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B'

A compound of formula Ib can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example A

A compound of formula I can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula Ib;

Ib

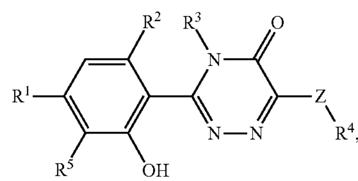

wherein $R^1$ is H, acetyl, $SF_5$, halo, alkyl, haloalkyl, haloalkoxy or nitrile;

$R^5$ is H;

or $R^1$ and $R^5$, and the atoms to which they are bonded, form either an 4-6 membered heterocycle ring comprising a single O heteroatom optionally substituted with one or two substituents independently selected from halo or alkyl, or $R^1$ and $R^5$, and the atoms to which they are bonded, form a 3-6 membered cycloalkyl ring optionally substituted with 1 to 2 substituents independently selected from halo or alkyl;

$R^2$ is H, halo, alkyl, haloalkyl, cycloalkyl or cycloalkylalkyl, wherein cycloalkyl or cycloalkylalkyl is optionally substituted with halo;

$R^3$ is H, alkyl, haloalkyl, cycloalkyl or cycloalkylalkyl, wherein cycloalkyl or cycloalkylalkyl is optionally substituted with halo;

Z is —O—, or —NH—;

$R^4$ is a heterocycle ring optionally substituted with 1 to 3 substituents independently selected from halo, alkyl, haloalkyl, hydroxyalkyl, —OH, oxo, —$CO_2$H, cycloalkylalkyl or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl has 1 to 3 substituents independently selected from alkyl, halo, haloalkyl and —OH;

or a pharmaceutically acceptable salt thereof.

2. The compound or pharmaceutically acceptable salt thereof according to claim 1, wherein $R^5$ is H or $R^1$ and $R^5$, and the atoms to which they are bonded, form either an 4-6 membered heterocycle ring comprising a single O heteroatom or $R^1$ and $R^5$, and the atoms to which they are bonded, form a 3-6 membered cycloalkyl ring.

3. The compound or pharmaceutically acceptable salt thereof according to claim 1, wherein $R^5$ is H or $R^1$ and $R^5$, and the atoms to which they are bonded, form a 5 membered heterocycle ring comprising a single O atom.

4. The compound or pharmaceutically acceptable salt thereof according to claim 1, wherein $R^5$ is H.

5. The compound or pharmaceutically acceptable salt thereof according to claim 1, wherein $R^1$ is acetyl, $SF_5$, halo, haloalkyl, haloalkoxy or nitrile.

6. The compound or pharmaceutically acceptable salt thereof according to claim 1, wherein $R^1$ is halo, haloalkyl or haloalkoxy.

7. The compound or pharmaceutically acceptable salt thereof according to claim 1, wherein $R^1$ is haloalkoxy.

8. The compound or pharmaceutically acceptable salt thereof according to claim 1, wherein $R^2$ is H or alkyl.

9. The compound or pharmaceutically acceptable salt thereof according to claim 1, wherein $R^2$ is H.

10. The compound or pharmaceutically acceptable salt thereof according to claim 1, wherein $R^3$ is H, alkyl or cycloalkyl.

11. The compound or pharmaceutically acceptable salt thereof according to claim 1, wherein $R^3$ is alkyl.

12. The compound or pharmaceutically acceptable salt thereof according to claim 1, wherein $R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with —OH.

13. The compound or pharmaceutically acceptable salt thereof according to claim 1, wherein $R^4$ is a piperidyl ring optionally substituted with alkyl.

14. The compound or pharmaceutically acceptable salt thereof according to claim 1, wherein $R^4$ is ethylpiperidine.

15. The compound or pharmaceutically acceptable salt thereof according to claim 1, wherein Z is —NH—.

16. The compound according to claim 1, wherein $R^1$ is acetyl, $SF_5$, halo, haloalkyl, haloalkoxy or nitrile;

$R^5$ is H;

or $R^1$ and $R^5$, and the atoms to which they are bonded, form either an 4-6 membered heterocycle ring comprising a single O heteroatom or $R^1$ and $R^5$, and the atoms to which they are bonded, form a 3-6 membered cycloalkyl ring;

$R^2$ is H or alkyl;

$R^3$ is H, alkyl or cycloalkyl;

Z is —NH—;

$R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with —OH;

or a pharmaceutically acceptable salt thereof.

17. The compound according to claim 1, wherein $R^1$ is acetyl, $SF_5$, halo, haloalkyl, haloalkoxy or nitrile;

$R^5$ is H;

or $R^1$ and $R^5$, and the atoms to which they are bonded, form a 5 membered heterocycle ring comprising a single O;

$R^2$ is H or alkyl;

$R^3$ is H, alkyl or cycloalkyl;

Z is —NH—;

$R^4$ is a heterocycle ring optionally substituted with 1 to 3 substituents independently selected from halo, alkyl, cycloalkyl, or cycloalkylalkyl; or $R^4$ is a cycloalkyl optionally substituted with 2 substituents independently selected from alkyl, and —OH; or $R^4$ is arylalkyl substituted with —OH;

or a pharmaceutically acceptable salt thereof.

18. The compound according to claim 1, wherein $R^1$ is halo, haloalkyl, or haloalkoxy;

$R^5$ is H;

or $R^1$ and $R^5$, and the atoms to which they are bonded, form a 5 membered heterocycle ring comprising a single O;

$R^2$ is H;

$R^3$ is alkyl;

Z is-NH—;

$R^4$ is a piperidyl ring optionally substituted with alkyl;

or a pharmaceutically acceptable salt thereof.

19. The compound according to claim 1, wherein $R^1$ is haloalkoxy;

$R^5$ is H;

$R^2$ is H;

$R^3$ is alkyl;

Z is —NH—;

$R^4$ is a piperidyl ring optionally substituted with alkyl;

or a pharmaceutically acceptable salt thereof.

20. The compound according to claim 1, wherein the compound is selected from:

6-((1-Ethylpiperidin-3-yl)amino)-3-(2-hydroxy-4-(trifluoromethyl)phenyl)-4-methyl-1,2,4-triazin-5(4H)-one;

6-[[(3R)-1-Ethyl-3-piperidyl]amino]-3-(4-hydroxy-2,3-dihydrobenzofuran-5-yl)-4-methyl-1,2,4-triazin-5-one;

3-[2-Hydroxy-4-(trifluoromethyl)phenyl]-4-methyl-6-[[(3R)-3-piperidyl]amino]-1,2,4-triazin-5-one;

3-[2-Hydroxy-4-(trifluoromethyl)phenyl]-4-methyl-6-[(8-methyl-8-azabicyclo[3.2.1]octan-2-yl)amino]-1,2,4-triazin-5-one;

(R)-6-((1-(Cyclopropylmethyl) piperidin-3-yl)amino)-3-(2-hydroxy-4-(trifluoromethyl)phenyl)-4-methyl-1,2,4-triazin-5(4H)-one;

(R)-3-(2-Hydroxy-4-(trifluoromethyl)phenyl)-4-methyl-6-((1-methylpiperidin-3-yl)amino)-1,2,4-triazin-5(4H)-one;

6-(1,2,3,5,6,7,8,8a-Octahydroindolizin-8-ylamino)-3-[2-hydroxy-4-(trifluoromethyl)phenyl]-4-methyl-1,2,4-triazin-5-one;

3-[2-Hydroxy-4-(trifluoromethyl)phenyl]-4-methyl-6-[[(3R)-1-propyl-3-piperidyl]amino]-1,2,4-triazin-5-one;

3-[2-Hydroxy-4-(trifluoromethyl)phenyl]-4-methyl-6-[(1,5,5-trimethyl-3-piperidyl)amino]-1,2,4-triazin-5-one;

(R)-6-((1-Cyclopropylpiperidin-3-yl)amino)-3-(2-hydroxy-4-(trifluoromethyl)phenyl)-4-methyl-1,2,4-triazin-5(4H)-one;

6-(((1S,3S)-3-Hydroxy-3-methylcyclobutyl)amino)-3-(2-hydroxy-4-(trifluoromethyl)phenyl)-4-methyl-1,2,4-triazin-5(4H)-one;

6-[(1-tert-Butyl-3-piperidyl)amino]-3-[2-hydroxy-4-(trifluoromethyl)phenyl]-4-methyl-1,2,4-triazin-5-one;

6-(2-Azabicyclo[2.2.1]heptan-6-ylamino)-3-[2-hydroxy-4-(trifluoromethyl)phenyl]-4-methyl-1,2,4-triazin-5-one;

6-[[(3R,5S)-1-Ethyl-5-methyl-3-piperidyl]amino]-3-[2-hydroxy-4-(trifluoromethyl)phenyl]-4-methyl-1,2,4-triazin-5-one;

6-[[(3R,5R)-1-Ethyl-5-methyl-3-piperidyl]amino]-3-[2-hydroxy-4-(trifluoromethyl)phenyl]-4-methyl-1,2,4-triazin-5-one;

6-[[(5S)-5-fluoro-1-methyl-3-piperidyl]amino]-3-[2-hydroxy-4-(trifluoromethyl)phenyl]-4-methyl-1,2,4-triazin-5-one;

6-[[(3R)-6,6-Dimethyl-3-piperidyl]amino]-3-[2-hydroxy-4-(trifluoromethyl)phenyl]-4-methyl-1,2,4-triazin-5-one;

6-[(3-Hydroxyphenyl)methylamino]-3-[2-hydroxy-4-(trifluoromethyl)phenyl]-4-methyl-1,2,4-triazin-5-one;

6-[[(3R)-1-Ethyl-3-piperidyl]amino]-3-[2-hydroxy-4-(trifluoromethyl)phenyl]-4-methyl-1,2,4-triazin-5-one;

4-Cyclopropyl-6-[[(3R)-1-ethyl-3-piperidyl]amino]-3-[2-hydroxy-4-(trifluoromethyl)phenyl]-1,2,4-triazin-5-one;

6-[[(3R)-1-Ethyl-3-piperidyl]amino]-3-(4-fluoro-2-hydroxy-phenyl)-4-methyl-1,2,4-triazin-5-one;

4-Ethyl-6-[[(3R)-1-ethyl-3-piperidyl]amino]-3-[2-hydroxy-4-(trifluoromethyl)phenyl]-1,2,4-triazin-5-one;

3-[4-(Difluoromethoxy)-2-hydroxy-phenyl]-6-[[(3R)-1-ethyl-3-piperidyl]amino]-4-methyl-1,2,4-triazin-5-one;

3-[4-(1,1-Difluoroethyl)-2-hydroxy-phenyl]-6-[[(3R)-1-ethyl-3-piperidyl]amino]-4-methyl-1,2,4-triazin-5-one;

3-(4-Acetyl-2-hydroxy-phenyl)-6-[[(3R)-1-ethyl-3-piperidyl]amino]-4-methyl-1,2,4-triazin-5-one;

3-[2-hydroxy-4-(trifluoromethyl)phenyl]-4-methyl-6-[[(3R)-1-methyl-3-piperidyl]amino]-1,2,4-triazin-5-one;

6-[[(3R)-1-Ethyl-3-piperidyl]amino]-3-[2-hydroxy-4-(trifluoromethoxy)phenyl]-4-methyl-1,2,4-triazin-5-one;

6-[[(3R)-1-Ethyl-3-piperidyl]amino]-3-[2-hydroxy-6-methyl-4-(trifluoromethyl)phenyl]-4-methyl-1,2,4-triazin-5-one;

(M or P)-6-[[(3R)-1-ethyl-3-piperidyl]amino]-3-[2-hydroxy-6-methyl-4-(trifluoromethyl)phenyl]-4-methyl-1,2,4-triazin-5-one;

(P or M)-6-[[(3R)-1-ethyl-3-piperidyl]amino]-3-[2-hydroxy-6-methyl-4-(trifluoromethyl)phenyl]-4-methyl-1,2,4-triazin-5-one;

6-[[(3R)-1-Ethyl-3-piperidyl]amino]-3-[2-hydroxy-4-(pentafluoro-26-sulfanyl)phenyl]-4-methyl-1,2,4-triazin-5-one;

4-[6-[[(3R)-1-Ethyl-3-piperidyl]amino]-4-methyl-5-oxo-1,2,4-triazin-3-yl]-3-hydroxy-benzonitrile;

3-(4-Chloro-2-hydroxy-phenyl)-6-[[(3R)-1-ethyl-3-piperidyl]amino]-4-methyl-1,2,4-triazin-5-one;

3-[2-Hydroxy-4-(trifluoromethoxy)phenyl]-4-methyl-6-[[(3R)-1-methyl-3-piperidyl]amino]-1,2,4-triazin-5-one;

6-[[(3R)-1-Ethyl-3-piperidyl]amino]-3-[2-hydroxy-4-(trifluoromethyl)phenyl]-4H-1,2,4-triazin-5-one; and 6-[[(3R,5S)-1-ethyl-5-fluoro-3-piperidyl]amino]-3-[2-hydroxy-4-(trifluoromethyl)phenyl]-4H-1,2,4-triazin-5-one;

or a pharmaceutically acceptable salt thereof.

21. The compound according to claim 1, wherein the compound is selected from:

6-[[(3R)-1-Ethyl-3-piperidyl]amino]-3-(4-hydroxy-2,3-dihydrobenzofuran-5-yl)-4-methyl-1,2,4-triazin-5-one;

(R)-3-(2-Hydroxy-4-(trifluoromethyl)phenyl)-4-methyl-6-((1-methylpiperidin-3-yl)amino)-1,2,4-triazin-5(4H)-one;

6-[[(3R)-1-Ethyl-3-piperidyl]amino]-3-[2-hydroxy-4-(trifluoromethyl)phenyl]-4-methyl-1,2,4-triazin-5-one;

3-[4-(Difluoromethoxy)-2-hydroxy-phenyl]-6-[[(3R)-1-ethyl-3-piperidyl]amino]-4-methyl-1,2,4-triazin-5-one;

6-[[(3R)-1-Ethyl-3-piperidyl]amino]-3-[2-hydroxy-4-(trifluoromethoxy)phenyl]-4-methyl-1,2,4-triazin-5-one;

3-(4-Chloro-2-hydroxy-phenyl)-6-[[(3R)-1-ethyl-3-piperidyl]amino]-4-methyl-1,2,4-triazin-5-one; and 3-[2-Hydroxy-4-(trifluoromethoxy)phenyl]-4-methyl-6-[[(3R)-1-methyl-3-piperidyl]amino]-1,2,4-triazin-5-one;

or a pharmaceutically acceptable salt thereof.

22. The compound according to claim 1, wherein the compound is 6-[[(3R)-1-Ethyl-3-piperidyl]amino]-3-[2-hydroxy-4-(trifluoromethoxy)phenyl]-4-methyl-1,2,4-triazin-5-one, or a pharmaceutically acceptable salt thereof.

23. A process to prepare the compound or pharmaceutically acceptable salt thereof according to claim 1, comprising reacting a compound of formula XI to form a compound of formula XII,

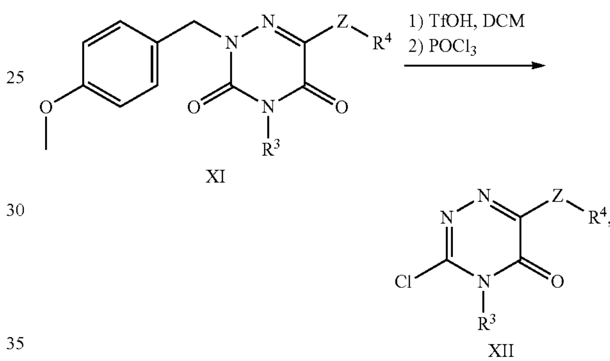

XI

XII wherein $R^3$ is H, alkyl, haloalkyl, cycloalkyl or cycloalkylalkyl, wherein cycloalkyl or cycloalkylalkyl is optionally substituted with halo;

Z is —O—, or —NH—; and $R^4$ is a heterocycle ring optionally substituted with 1 to 3 substituents independently selected from halo, alkyl, haloalkyl, hydroxyalkyl, —OH, oxo, —$CO_2$H, cycloalkylalkyl or cycloalkyl optionally substituted with halo; or $R^4$ is a cycloalkyl optionally substituted with 1 to 3 substituents independently selected from alkyl, halo, haloalkyl and —OH; or $R^4$ is arylalkyl or heteroarylalkyl wherein arylalkyl or heteroarylalkyl has 1 to 3 substituents independently selected from alkyl, halo, haloalkyl and —OH.

24. A method for the treatment of asthma in a patient in need thereof, which method comprises administering to the patient an effective amount of the compound or pharmaceutically acceptable salt thereof according to claim 1.

25. A method for the treatment of chronic obstructive pulmonary disease (COPD) in a patient in need thereof, which method comprises administering to the patient an effective amount of the compound or pharmaceutically acceptable salt thereof according to claim 1.

* * * * *